(12) United States Patent
Hatada et al.

(10) Patent No.: US 10,612,044 B2
(45) Date of Patent: Apr. 7, 2020

(54) DNA METHYLATION EDITING KIT AND DNA METHYLATION EDITING METHOD

(71) Applicant: NATIONAL UNIVERSITY CORPORATION GUNMA UNIVERSITY, Gunma (JP)

(72) Inventors: Izuho Hatada, Gunma (JP); Sumiyo Morita, Gunma (JP); Takuro Horii, Gunma (JP)

(73) Assignee: NATIONAL UNIVERSITY CORPORATION GUNMA UNIVERSITY, Gunma (JP)

( * ) Notice: Subject to any disclaimer, the term of this patent is extended or adjusted under 35 U.S.C. 154(b) by 0 days.

(21) Appl. No.: 15/779,227

(22) PCT Filed: Nov. 25, 2016

(86) PCT No.: PCT/JP2016/084958
§ 371 (c)(1),
(2) Date: May 25, 2018

(87) PCT Pub. No.: WO2017/090724
PCT Pub. Date: Jun. 1, 2017

(65) Prior Publication Data
US 2018/0346932 A1 Dec. 6, 2018

(30) Foreign Application Priority Data
Nov. 25, 2015 (JP) ................................. 2015-229896

(51) Int. Cl.
| | |
|---|---|
| C12N 9/00 | (2006.01) |
| C12N 15/90 | (2006.01) |
| C07K 16/18 | (2006.01) |
| C12N 5/10 | (2006.01) |
| C12N 9/10 | (2006.01) |
| C12N 15/09 | (2006.01) |
| C07K 16/44 | (2006.01) |
| C12N 1/00 | (2006.01) |
| C12N 15/11 | (2006.01) |

(52) U.S. Cl.
CPC ............ *C12N 15/907* (2013.01); *C07K 16/18* (2013.01); *C07K 16/44* (2013.01); *C12N 1/00* (2013.01); *C12N 5/10* (2013.01); *C12N 9/10* (2013.01); *C12N 15/09* (2013.01); *C12N 15/111* (2013.01); *C07K 2317/622* (2013.01); *C07K 2319/01* (2013.01); *C07K 2319/21* (2013.01); *C07K 2319/60* (2013.01); *C07K 2319/80* (2013.01); *C12N 2310/20* (2017.05); *C12Y 201/01037* (2013.01)

(58) Field of Classification Search
None
See application file for complete search history.

(56) References Cited

U.S. PATENT DOCUMENTS

2016/0010076 A1    1/2016  Joung et al.
2017/0219596 A1*   8/2017  Tanenbaum ........... G01N 21/64

FOREIGN PATENT DOCUMENTS

WO    2014/152432    9/2014

OTHER PUBLICATIONS

Schultz et al (Nature Structural and Molecular Biology 1998, vol. 5, No. 1, pp. 19-24, abstract).*
Tanenbaum et al., "A Protein-Tagging System for Signal Amplification in Gene Expression and Fluorescence Imaging", Cell, vol. 159, 2014, pp. 635-646.
Maeder et al., "Targeted DNA demethylation and activation of endogenous genes using programmable TALE-TET1 fusion proteins", Nature Biotechnology, 2013, vol. 31, No. 12, pp. 1137-1142.
Mali et al., "Cas9 as a versatile tool for engineering biology", Nature Methods, vol. 10, No. 10, 2013, pp. 957-963.
Yamazaki et al., BMB 2015 Koen Yoshishu, 2015, #1P0832 with its partial English translation.
Shen et al., "A single amino acid substitution confers enhanced methylation activity of mammalian Dnmt3b on chromatin DNA", Nucleic Acids Research, 2010, vol. 38, No. 18, pp. 6054-6064.
Cabantous et al., "A New Protein-Protein Interaction Sensor Based on Tripartite Split-GFP Association", Scientific Reports, 2013, vol. 3, No. 2854, 9 pages.
Skelton et al., "Origins of PDZ Domain Ligand Specificity", The Journal of Biological Chemistry, 2003, vol. 278, No. 9, pp. 7645-7654.
Morita et al., "Targeted DNA demethylation in vivo using dCas9-peptide repeat and scFv-TET1 catalytic domain fusions", Nature Biotechnology, vol. 34, No. 10, 2016, pp. 1060-1065.
Hatada et al., Jikken Igaku, vol. 32, No. 11, 2014, pp. 1690-1714, with partial English translation.
International Search Report dated Jan. 31, 2017 in International Application No. PCT/JP2016/084958.
International Preliminary Report on Patentability dated May 31, 2018 in International Application No. PCT/JP2016/084958.
Extended European Search Report dated Apr. 5, 2019 in corresponding European Patent Application No. 16868667.3.
Bernstein et al., "TALE-mediated epigenetic suppression of CDKN2A increases replication in human fibroblasts", The Journal of Clinical Investigation, 2015, vol. 125, No. 5, pp. 1998-2006.

* cited by examiner

*Primary Examiner* — Celine X Qian
(74) *Attorney, Agent, or Firm* — Wenderoth, Lind & Ponack, L.L.P.

(57) ABSTRACT

A DNA methylation editing kit comprises: (1) a fusion protein of inactivated CRISPR-associated endonuclease Cas9 (dCas9) having no nuclease activity and a tag peptide array in which plural tag peptides are linked by linkers, or an RNA or DNA coding therefor; (2) a fusion protein(s) of a tag peptide-binding portion and a methylase or demethylase, or an RNA(s) or DNA(s) coding therefor; and (3) a guide RNA(s) (gRNA(s)) comprising a sequence complementary to a DNA sequence within 1 kb of a desired site of methylation or demethylation, or a DNA(s) expressing the gRNA(s).

7 Claims, 9 Drawing Sheets

Specification includes a Sequence Listing.

(a)

(b)

DNA METHYLATION EDITING KIT AND DNA METHYLATION EDITING METHOD

TECHNICAL FIELD

The present invention relates to a DNA methylation editing kit and a DNA methylation editing method.

BACKGROUND ART

The methylation of cytosine in genomic DNA is a typical modification of epigenetics (epigenome) regulating gene expression. Possible regulation of the methylation of a particular gene enables elucidation of epigenome diseases such as cancer, production of models of the diseases, and its application to epigenome treatment. Currently, treatment of cancer using the demethylation of the whole genome with 5-azacytosine or the like is put into practical use. However, the treatment affects all genes, and therefore, some doubt remains as to safety concerns. Therefore, development of a technology for regulating the methylation of a particular site has been desired.

As such a technology for regulating the methylation of a particular site, a technology for demethylating a particular gene by using a protein obtained by fusing TALEN and the catalytic domain of TET1 which is an enzyme involved in demethylation has been previously reported (Non Patent Literature 1). However, it was very time-consuming due to use of TALEN, which is a genome editing technology of the previous-generation, and the degree of demethylation has not been very high.

Examples of new-generation genome editing methods include a method of using CRISPR/Cas (Non Patent Literature 2). Although use and application of an array in which plural peptide epitopes are linked, and scFv which is a single-chain antibody for signal amplification have been reported (Non Patent Literature 3) as a CRISPR/Cas genome editing method, the method has not been known to be applied to regulation of DNA methylation.

CITATION LIST

Non Patent Literature

Non Patent Literature 1: Maeder M L et al. Nat. Biotechnol, 31, 1137-1142, 2013
Non Patent Literature 2: JIKKEN IGAKU (YODOSHA CO., LTD.) July, 2014, pp. 1690-1714
Non Patent Literature 3: Tanenbaum M E et al. Cell 159, 635-646, 2014

SUMMARY OF INVENTION

Technical Problem

In view of the problems described above, an object of the present invention is to provide a DNA methylation editing kit and a DNA methylation editing method.

Solution to Problem

As a result of intensive study for solving the problems described above, the present inventors found that use of a CRISPR/Cas genome editing method enables the methylation of a particular site to be effectively regulated, and the present invention was thus accomplished.

In other words, the gist of the present invention is as follows.

[1] A DNA methylation editing kit comprising:
(1) a fusion protein of inactivated CRISPR-associated endonuclease Cas9 (dCas9) having no nuclease activity and a tag peptide array in which a plurality of tag peptides are linked by linkers, or an RNA or DNA coding therefor;
(2) a fusion protein(s) of a tag peptide-binding portion and a methylase or demethylase, or an RNA(s) or DNA(s) coding therefor; and
(3) a guide RNA(s) (gRNA(s)) comprising a sequence complementary to a DNA sequence within 1 kb of a desired site of methylation or demethylation, or a DNA(s) expressing the gRNA(s).

[2] The DNA methylation editing kit according to [1], wherein the demethylase is a catalytic domain (TET1CD) of ten-eleven translocation 1.

[3] The DNA methylation editing kit according to [1], wherein the methylase is DNA methyltransferase 3 beta (DNMT3B).

[4] The DNA methylation editing kit according to any one of [1] to [3], wherein the tag peptides are peptide epitopes, and the tag peptide-binding portion is an anti-peptide-epitope antibody.

[5] The DNA methylation editing kit according to [4], wherein the peptide epitopes are general control non-derepressible 4 (GCN4) peptide epitopes, and the anti-peptide-epitope antibody is an anti-GCN4 peptide epitope antibody.

[6] The DNA methylation editing kit according to [4], wherein the peptide epitopes are His tags or EE tags, and the anti-peptide-epitope antibody is an anti-His tag antibody or an anti-EE tag antibody.

[7] The DNA methylation editing kit according to any one of [4] to [6], wherein the antibody is a single-chain antibody (scFv).

[8] The DNA methylation editing kit according to any one of to [1] to [3], wherein the tag peptides are a small fragment of a split protein, and the tag peptide-binding portion is a large fragment of the split protein.

[9] The DNA methylation editing kit according to [8], wherein the split protein is GFP.

[10] The DNA methylation editing kit according to any one of [1] to [3], wherein the tag peptides are GVKESLV, and the tag peptide-binding portion is PDZ protein.

[11] The DNA methylation editing kit according to any one of [1] to [10], wherein the linkers consist of 5 to 100 amino acids.

[12] The DNA methylation editing kit according to any one of [1] to [11], wherein the linkers consist of 5 to 50 amino acids.

[13] The DNA methylation editing kit according to any one of [1] to [12], wherein the linkers consist of 10 to 50 amino acids.

[14] The DNA methylation editing kit according to any one of [1] to [13], wherein the fusion proteins of the (1) and/or (2) further include a selection marker.

[15] The DNA methylation editing kit according to any one of [1] to [14], which contains plural gRNAs [16] The DNA methylation editing kit according to any one of [1] to [15], wherein all the DNAs of the (1) to (3) are contained in one vector.

[17] A DNA methylation editing method comprising transfecting a cell with the following (1) to (3).
(1) a fusion protein of inactivated CRISPR-associated endonuclease Cas9 (dCas9) having no nuclease activity and a tag peptide array in which a plurality of tag peptides are linked by linkers, or an RNA or DNA coding therefor;

(2) a fusion protein(s) of a tag peptide-binding portion and a methylase or demethylase, or an RNA(s) or DNA(s) coding therefor; and (3) a guide RNA(s) (gRNA(s)) comprising a sequence complementary to a DNA sequence within 1 kb of a desired site of methylation or demethylation, or a DNA(s) expressing the gRNA(s).

[18] The DNA methylation editing method according to [17], wherein the fusion proteins of the (1) and or (2) further include a selection marker.

[19] The DNA methylation editing method according to [18], further comprising selecting and collecting a cell expressing the selection marker.

Advantageous Effects of Invention

According to the present invention, it is possible to regulate the DNA methylation of as particular site, for example, to demethylate methylated site, and to methylate an unmethylated site.

DESCRIPTION OF EMBODIMENTS

Embodiments of the present invention will be described in detail below.

Figure 3A:
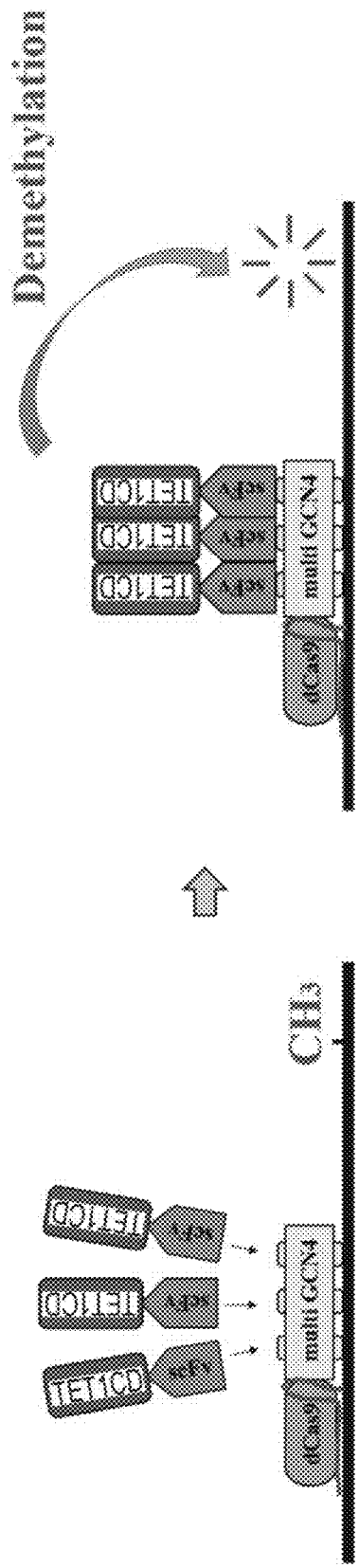
FIG. 3A is a view illustrating a scheme of demethylation amplification based on dCas9 and a repeating peptide array. Inactivated Cas9 (dCas9) fused with the repeating peptide array and having no nuclease activity can recruit plural pieces of scFv antibody-fused TET1CD. Therefore, the plural pieces of TET1CD can more effectively demethylate a target.

In CRISPR/Cas, Cas9, which is a DNA-cleaving enzyme, forms a complex with a short RNA (guide RNA (gRNA)) comprising an about-20-bp sequence complementary to a target, and cleaves DNA as a target (Non Patent Literature 2). In such a case, when a mutant enzyme having no DNA cleavage activity, referred to as dCas9, is used, only binding to a target can be achieved without cleaving the target. Thus, recruitment of factors that perform methylation and demethylation by linking various components to dCas9 enables the methylation of a particular gene to be regulated. When a system where dCas9 linked with a tag peptide array comprising plural tag peptides, and a is peptide-binding portion such as a single-chain antibody (scFv) for a tag peptide fused with a factor performing methylation and demethylation are used, and plural methylation factors or demethylation factors can be recruited for one molecule of dCas9, and an ability to perform the methylation or demethylation can be enhanced (FIG. 3a).

In the present invention, first, a sequence (target sequence) complementary to a DNA sequence within 1 kb from a desired site of methylation or demethylation is produced, and a gRNA comprising the target sequence is produced. The gRNA has a property of forming a complex, with dCas9 having no nuclease activity. When a fusion protein of dCas9 and a tag peptide array is produced, the gRNA forms a complex with the fusion protein, through dCas9, and therefore, a gRNA-dCas9-tag peptide array complex is formed. The gRNA is bound to a sequence complementary to a target sequence included in the gRNA, and therefore, the gRNA-dCas9-tag peptide array complex is bound to a DNA sequence within 1 kb from a desired site of methylation or demethylation. A fusion protein of a tag peptide-binding portion and a methylase or demethylase is recruited within 1 kb from the desired site of methylation or demethylation by binding of the tag peptide-binding portion to the tag peptide array. The recruited methylase or demethylase methylates or demethylates a site within 1 kb from its recruited portion (FIG. 3a).

(DNA Methylation Editing Kit and DNA Methylation Editing Method)

The present invention relates to a DNA methylation editing kit comprising: (1) a fusion protein of inactivated CRISPR-associated endonuclease Cas9 (dCas9) having no nuclease activity and a tag peptide array in which plural tag peptides such as GCN4 are linked by linkers, or an RNA or DNA coding therefor; (2) a fusion protein(s) of a tag peptide-binding portion such, as an anti-tag peptide antibody and a methylase or demethylase, or an RNA(s) or DNA(s) coding therefor; and (3) a guide RNA(s) (gRNA(s)) comprising a sequence complementary to a DNA sequence within 1 kb from a desired site of demethylation, or a DNA(s) expressing the gRNA(s). In addition, the present invention relates to a DNA methylation editing method comprising transfecting a cell with the (1) to (3) described above.

The DNA methylation editing includes both of the methylation of a DNA unmethylated site and the demethylation of a DNA methylated site.

(Inactivated Cas9 Having No Nuclease Activity)

CRISPR-associated end nuclease Cas9 (Cas9) includes two lobes of a RLC lobe (REC: recognition) and a NUC lobe (NUC: nuclease), in which the NUC lobe is a site responsible for nuclease activity (Non Patent Literature 2). Thus, inactivated Cas9 (dCas9) having no nuclease activity in the present invention can be produced by introducing a mutation into the NUC lobe of Cas9. As a result, the nuclease activity of Cas9 can be inactivated while maintaining the capacity of binding to a target site. A site in which the mutation is introduced into the NUC lobe is not limited as long as only the nuclease activity can be inactivated. For example, mutation of Asp10 to alanine (D10A), mutation of His840 to alanine (H840A), and mutation of Asn863 to alanine (N863A) in Cas9 (UniProtKB/Swiss-Prot Q99ZW2) are preferred. Such mutations may be one kind or a combination of two or more kinds thereof.

DNAs encoding dCas9 can be produced by introducing mutations into DNAs encoding Cas9 that can be obtained from GenBank and the like. Alternatively, plasmids comprising commercially available dCas9 may be obtained from Addgene and the like and used, DNAs encoding dCas9 may be obtained by PCR with the plasmids as templates or may be artificially produced using an artificial gene synthesis technology known to those skilled in the art, and methods of obtaining the DNAs are not limited. RNAs encoding dCas9 may be obtained by known molecular biological techniques, of which any may be used. For example, such an RNA may be obtained by using a DNA encoding the dCas9 as a template and triggering an RNA polymerase.

(Tag Peptide Array)

The tag peptide array in the present invention refers to a tag peptide array in which plural tag peptides are linked by linkers.

The tag peptides can be optionally selected in combination with a tan peptide-binding portion described later. Examples of the combination of the tag peptides and the tag peptide-binding portion include a combination of a peptide epitope and an antibody recognizing the peptide epitope, and a combination of the small fragment and large fragment of a split protein.

Examples of the combination of a peptide epitope and an antibody recognizing the peptide epitope include: GCN4 and an anti-GCN4 antibody; a His tag and an anti-His tag antibody, an EE hexapeptide and an anti-EE hexapeptide antibody; a c-Myc tag and an anti-c-Myc tag antibody; an HA tag and an anti-HA tag antibody; an S tag and an anti-S tag antibody; and a FLAG tag and an anti-FLAG tag antibody (Protein Engineering, Design & Selection vol. 24 no. 5 pp. 419-428, 2011). Among them, a peptide included in GCN4 is preferably used, the amino acid sequence of GCN4 can be obtained from, for example, PDB, and the DNA sequence of GCN4 can be obtained from GenBank or the like. Those skilled in the art can also obtain an RNA sequence corresponding to the DNA sequence on the basis of information on the DNA sequence by using nucleotide sequence conversion software and the like. The GCN4 peptide epitope can be used without limitation as long as being an epitope in GCN4, and an amino acid sequence represented by SEQ ID NO: 1 is preferred. Information on the amino acid sequences of the other tag peptides and the nucleotide sequences encoding the amino acid sequences can be obtained from known databases and the like.

The split protein refers to a pair of proteins in which, in the case of dividing a certain protein into two portions, the two portions of the protein are reassociated, thereby enabling formation of the same structure as that of the original protein. Particularly in the case of dividing the original protein into the two portions, one portion as a short peptide (small fragment) may be used with a tag peptide, and the other longer portion (large fragment) may be used as a tag peptide-binding portion (Current Opinion in Chemical Biology 2011, 15: 789-797). A known split protein can be used as the split protein which can be used for such a purpose, and examples thereof include GFP (green fluorescent protein).

Further, binding of a peptide and a protein domain is compiled into a database, and a combination of a tag peptide and a tag peptide-binding portion can be found with reference to, for example, Peptide Binding Proteins Database (http://pepbind.bicpu.edu.in/home.php). For example, since PDZAlpha-Syntrophin PDZ protein interaction domain can be bound to GVKESLV (SEQ ID NO: 44), GVKESLV can be used with a tag peptide, and the PDZ domain can be used as a tag peptide-binding portion.

Further, the binding strength of a pair of a peptide and a peptide binding portion can be increased by connecting another unrelated domain with a linker and performing domain interface evolution. Methylation cart be further efficiently regulated by using such a pair (Prot. Natl. Acad. Sci. USA, 2008, vol, 105 no. 18, 6578-6583).

Linkers interposed in a tag peptide array comprising such plural tag peptides as described above include any sequence as long as the linkers do not inhibit binding of the peptides and peptide-binding portions or the desired effect of the present invention. Examples of the linkers include a repeating sequence of glycine and serine. The length of such a linker can be set as appropriate according to the kind of a methylase or demethylase and the like, and is preferably 5 to 100 amino acids, more preferably 5 to 50 amino acids, and still more preferably 10 to 50 amino acids. In the case of TET and DNMT described later, the length is more preferably 15 to 40 amino acids, still more preferably 17 to 30 amino acids, and most preferably 22 amino acids. When the length of the linker is 10 amino acids in the case of the repeating sequence of glycine (G) and serine (S), for example, the linker sequence may be GSGSG (SEQ ID NO: 45), GSGSGGSGSGSGGSGSGGSGSG (SEQ ID NO: 46), or GSGSGGSGSGGSGSGGSGSGGSGGSGSGGSGSGG SGSGGSGSG (SEQ ID NO: 47).

The tag peptide array in the present invention refers to a tag peptide array in which assuming that a combination of a tag peptide and a linker is one unit, one or plural units are repeatedly linked. The plural units mean two or more units. The number of repeated units can be increased or decreased as appropriate depending on the distance between a target site and a methylated or demethylated site, the kind of a methylase or demethylase, and the like, and may be, for example, 3 to 5.

DNA encoding a tag peptide array can be produced by adding a DNA sequence encoding a desired linker to DNA encoding a tag peptide that can be obtained from GenBank or the like. A method of obtaining the DNA by a molecular biological technique based on information on a DNA sequence is known. For example, the DNA can be artificially produced using an artificial gene synthesis technology known to those skilled in the art, and the method of obtaining the DNA is not limited. Those skilled in the art can also obtain an RNA sequence corresponding to the DNA sequence on the basis of information on the DNA sequence by using nucleotide sequence conversion software and the like.

(Fusion Protein of dCas9 and Tag Peptide Array, or RNA or DNA Coding Therefor)

DNA encoding a fusion protein of dCas9 and a tag peptide array can be produced by binding of DNA encoding the dCas9 defined above and DNA encoding the tag peptide array by using an optional method including a well-known gene manipulation method, and is not particularly limited. A DNA sequence encoding a selection marker may also be inserted into the DNA encoding the fusion protein. The selection marker enables cells into which the DNA encoding the fusion protein is introduced to be selected by cell sorting or the like. Examples of the selection marker include, but are not limited to, genes encoding fluorescent proteins such as GFP Ds-Red, and mCherry, and drug resistance genes such as puromycin resistance genes and neomycin resistance genes. The fusion protein or RNA encoding the fusion protein can be obtained by a known molecular biological technique using DNA encoding the fusion protein, and can be obtained by, for example, inserting DNA encoding the fusion protein into an appropriate expression vector and expressing the protein or the RNA.

(Tag Peptide-Binding Portion)

As the tag peptide-binding portion, an anti-tag peptide (peptide epitope) antibody, the large fragment of a split protein, or the like can be used depending on the kind of tag peptide, as described above. The anti tag peptide antibody means an antibody that specifically recognizes a tag peptide. The anti-tag peptide antibody includes polyclonal antibodies and monoclonal antibodies. The monoclonal antibodies include monoclonal antibodies, the fragments of monoclonal antibodies, f(ab')$_2$ antibodies, F(ab') antibodies, short-chain antibodies (scFv), diabodies, and minibodies. DNA encoding the anti-tag peptide antibody can be obtained by a known molecular biological technique, can be obtained by amplifying, for example, a commercially available plasmid such as Addgene plasmid 60904 by PCR, or may be artificially produced using an artificial gene synthesis technology known to those skilled in the art, and a method of obtaining the DNA is not limited. The anti-tag peptide antibody or RNA encoding the anti-tag peptide antibody can be obtained by inserting the DNA encoding the anti-tag peptide antibody into an appropriate expression vector and expressing the protein or the RNA.

(Methylase and Demethylase)

The methylase in the present is can be used without limitation as long as being an enzyme that catalyzes the methylation of an unmethylated site, and includes a methylase which is an enzyme that methylates a particular base on a DNA nucleotide sequence, and a methyltransferase which is an enzyme transferring a methyl group to a particular base, and more specific examples thereof include DNA methyltransferase 3 beta (DNMT3B), DNA methyltransferase 3 alpha (DNMT3A), and DNA methyltransferase 1 (DNMT1). The demethylase in the present invention can be used without limitation as long as being an enzyme catalyzing a series of reaction leading to the demethylation of a methylation site, and includes ten-eleven translocation 1 (TET1), ten-eleven translocation 2 (TET2), ten-eleven translocation 3 (TET3), and thymine-DNA glycosylase (TDG). These enzymes may be a portion or the whole of an enzyme protein. Preferred examples of the portion of the enzyme protein include a catalytic domain of an enzyme. Information on the sequence of DNAs encoding the enzymes can be obtained from GenBank and the like, and the DNAs can be produced from the cDNAs of target animals such as human by PCR. Alternatively, the DNAs encoding the enzymes may be artificially produced using an artificial gene synthesis technology known to those skilled in the art, and methods of obtaining the DNAs are not limited. The enzymes or RNAs encoding the enzymes can be obtained by inserting the DNAs into appropriate expression vector and expressing the proteins or RNAs.

(Fusion Protein of Tag Peptide-Binding Portion and Methylase or Demethylase, or RNA or DNA Encoding Fusion Protein)

DNA encoding a fusion protein of a tag peptide-binding portion such as an anti-peptide-epitope antibody and a methylase or demethylase can be produced by linking DNA encoding the tag peptide-binding portion defined above with DNA encoding a methylase or demethylase by using an optional method including a well-known gene manipulation method, and is not particularly limited. A DNA sequence encoding a selection marker may also be inserted into DNA encoding the fusion protein. The selection marker enables cells into which the DNA encoding the fusion protein is introduced to be selected by cell sorting or the like. Examples of the selection marker include, but are not limited to, genes encoding fluorescent proteins such as GFP, Ds-Red, and mCherry, and drug resistance genes such as puromycin resistance genes and neomycin resistance genes. When a DNA sequence encoding a selection marker is inserted into the DNA encoding the fusion protein of the dCas9 and the tag peptide array, a selection marker different from the selection marker may be inserted into DNA encoding a fusion protein of a tag peptide-binding portion and a methylase or demethylase. The fusion protein or RNA encoding the fusion protein can be obtained by a known molecular biological technique using DNA encoding the fusion protein, and can be obtained by, for example, inserting DNA encoding the fusion protein into an appropriate expression vector and expressing the protein or the RNA.

(Guide RNA (gRNA) or DNA Expressing Guide RNA)

The guide RNA (gRNA) in the present invention is a guide RNA in which a tracrRNA and a crRNA are artificially linked in a CRISPER method. By a known technique based on an RNA sequence described in Non Patent Literature 2 (p. 1698), DNA corresponding to the RNA sequence can be obtained as DNA expressing tracrRNA. For example the DNA may be artificially produced using an artificial gene synthesis technology known to those skilled in the art, and a method of obtaining the DNA is not limited. Alternatively, a plasmid that enables a desired gRNA to be expressed by inserting a DNA sequence corresponding to an arbitrary crRNA is commercially available (Addgene plasmid 41824 or the like) and may be therefore used. A sequence complementary to a DNA sequence within 1 kb from a desired site of methylation or demethylation is used as the crRNA. One kind of the gRNA is acceptable, or plural gRNAs each comprising different crRNAs may be used.

(All-In-One Vector)

The DNAs encoding the two fusion proteins described above may be further linked, resulting in DNA encoding a fusion protein of dCas9, a tag peptide array, a tag peptide-binding portion, and a methylase or demethylase, which may be incorporated into a vector and may be used. The vector comprising the DNA is referred to as an all-in-one vector. A linker may be inserted as appropriate into the DNA encoding the fusion protein. For example, when a 2A peptide derived from a virus is inserted as a linker between a fusion protein (regarded as a component 1) of dCas9 and a tag peptide array and a fusion protein (regarded as a component 2) of a tag peptide-binding portion and a methylase or demethylase, the 2A peptide is cleaned by the 2A peptidase in a cell, and therefore, the components 1 and 2 are prevented from being linked and expressed as two separated proteins. The all-in-one vector may also include a gRNA.

Examples of vectors composing desired genes in the present invention include a vector that can be replicated in a eukaryotic cell, a vector which maintaining an episome, and a vector incorporated into a host cell genome, and viral vectors are preferred, and adenovirus vectors, lentiviral vectors, and adeno-associated virus vectors are more preferred. Such a vector may include a selection marker. "Selection marker" refers to a genetic element which provides a selectable phenotype to a cell into which the selection marker is introduced, and is commonly a gene of which a gene product imparts resistance to an agent that inhibits cell proliferation or kills or wounds a cell. Specific examples thereof include Neo gene, Hyg gene, hisD gene, Gpt gene, and Ble gene. Examples of a drug useful for selecting the presence of the selection marker include G418 for Neo, hygromycin for Hyg, histidinol for hisD, xanthine for Gpt, and bleomycin for Ble.

(Transfection Into Cell)

Transfection of DNA, RNA, and a protein into a cell can be performed by using known optional means or may be performed using a commercially available reagent for transfection. For example, electroporation, Lipofectamine 2000 (Invitrogen), jetPRIME Kit (Polyplus-transfection), DreamFect (OZ Biosciences), GenePorter3000 (OZ Biosciences), Calcium Phosphate Transfection Kit (OZ Biosciences), and the like can be used for transfection of DNA. Electroporation, Lipofectamine 3000 (Invitrogen), RNAi Max (Invitrogen) MessengerMAX (Invitrogen), and the like can be used for transfection of RNA. Electroporation, Lipofectamine CRISPRMAX (Invitrogen), PULSin (Polyplus-transfection), Pro-DeliverIN (OZ Biosciences), BioPORTER Protein Delivery Reagent (Genlantis), and the like can be used for transfection of a protein. Transection into a cell may also performed by forming a complex of a gRNA and a fusion protein of dCas9 and a tag peptide array, in advance, and transfecting the complex into the cell. DNA, RNA, or a protein can also be introduced into a fertilized egg by microinjection or electroporation.

EXAMPLES

The present invention will be further described below with reference to non-limiting examples. In the present examples, GCN4 was used as a tag peptide. However, the GCN4 can be replaced with another tag peptide.

Example 1. Demethylation of Target Using TET1CD

<Plasmid Construction for Target Demethylation>

A dCas9-TET1 catalytic domain (CD) fusion protein expression vector (pCAG-dCas9TET1CD) was produced by fusing cDNA encoding codon-optimized S. pyogenes Cas9 (dCas9) as a catalytically inactive nuclease to a catalytic domain in the N-terminus of human TET1CD (System 1). A dCas9 fragment was amplified from Addgene plasmid 48240 by PCR. A TET1CD fragment was amplified from human cDNA by PCR.

Figure 1:
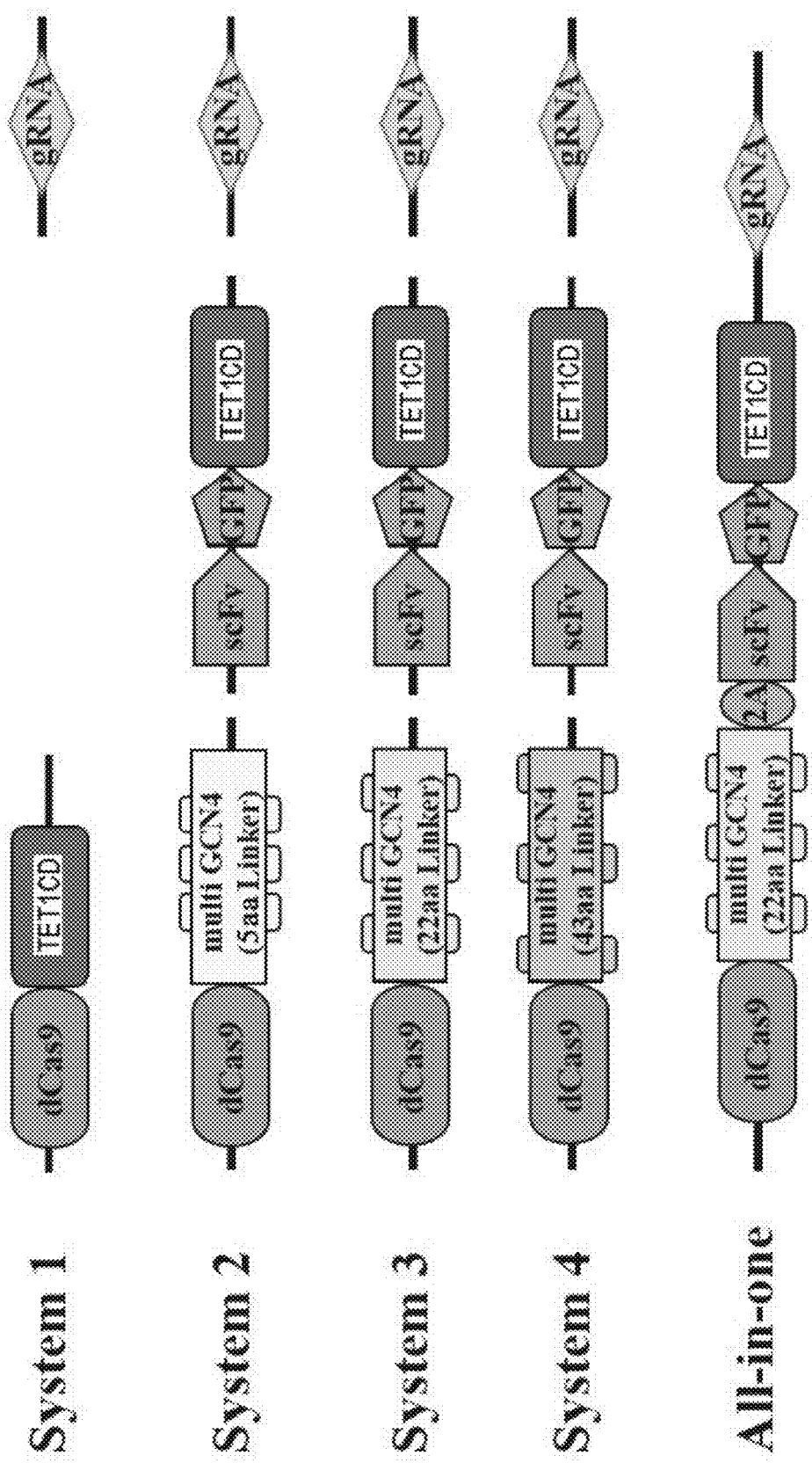
FIG. 1 is a view illustrating the components of transfected vectors (Example 1).

The dCas9 fragments of Systems 1 to 4 in FIG. 1 were amplified from Addgene plasmid 60903 by PCR. The amino acid sequence of used GCN4 was EELLSKNYHLENEVARLKK (SEQ ID NO: 1). Linker sequences between GCN4 tire GSGSG (SEQ ID NO: 2: System GSGSGGGSGSGSGGGSGSGGSGSG (SEQ ID NO 3: System 3), and GSGSGCSGSGGGSGSGGGSGSGGS GGGSGGGSGSGGGSGSGGGSGSG (SEQ ID NO: 4: System 4). A GFP fragment was amplified from Addgene plasmid 60904. An ScFv fragment was also amplified from Addgene plasmid 60904. All the fusion proteins were expressed under the control of a CAG promoter. An all-in-one vector was produced by fusing a 2A peptide (SEQ ID NO: 5: GSGATNFSLLKQAGDVEENPGP) into between the components 1 and 2 of System 3. Vector sequences are shown in SEQ ID NOS. 6 to 11 (which are System 1 (pCAG-dCas9TET1CD), dCas9-GCN4 fusion protein of System 2 (pCAG-dCas9-10xGCN4_v4), scFv-TET1CD fusion protein of Systems 2 to 4 (pCAG-scFvGCN4sfGFPTET1CD), dCas9-GCN4 fusion protein of System 3 (pCAG-dCas9-5xPlat2AflD, dCas9-GCN4 fusion protein of System 4 (pCAG-dCas9-3.5xSuper), and all-in-one vector (pPlatTET-gRNA2), respectively).

<Construction of gRNA>

A RNA vector for Gfap or H19 was produced by inserting a target sequence into Addgene plasmid 41834. Cloning was performed by Gibson assembly system via the linearization of an AflII site and the insertion of a gRNA fragment.

Target sequences are set forth in Table 1.

TABLE 1

Target Sequence

| Target Name | Target Sequence | Methylation-Sensitive site around Target |
|---|---|---|
| Gfap_1 | ATAGACATAATGGTCAGGGGTGG (SEQ ID NO: 12) | Gfap STAT3-binding site |
| Gfap_2 | GGATGCCAGGATGTCAGCCCCGG (SEQ ID NO: 13) | Gfap STAT3-binding site |
| Gfap_3 | ATATGGCAAGGGCAGCCCCGTGG (SEQ ID NO: 14) | Gfap STAT3-binding site |
| H19DMR_1 | GTGGGGGGCTCTTTAGGTTTGG (SEQ ID NO: 14) | H19DMR CTCF-binding site 1 |
| H19DMR_2 | ACCCTGGTCTTTACACACAAAGG (SEQ ID NO: 16) | H19DMR CTCF-binding site 2 |
| H19DMR_3 | GAAGCTGTTATGTGCAACAAGGG (SEQ ID NO: 17) | H19DMR CTCF-binding site 3 |
| H19DMR_4 | CAGATTTGGCTATAGCTAAATGG (SEQ ID NO: 18) | H19DMR CTCF-binding site 4 |

The underlines show PAM sequences.

Unrelated gRNA Sequence

| Target Name | gRNA Sequence |
|---|---|
| UR_1 | CCATTATTGCATTAATCTGA (SEQ ID NO: 19) |
| UR_2 | TAATGCAGCCAGAAAATGAC (SEQ ID NO: 20) |
| UR_3 | TCAGGGATCAAATTCTGAGC (SEQ ID NO: 21) |

<Cell Culture>

Embryonic stem cells (ESCs) were cultured in Dulbecco's modified Eagle's medium-high-concentration glucose (D6429-500 ML, Sigma) to which 1% FBS, 17.5% KSR100 (10828028, Gibco), 0.2% of 2-mercaptoethanol (21985-023, Gibco), and 1×10³ unit/mL (ESG1107, Millipore) of ESGRO mLIF were added under 37° C. and 5% $CO_2$. The ESCs were transfected using Lipofectamine 2000 (Invitrogen) according to an attached protocol, and the cells were collected 48 hours after the transfection and directly used for an assay and a sort by FACSAriaII (BD Biosciences).

<DNA Methylation Analysis>

Genomic DNA was treated using Epitect Plus DNA Bisulfite Kit (QIAGEN) according to an attached instruction. The modified DNA was amplified using the following PCR primers in Table 2.

TABLE 2

PCR Primer Sequence for Bisulfite Sequence

| Primer Name | Primer Sequence | Methylation-Sensitive Site around Target |
|---|---|---|
| GfapSTAT3-B3 | TTGGTTAGTTTTTAGGATTTTTTTT (SEQ ID NO: 22) | Gfap STAT3-binding site (ES) |
| GfapSTAT3-B4 | AAAACTTCAAACCCATCTATCTCTTC (SEQ ID NO: 23) | |
| H19DMR-B1 | AAGGAGATTATGTTTTATTTTTGGA (SEQ ID NO: 24) | CTCF-binding site 1 |
| H19DMR-B2 | AAAAAAACTCAATCAATACAATCC (SEQ ID NO: 25) | |
| Gfap_O1B1 | TTGTAAAGGTAGGATTAATAAGGGAATT (SEQ ID NO: 26) | Gfap off-target site 1 |
| Gfap_O1B2 | AAAAAAAACCCTTCAAAAAAAATCTA (SEQ ID NO: 27) | |
| Gfap_O2B1 | TTATTATTTATATTTGGAGGGAGGG (SEQ ID NO: 28) | Gfap off-target site 2 |
| Gfap_O2B2 | ATTACACCAAAAAATTTTAAAAAC (SEQ ID NO: 29) | |
| Gfap_O3B1 | TTTAAATTTTTTTATGTGAATATGG (SEQ ID NO: 30) | Gfap off-target site 3 |

TABLE 2-continued

PCR Primer Sequence for Bisulfite Sequence

| Primer Name | Primer Sequence | Methylation-Sensitive Site around Target |
|---|---|---|
| Gfap_O3B2 | AAACATTTAATTCATTAATACACAC (SEQ ID NO: 31) | |

The percentages of the demethylation of the STAT3 site of Gfap and the m1 to m4 sites of H19 were determined by Combined Bisulfite Restriction Analysis (COBRA). The fragments amplified using the primers in Table 3 were cleaved with restriction enzymes having recognition sites in the sites and set forth in Table 3 below and subjected to polyacrylamide gel electrophoresis.

TABLE 3

COBRA Primer Sequence

| primer name | primer sequence | Restriction enzyme | methylation sensitive site near the targets |
|---|---|---|---|
| GfapSTAT3-B1 | GTTGAAGATTTGGTAGTGTTGAGTT (SEQ ID NO: 32) | Hpy188III | Gfap STAT3-binding site |
| GfapSTAT3-B2 | TAAAACATATAACAAAAACAACCCC (SEQ ID NO: 33) | | |
| H19DMR-B1 | AAGGAGATTATGTTTTATTTTTGGA (SEQ ID NO: 24) | BstUI | H19DMR CTCF-binding site 1 |
| H19DMR-B2 | AAAAAAACTCAATCAATTACAATCC (SEQ ID NO: 25) | | |
| H19DMR-B1 | AAGGAGATTATGTTTTATTTTTGGA (SEQ ID NO: 24) | RsaI | H19DMR CTCF-binding site 2 |
| H19DMR-B2 | AAAAAAACTCAATCAATTACAATCC (SEQ ID NO: 25) | | |
| H19DMR-B3 | GGGTTTTTTTGGTTATTGAATTTTAA (SEQ ID NO: 34) | BstUI | H19DMR CTCF-binding site 3 |
| H19DMR-B4 | AATACACACATCTTACCACCCCCTATA (SEQ ID NO: 35) | | |
| H19DMR-B5 | TTTTTGGGTAGTTTTTTTAGTTTTG (SEQ ID NO: 36) | BstUI | H19DMR CTCF-binding site 4 |
| H19DMR-B6 | ACACAAATACCATAATCCCTTTATTAAAC (SEQ ID NO: 37) | | |

The methylation was calculated as the ratio of cleaved DNA by densitometry analysis of a gel stained with ethidium bromide. In each assay, the methylation of cells transfected with a control vector (empty gRNA vector) was defined as 100% methylation (0% demethylation), and the demethylation of each sample was standardized by the control using the following Numerical Formula 1.

Demethylation of sample (%)=methylation of control−methylation of sample)/methylation of control×100        Numerical Formula 1

Bisulfite sequencing was carried out for the methylation analysis and off-target analysis of a peripheral region. The amplified fragment was ligated into a TOPO vector (Invitrogen), and sequencing of at least 14 clones was carried out. The sequencing was analyzed by a methylation analysis tool referred to as QUantification tool for Methylation Analysis (QUMA). Statistical significance between two groups of all sets in CpG sites was evaluated using Mann-Whitney U test (also referred to as Wilcoxon matched pairs signed ranks test is called) used for a test of nonparametric statistical significance.

<Results>

First, a simple design which was a direct fusion protein of inactivated Cas9 nuclease (dCas9) and TET1 was produced for methylation treatment. TET1 has a catalytic domain preserved in a C-terminus, and this domain has higher catalytic activity than that of a full-length protein. Therefore, the TET1 catalytic domain (TET1CD) was fused to dCas9 having inactive catalytic action (System 1 in FIG. 1).

A cytosine residue in a STAT3-binding site located upstream of a gene encoding glial fibrillary acidic protein (GFAP) which is an astrocyte-specific marker was used as a target. The site is methylated in many cell types excluding astrocytes, and the demethylation of the site plays an important role in differentiation of neural precursor cells (NPCs) into astrocytes. Three targets around the STAT3-binding site were designed (FIG. 2a), and a gRNA vector for the targets was produced. The gRNA vector was transiently introduced, together with a dCAS9-TET1CD fusion protein expression vector (pCAG-dCas9TET1CD), into embryonic stem cells (ESCs). The methylation of the STAT3-binding site was analyzed by Combined Bisulfite Restriction Analysis (COBRA). In each assay, the methylation of cells into which a gene was introduced together with a control vector (empty gRNA vector) was defined as 0% demethylation (100% methylation), and the demethylation of each sample was standardized by the control.

Figure 2:
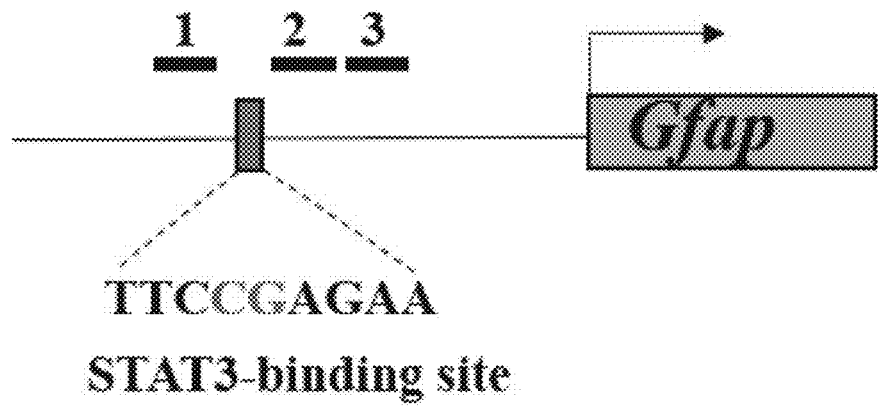
FIG. 2 Section (a) at FIG. 2 is a view illustrating a STAT3 banding site and a mouse Gfap site. The STAT3 binding site has a methylation-sensitive CpG site (CG in TTCCGA-GAA)). Targets 1 to 3 used as gRNAs (Gfap1-3) are indicated by black thick bars. Section (b) of FIG. 2 is a graph illustrating the demethylation activity dCas9 (system 1) directly bound to a TET1 catalytic domain (TET1CD) in which gRNAs targeting Gfap1-3 are used. The ordinate represents a value calculated by the Numerical Formula in the table (the same the Numerical Formula 1 shown below) as a standardized demethylation percentage (%).
Figure 2:
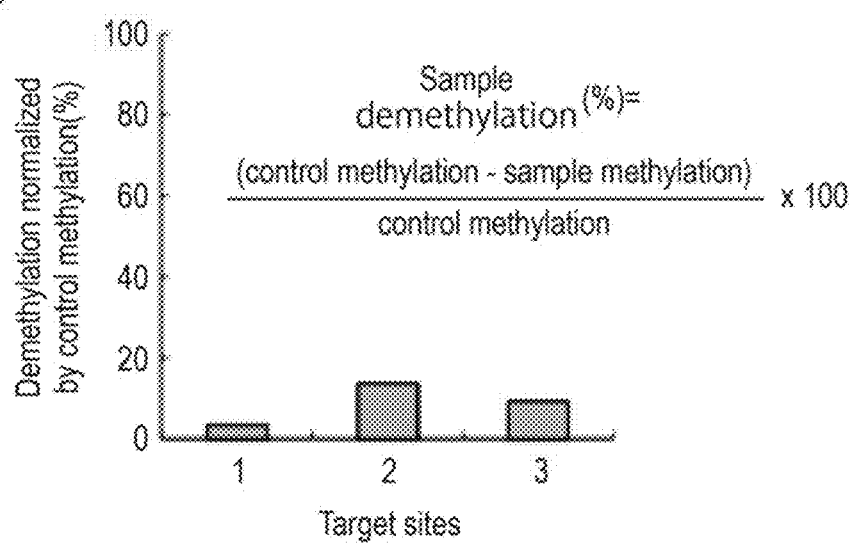

In the STAT3 site, the three gRNAs, Ffap1, Gfap2 and Gfap3, showed demethylations of 3%, 14%, and 9%, respectively (FIG. 2b). In contrast, the unrelated gRNAs (UR1, UR2, and UR3) showed no demethylation. Thus, this simple system induced gRNA-dependent specific demethylation, but the degree of the demethylation was shown to be at most 14%.

Then, an attempt to amplify a demethylation ability was made using dCas9 fused in a repeating peptide sequence in order to recruit plural copies of the antibody fused TET1 hydroxylase catalytic domain (FIG. 3a). For the demethylation of the Gfap STAT3 site, an expression vector of Gfap2gRNA, dCas9 having 10 copies of GCN4 peptides, and a GCN4 peptide antibody (scFv)-superfolder green fluorescent protein (sfGFP)-TET1CD fusion protein was used in ESCs (System 2 in FIG. 1). However, the use of this System 2 did not allow the degree of the demethylation to be improved (FIG. 4a).

Figure 3B:
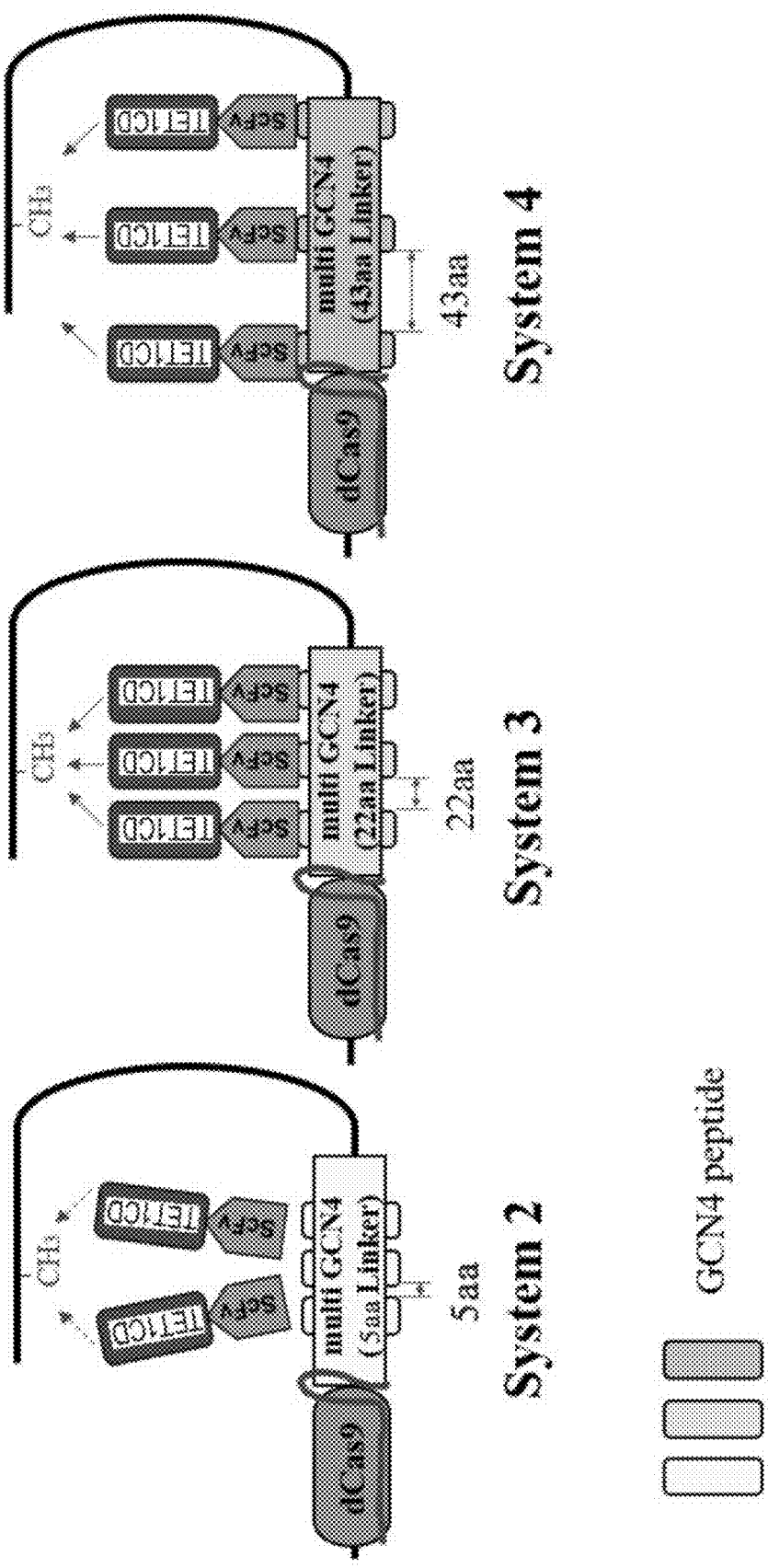
FIG. 3B is a view illustrating a case in which the length of a linker separating each GCN4 peptide epitope fused with dCas9 is too short (left), a case in which the length is appropriate (center), and a case in which the length is too long (right).

The length of a linker by which the sequence of a GCN4 peptide epitope comprising 19 amino acids was separated was examined in order to investigate the reason why System 2 failed to improve the degree of the demethylation. If the length of the linker is too short, it is considered that for the antibody-TET1CD fusion protein, a space for approaching and binding to the GCN4 peptide sequence is too narrow, and therefore, demethylation activity becomes insufficient. If the length of the linker is too long, it is considered that the antibody-TET1CD fusion protein is incapable of approaching a target methylated site (FIG. 3b). The length of the linker of System 2 was 5 amino acids (System 2 in FIG. 1).

A dCas9-GCN4 fusion protein having a linker of which the length was 22 amino acids (System 3 in FIG. 1) and a dCas9-GCN4 fusion protein having a linker of which the length was 43 amino acids (System 4 in FIG. 1) were produced, and the demethylation activities thereof were compared. Because of technological limitation in a synthetic gene technology, the numbers of copies of GCN4 peptides having a linker of which the length was 22 amino acids and a linker of which the length was 43 amino acids were decreased to 5 and 4, respectively. In spite of the decreases in the numbers of the copies of the GCN4 peptides, the linker of which the length was 22 amino acids showed a best demethylation of 43%. The linker of which the length was 44 amino acids showed a second highest activity, and the linker, as a prototype, of which the length was 5 amino acids showed the lowest activity (FIG. 4a).

These results suggested that the length of a linker by which each GCN4 peptide unit sequence fused with dCas9 is separated is more important for demethylation activity than the number of copies of GCN4. The demethylation activity was prominently improved by increasing the length of the linker from 5 amino acids to 22 amino acids. This is considered to be because the 22 amino acids have a width enough for the antibody-TET1CD fusion protein to approach a peptide sequence. In contrast, the linker of which the length was 43 amino acids was considered to be long for the antibody-TET1CD fusion protein to approach a methylated site which was a target.

Figure 4:
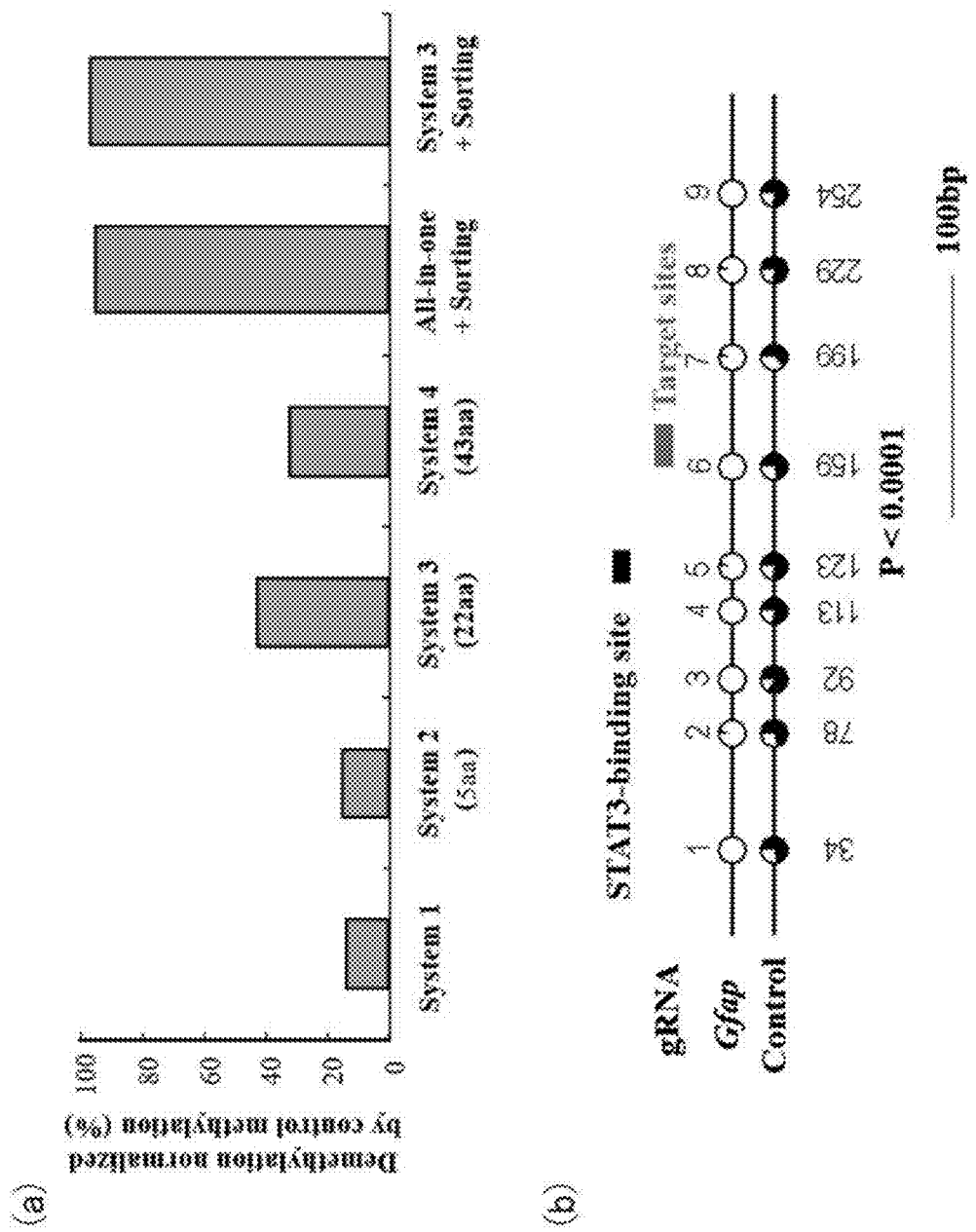
FIG. 4 In section (a) of FIG. 4, the ordinate represents a value calculated by the Numerical Formula 1 shown below as a standardized demethylation percentage (%). The abscissa represents the system of a vector used and the presence or absence of sorting. Target 2 of Gfap was used as a gRNA. Section (b) of FIG. 4 is a view illustrating the methylation in the peripheries of target sites. ESCs transfected with gRNAs targeting system 3 and Gfap2 or a control gRNA were sorted by GFP, and methylation was analyzed by bisulfite sequencing. A black-and-white-style circle represents the percentage of the methylation, and the black represents methylation while the white represents unmethylation. The number under the circle represents each position. Statistical significances between all CpG site sets in the two groups (Gfap and control) were evaluated by Mann-Whitney U test.

Cells into which GFP expression vector was introduced were selected using fluorescence activated cell sorting (FACS) for the purpose of further improving demethylation efficiency. For this purpose, an all-in-one vector comprising a gRNA, dCas9 comprising the GCN4 sequence of System 3, and an antibody-sfGFP-TET1CD fusion protein was produced (FIG. 1). The all-in-one introduced ESCs sorted by GFP showed roughly complete demethylation (FIG. 4). The ESCs into which System 3 was introduced and which was sorted by GFP also unexpectedly showed roughly complete demethylation (FIG. 4). Complete demethylation in a target region was achieved by the promotion of the demethylation ability and the sorting technology.

Figure 5:
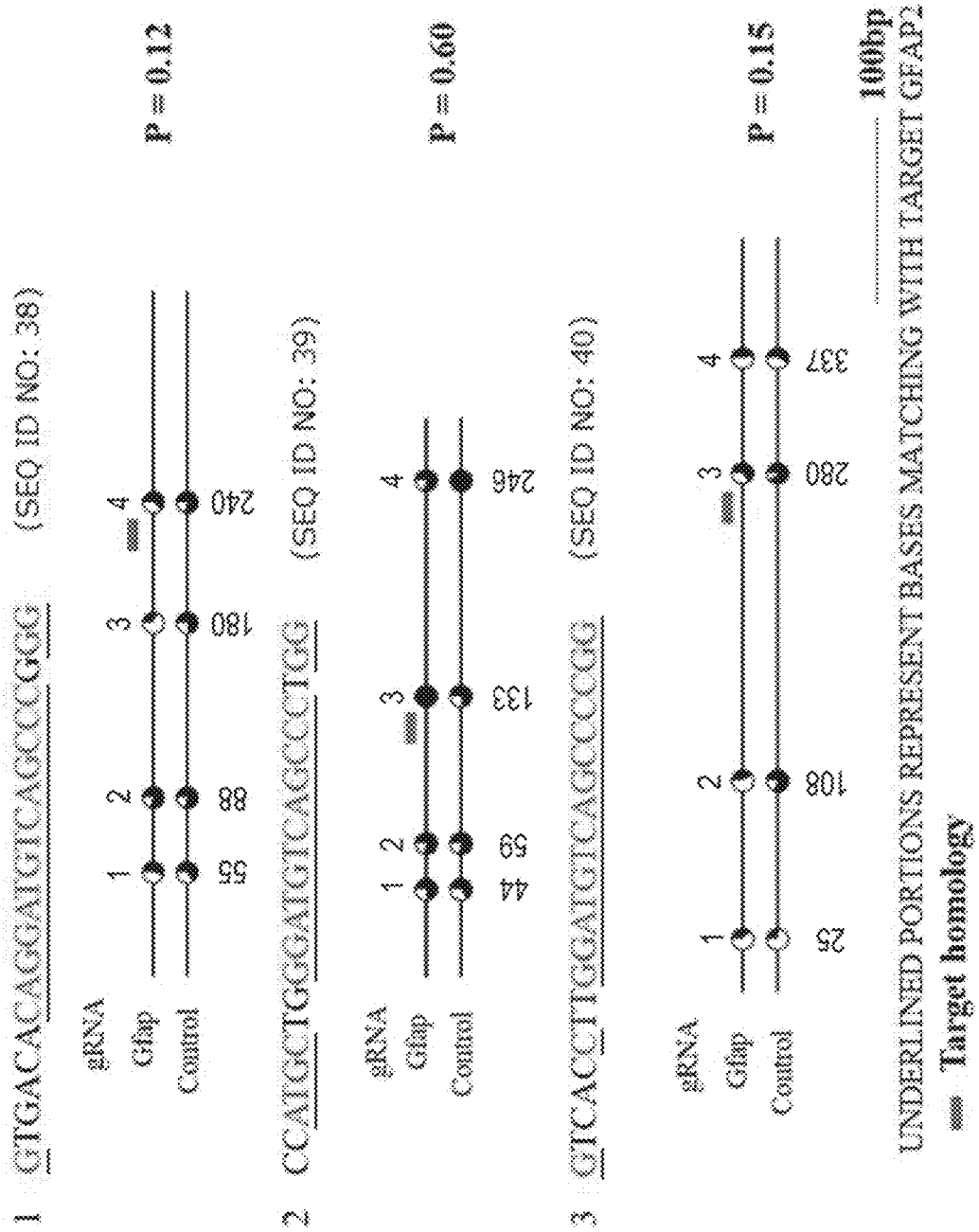
FIG. 5 is a view illustrating the methylation in the peripheries of off-target sites 1 to 3 of a gRNA targeting Gfap2. ESCs transfected with gRNAs targeting system 3 and Gfap2 were sorted by GFP, and the methylation of the peripheries of the off-target sites 1 to 3 was analyzed by bisulfite sequencing. A black-and-white-style circle represents the percentage of the methylation, and the black represents methylation while the white represents unmethylation. The number under the circle represents each position. Statistical significances between all CpG site sets in the two groups (Gfap and control) were evaluated by Mann-Whitney U test. The underlined portions of the sequences represent portions in which Gfap2 targets and nucleotide sequences match with each other.

Then, the range of the demethylation of a used sorted sample from a target site was investigated by bisulfite sequencing. The demethylation occurred even at a site located at least 100 bp or more apart from the target site (FIG. 4b). Investigation of off-target activity by bisulfite sequencing using the same sample resulted in no observation of noticeable off-target activity (FIG. 5).

Figure 6:
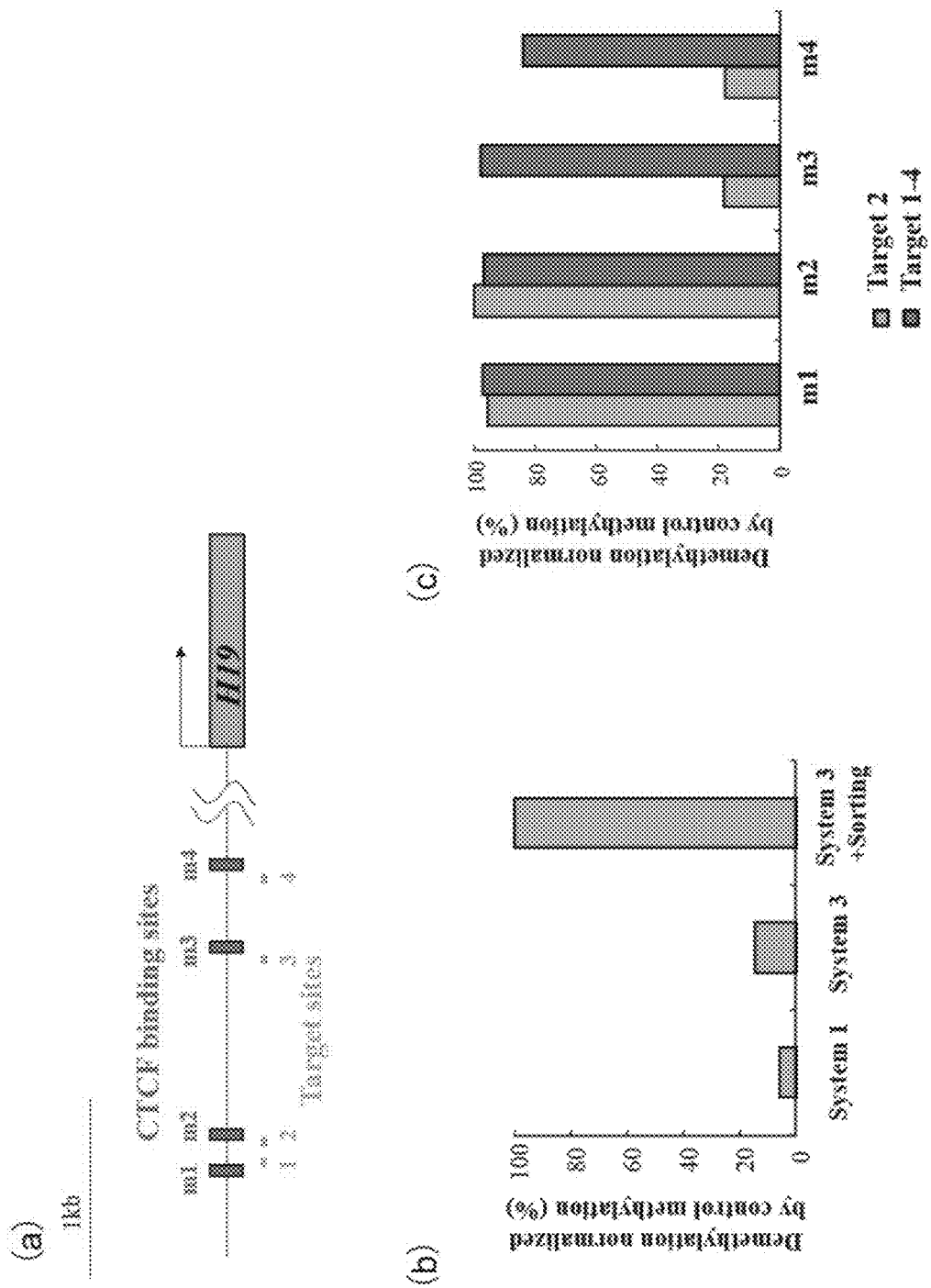
FIG. 6 Section (a) of FIG. 6 illustrates CTCF binding sites and a mouse H19 site. The CTCF binding sites have methylation-sensitive CpG sites (m1 to m4). Sites 1 to 4 used in the targets of gRNAs are illustrated under vertically long bars representing m1 to m4. Section (b) of FIG. 6 illustrates the demethylation of m2 in the CTCF binding sites using systems 1 and 3, and system 3+sorting. The ordinate represents a value calculated by the Numerical Formula 1 shown below as a standardized demethylation percentage (%). The abscissa represents the system of a vector used and the presence or absence of sorting. Section (c) of FIG. 6 is a graph illustrating the demethylation is the CTCF binding sites (m1 to m4) in the case of using system 3+sorting. Left and right bars in each site of m1 to m4 represent demethylation in the case of using the target site 2 as a gRNA and demethylation in the case of using all the gRNAs of the target sites 1 to 4 together, respectively. The ordinate represents a value calculated by the Numerical Formula 1 shown below as a standardized demethylation percentage (%).

Then, a similar experiment was conducted using a differential methylation region (DMR) of H19 as a paternal methylated imprinting gene. The DMR of H19 includes four methylation-sensitive CTCF binding sites (m1 to m4), which are important for adjusting H19 imprinting (FIG. 6a). A gRNA (H19DMR2) targeting m2 was introduced, together with dCas9-TET1CD or System 3, into ESCs. The cells into which System 3 bad been introduced and which were subjected to cell sorting after the introduction were also produced.

As a result, noticeable improvement in methylation in System 3 was observed in comparison with dCas9-TET1CD. Complete demethylation was observed at the m2 site in the cells sorted by GFP (FIG. 6b). Further analyzation of the cells sorted by GFP for the methylation of a peripheral region showed complete demethylation at the m1 site located 200 bp apart from the target region (FIG. 6c). In contrast, the slight demethylation of the m3 and m4 sites located 1 kb or more apart from the target site merely occurred (FIG. 6c), and it was suggested that the effect of the demethylation was not greater than that of a site located 1 kb or more apart. In order to test the possibility of targeting of plural of sites, the gRNAs of m1 to m4 were introduced together with System 3 (H19DMR1-4). As a result, roughly complete demethylation was observed in all of the four sites (m1 to m4) in the cells sorted by GFP (FIG. 6c). This showed that plural sites can be demethylated by using plural gRNAs.

Example 2. Methylation of Target Using Dnmt3b

Figure 7:
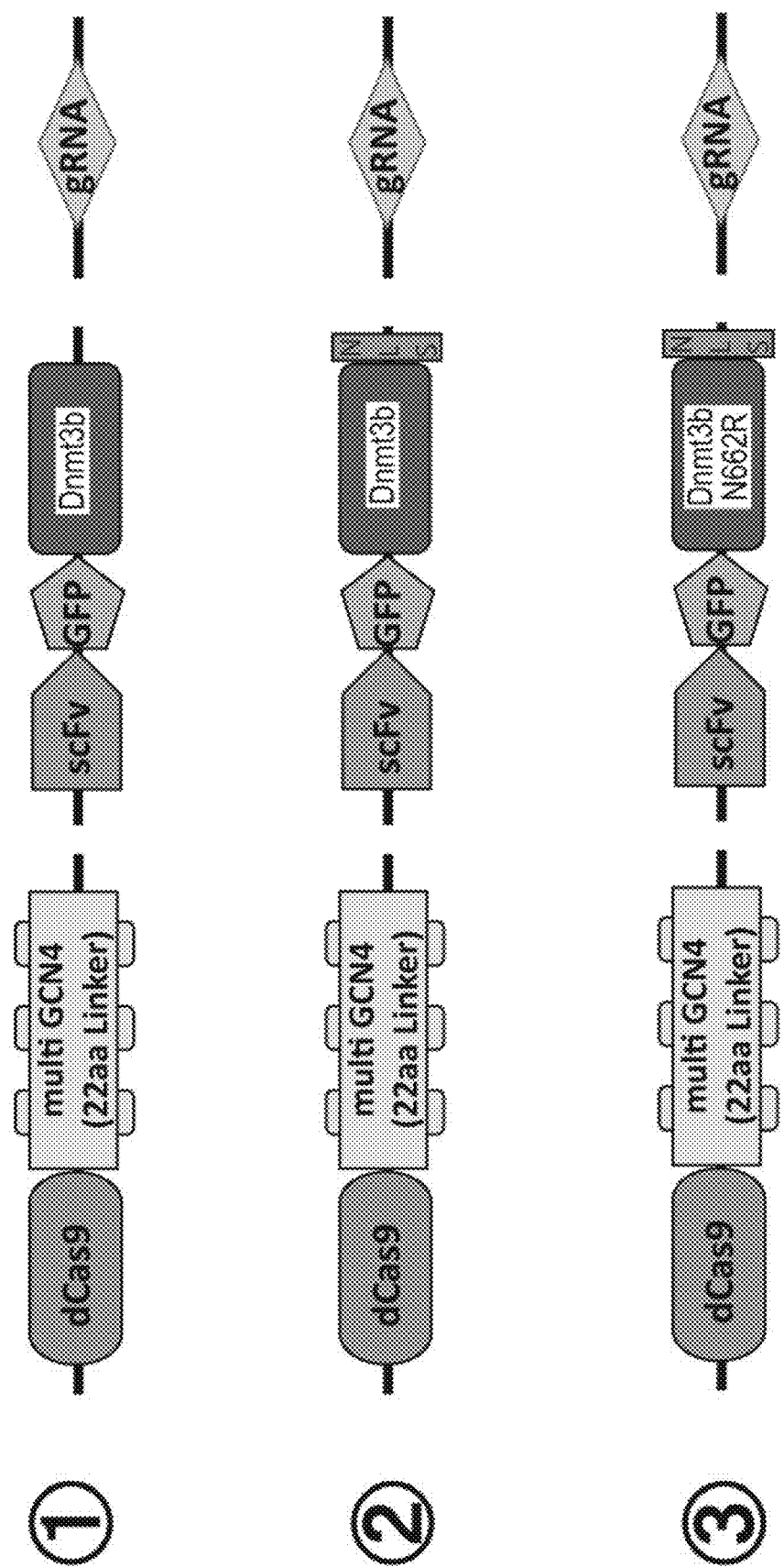
FIG. 7 is a view illustrating the components of transfected vectors (Example 2).

The m2 site of H19 was methylated using System 3 (linker 22aa) in order to introduce methylation into a target. Experiments were conducted using (1) Dnmt3b, (2) Dnmt3bNLS, and (3) Dnmt3bNLS_N662R instead of TET1CD (FIG. 7). (1) is a De novo methylase Dnmt3b, (2) is obtained by adding NLS (nuclear localization signal) to the C terminus of the Dnmt3b of (1), and (3) is obtained by changing the 662nd amino acid of (2) from asparagine (N) to arginine (R). This amino acid substitution has been reported to improve methylation activity (Shen L et al. below). The plasmids used are as follows.

(1) Dnmt3b: pCAG-scFvGCN4sfGFPDnmt3bF (SEQ ID NO: 41)
(2) Dnmt3bNLS: pCAG-scFvGCN4sfGFPDnmt3bFNLS (SEQ ID NO: 42)
(3) Dnmt3bNLS_N662R: pCAG-scFvGCN4sfGFPDnmt3bS1 (SEQ ID NO: 43)

Figure 8:
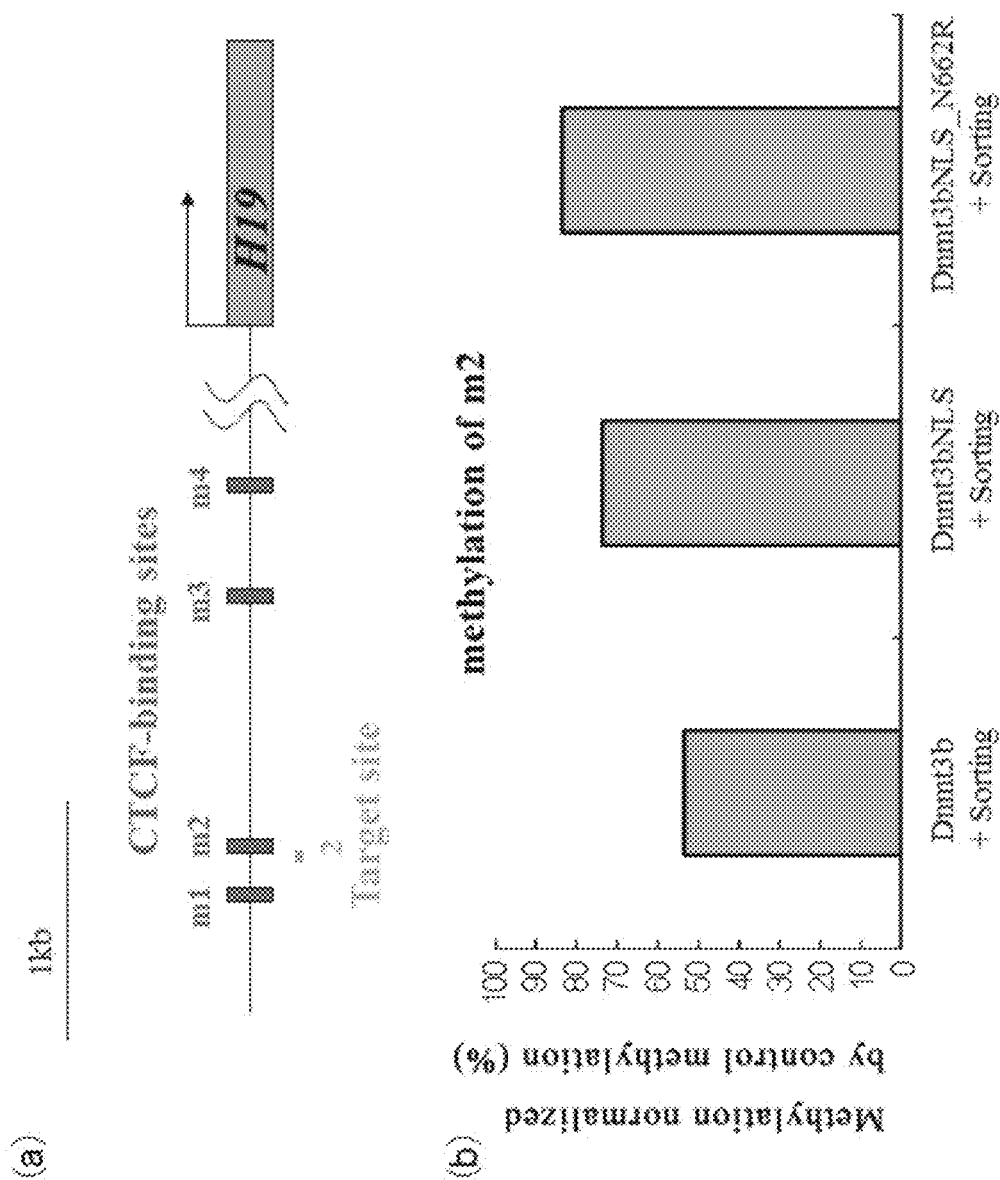
FIG. 8 Section (a) of FIG. 8 illustrates CTCF binding sites and a mouse H19 site. The CTCF binding sites have methylation-sensitive CpG sites (m1 to m4). In Example 2, m2 was used as a target. Section (b) of FIG. 8 illustrates, the methylation of m2 in the CTCF binding sites using system 3+sorting. The ordinate represents a value calculated by the following Numerical Formula 2 as a standardized methylation percentage (%).

Only cells into which genes were introduced and which emitted fluorescence were isolated based on fluorescence of GFP by a cell sorter 2 days after introduction of these systems of (1) to (3) into ES cells, and the methylation of the m2 of H19 was examined in a manner similar to that in the demethylation. The methylation was calculated as a methylation (%) standardized by a control, as shown in Numerical Formula 2. As a result, the methylations of the targets were (1) 54%, (2) 74%, and (3) 84%, revealing that methylation efficiency in the case of adding NLS was higher than that in the case of only Dnmt3b, and methylation efficiency in the case of the amino acid substitution of N662R was further higher (FIG. 8).

Methylation (%) standardized by control=(methylation of sample−methylation of control/methylation of control×100   Numerical Formula 2

REFERENCES

Shen L, Gao G, Mann Y, Zhang; H, Ye Z, Huang S, Huang J, Kang J. A single amino acid substitution confers enhanced methylation activity of mammalian Dnmt3b on chromatin DNA, Nucleic Acids Res. 38:6054-6064, 2010, doi: 10.1093/nar/gkq456.
SEQ ID NO: 1: GCN4
SEQ ID NO: 2: linker 5
SEQ ID NO: 3: linker 22
SEQ ID NO: 4: linker 43
SEQ ID NO: 5: 2A peptide
SEQ ID NO: 6: pCAG-dCas9TET1 CD
SEQ ID NO: 7: pCAG-dCas9-10×GCN4_v4
SEQ ID NO: 8: pCAG-scFvGCN4sfGFPTET1CD
SEQ ID NO: 9: pCAG-dCas9-5xPlat2AflD
SEQ ID NO: 10: pCAG-dCas9-3.5xSuper
SEQ ID NO: 11: pPlatTET-gRNA2
SEQ ID NO: 12: Gfap_1
SEQ ID NO: 13: Gfap_2
SEQ ID NO: 14: Gfap_3
SEQ ID NO: 15: H19DMR_1
SEQ ID NO: 16: H19DMR_2
SEQ ID NO: 17: H19DMR_3
SEQ ID NO: 18: H19DMR_4
SEQ ID NO: 19: UR_1
SEQ ID NO: 20: UR_2
SEQ ID NO: 21: UR_3
SEQ ID NO: 22: GfapSTAT3-B3
SEQ ID NO: 23: GfapSTAT3-B4
SEQ ID NO: 24: G19DMR-B1
SEQ ID NO: 25: H19DMR-B2
SEQ ID NO: 26: Gfap_O1B1
SEQ ID NO: 27: Gfap_O1B2
SEQ ID NO: 28: Gfap_O2B1
SEQ ID NO: 29: Gfap_O2B2
SEQ ID NO: 30: Gfap_O3B1
SEQ ID NO: 31: Gfap_O3B2
SEQ ID NO: 32: GfapSTAT3-B1
SEQ ID NO: 33: GfapSTAT3-B2
SEQ ID NO: 34: H19DMR-B3
SEQ ID NO: 35: H19DMR-B4
SEQ ID NO: 36: H19DMR-B5
SEQ ID NO: 37: H19DMR-B6
SEQ ID NO: 38: off target 1
SEQ ID NO: 39: off target 2
SEQ ID NO: 40: off target 3
SEQ ID NO: 41: pCAG-scFvGCN4sfGFPDnmt3bF
SEQ ID NO: 42: pCAG-scFvGCN4sfGFPDnmt3bFNLS
SEQ ID NO: 43: pCAG-scFvGCN4sfGFPDnmt3bS1
SEQ ID NO: 44: tag peptide GVKESLV
SEQ ID NO: 45: GS linker
SEQ ID NO: 46: GS linker
SEQ ID NO: 47: GS linker

INDUSTRIAL APPLICABILITY

The methylation of a particular gene can be controlled according the present invention. As a result, model cells and animals with diseases (epigenome diseases) occurring due to DNA methylation abnormality, such as cancers and imprinting diseases, can be produced. In addition, virus vectors and other delivery systems can be used for treatment of the diseases. In production of iPS cells, the iPS cells can be effectively produced by demethylating and activating a pluripotent gene such as Oct-4 according to the present invention.

What is claimed is:

1. A DNA methylation editing kit comprising:
   (1) a first fusion protein comprising (i) inactivated CRISPR-associated endonuclease Cas9 (dCas9) having no nuclease activity and (ii) a tag peptide array comprising a plurality of tag peptides and peptide linkers which consist of 15 to 50 amino acids and link said tag peptides, or an RNA or DNA coding the first fusion protein, wherein the tag peptides are peptide epitopes, and the tag peptide-binding portion is an anti-peptide-epitope antibody, and wherein the peptide epitopes are general control non-derepressible 4 (GCN4) peptide epitopes, and the anti-peptide-epitope antibody is an anti-GCN4 peptide epitope antibody;
   (2) a second fusion protein(s) comprising a tag peptide-binding portion and a methylase or demethylase, or an RNA(s) or DNA(s) coding the second fusion protein, wherein the demethylase is a catalytic domain of ten-eleven translocation 1 (TET1CD) and the methylase is DNA methyltransferase 3 beta (DNMT3B); and
   (3) a guide RNA(s) (gRNA(s)) comprising a sequence complementary to a DNA sequence within 1 kb from a desired site of methylation or demethylation, or a DNA(s) expressing the gRNA(s).

2. The DNA methylation editing kit according to claim 1, wherein the antibody is a single-chain antibody (scFv).

3. The DNA methylation editing kit according claim 1, wherein the linkers consist of 15 to 40 amino acids.

4. The DNA methylation editing kit according to claim 1, wherein the fusion proteins of the (1) and/or (2) further comprise a selection marker as a part of the fusion protein.

5. The DNA methylation editing kit according to claim 1, which contains plural gRNAs.

6. The DNA methylation editing kit according to claim 1, wherein all the DNAs of the (1) to (3) are contained in a single vector.

7. A set of vectors each comprising the following (1) to (3):
   (1) RNA(s) or DNA(s) encoding a first fusion protein wherein the first fusion protein comprising inactivated CRISPR-associated endonuclease Cas9 (dCas9) having no nuclease activity and a tag peptide array in which a plurality of tag peptides are linked by peptide linkers consisting of 15 to 50 amino acids;
   (2) RNA(s) or DNA(s) encoding a second fusion protein, wherein the second fusion protein(s) comprises a tag peptide-binding portion and a methylase or demethylase, wherein the demethylase is a catalytic domain of ten-eleven translocation 1 (TET1CD) and the methylase is DNA methyltransferase 3 beta (DNMT3B); and
   (3) a guide RNA(s) (gRNA(s)) comprising a sequence complementary to a DNA sequence within 1 kb of a desired site of methylation or demethylation, or a DNA(s) expressing the gRNA(s).

* * * * *

SEQUENCE LISTING

```
<160> NUMBER OF SEQ ID NOS: 47

<210> SEQ ID NO 1
<211> LENGTH: 19
<212> TYPE: PRT
<213> ORGANISM: Saccharomyces cerevisiae

<400> SEQUENCE: 1

Glu Glu Leu Leu Ser Lys Asn Tyr His Leu Glu Asn Glu Val Ala Arg
1               5                   10                  15

Leu Lys Lys

<210> SEQ ID NO 2
<211> LENGTH: 5
<212> TYPE: PRT
<213> ORGANISM: Artificial Sequence
<220> FEATURE:
<223> OTHER INFORMATION: linker 5

<400> SEQUENCE: 2

Gly Ser Gly Ser Gly
1               5

<210> SEQ ID NO 3
<211> LENGTH: 22
```

```
<212> TYPE: PRT
<213> ORGANISM: Artificial Sequence
<220> FEATURE:
<223> OTHER INFORMATION: linker 22

<400> SEQUENCE: 3

Gly Ser Gly Ser Gly Gly Ser Gly Ser Gly Ser Gly Gly Ser Gly Ser
1               5                   10                  15

Gly Gly Ser Gly Ser Gly
            20

<210> SEQ ID NO 4
<211> LENGTH: 43
<212> TYPE: PRT
<213> ORGANISM: Artificial Sequence
<220> FEATURE:
<223> OTHER INFORMATION: linker 43

<400> SEQUENCE: 4

Gly Ser Gly Ser Gly Gly Ser Gly Ser Gly Gly Ser Gly Ser Gly Gly
1               5                   10                  15

Ser Gly Ser Gly Gly Ser Gly Gly Ser Gly Ser Gly Gly Ser Gly Ser
            20                  25                  30

Gly Gly Ser Gly Ser Gly Gly Ser Gly Ser Gly
        35                  40

<210> SEQ ID NO 5
<211> LENGTH: 22
<212> TYPE: PRT
<213> ORGANISM: Artificial Sequence
<220> FEATURE:
<223> OTHER INFORMATION: 2A peptide

<400> SEQUENCE: 5

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 6
<211> LENGTH: 11427
<212> TYPE: DNA
<213> ORGANISM: Artificial Sequence
<220> FEATURE:
<223> OTHER INFORMATION: pCAG-dCas9TET1CD

<400> SEQUENCE: 6
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catgggtcga ggtgagcccc acgttctgct tcactctccc catctccccc cctccccac      420 ccccaatttt gtatttattt attttttaat tattttgtgc agcgatgggg gcggggggg      480 gggggcgcg cgccaggcgg ggcggggcg ggcgagggc gggcggggc gaggcggaga       540 ggtgcggcg cagccaatca gagcggcgcg ctccgaaagt ttcctttat ggcgaggcgg       600 cggcggcggc ggccctataa aaagcgaagc gcgcggcggg cgggagtcgc tgcgttgcct     660
```

```
tcgccccgtg ccccgctccg cgccgcctcg cgccgcccgc cccggctctg actgaccgcg    720
ttactcccac aggtgagcgg gcgggacggc ccttctcctc cgggctgtaa ttagcgcttg    780
gtttaatgac ggctcgtttc ttttctgtgg ctgcgtgaaa gccttaaagg gctccgggag    840 ggcccttttgt gcggggggga gcggctcggg gggtgcgtgc gtgtgtgtgt gcgtggggag    900
cgccgcgtgc ggcccgcgct gccccggcggc tgtgagcgct gcgggcgcgg cgcggggctt    960
tgtgcgctcc gcgtgtgcgc gagggggagcg cggccggggg cggtgccccg cggtgcgggg   1020
gggctgcgag gggaacaaag gctgcgtgcg gggtgtgtgc gtggggggggt gagcaggggg   1080 tgtgggcgcg gcgtcgggc tgtaaccccc ccctgcaccc ccctccccga gttgctgagc    1140
acggcccggc ttcgggtgcg gggctccgtg cggggcgtgg cgcggggctc gccgtgccgg   1200
gcggggggtg gcggcaggtg ggggtgccgg gcggggcggg gccgcctcgg gccggggagg   1260
gctcggggga ggggcgcggc ggccccggag cgccggcggc tgtcgaggcg cggcgagccg   1320
cagccattgc cttttatggt aatcgtgcga gagggcgcag ggacttcctt tgtcccaaat   1380
ctggcggagc cgaaatctgg gaggcgccgc cgcacccct ctagcgggcg cgggcgaagc   1440
ggtgcggcgc cggcaggaag gaaatgggcg gggagggcct tcgtgcgtcg ccgcgccgcc   1500
gtccccttct ccatctccag cctcggggct gccgcagggg gacggctgcc ttcgggggg   1560 acggggcagg gcggggttcg gcttctggcg tgtgaccggc ggctctagag cctctgctaa   1620
ccatgttcat gccttcttct ttttcctaca gctcctgggc aacgtgctgg ttgttgtgct   1680
gtctcatcat tttggcaaag aattctgcag tcgacggtac catgtaccca tacgatgttc   1740
cagattacgc ttcgccgaag aaaaagcgca aggtcgaagc gtccgacaag aagtacagca   1800
tcggcctggc catcggcacc aactctgtgg gctgggccgt gatcaccgac gagtacaagg   1860
tgcccagcaa gaaattcaag gtgctgggca acaccgaccg gcacagcatc aagaagaacc   1920
tgatcggagc cctgctgttc gacagcggcg aaacagccga ggccacccgg ctgaagagaa   1980
ccgccagaag aagatacacc agacggaaga accggatctg ctatctgcaa gagatcttca   2040
gcaacgagat ggccaaggtg gacgacagct tcttccacag actggaagag tccttcctgg   2100
tggaagagga taagaagcac gagcggcacc ccatcttcgg caacatcgtg gacgaggtgg   2160
cctaccacga gaagtacccc accatctacc acctgagaaa gaaactggtg gacagcaccg   2220
acaaggccga cctgcggctg atctatctgg ccctggccca catgatcaag ttccggggcc   2280
acttcctgat cgagggcgac ctgaaccccg acaacagcga cgtggacaag ctgttcatcc   2340
agctggtgca gacctacaac cagctgttcg aggaaaaccc catcaacgcc agcggcgtgg   2400
acgccaaggc catcctgtct gccagactga gcaagagcag acggctggaa atctgatcg   2460 cccagctgcc cggcgagaag aagaatggcc tgttcggcaa cctgattgcc ctgagcctgg   2520
gcctgacccc caacttcaag agcaacttcg acctggccga ggatgccaaa ctgcagctga   2580
gcaaggacac ctacgacgac gacctggaca acctgctggc ccagatcggc gaccagtacg   2640
ccgacctgtt tctggccgcc aagaacctgt ccgacgccat cctgctgagc gacatcctga   2700
gagtgaacac cgagatcacc aaggcccccc tgagcgcctc tatgatcaag agatacgacg   2760
agcaccacca ggacctgacc ctgctgaaag ctctcgtgcg gcagcagctg cctgagaagt   2820
acaaagagat tttcttcgac cagagcaaga acggctacgc cggctacatt gacggcggag   2880
ccagccagga agagttctac aagttcatca agcccatcct ggaaaagatg gacggcaccg   2940
aggaactgct cgtgaagctg aacagagagg acctgctgcg gaagcagcgg accttcgaca   3000
```

```
acggcagcat ccccaccag atccacctgg gagagctgca cgccattctg cggcggcagg    3060
aagattttta cccattcctg aaggacaacc gggaaaagat cgagaagatc ctgaccttcc    3120
gcatccccta ctacgtgggc cctctggcca ggggaaacag cagattcgcc tggatgacca    3180
gaaagagcga ggaaaccatc accccctgga acttcgagga agtggtggac aagggcgctt    3240
ccgcccagag cttcatcgag cggatgacca acttcgataa gaacctgccc aacgagaagg    3300
tgctgcccaa gcacagcctg ctgtacgagt acttcaccgt gtataacgag ctgaccaaag    3360
tgaaatacgt gaccgaggga atgagaaagc ccgccttcct gagcggcgag cagaaaaagg    3420
ccatcgtgga cctgctgttc aagaccaacc ggaaagtgac cgtgaagcag ctgaaagagg    3480
actacttcaa gaaaatcgag tgcttcgact ccgtggaaat ctccggcgtg gaagatcggt    3540
tcaacgcctc cctgggcaca taccacgatc tgctgaaaat tatcaaggac aaggacttcc    3600
tggacaatga ggaaaacgag gacattctgg aagatatcgt gctgaccctg acactgtttg    3660
aggacagaga gatgatcgag gaacggctga aaacctatgc ccacctgttc gacgacaaag    3720
tgatgaagca gctgaagcgg cggagataca ccggctgggg caggctgagc cggaagctga    3780
tcaacggcat ccgggacaag cagtccggca agacaatcct ggatttcctg aagtccgacg    3840
gcttcgccaa cagaaacttc atgcagctga tccacgacga cagcctgacc tttaaagagg    3900
acatccagaa agcccaggtg tccggccagg gcgatagcct gcacgagcac attgccaatc    3960
tggccggcag ccccgccatt aagaagggca tcctgcagac agtgaaggtg gtggacgagc    4020
tcgtgaaagt gatgggccgg cacaagcccg agaacatcgt gatcgaaatg gccagagaga    4080
accagaccac ccagaaggga cagaagaaca gccgcgagag aatgaagcgg atcgaagagg    4140
gcatcaaaga gctgggcagc cagatcctga aagaacaccc cgtggaaaac acccagctgc    4200
agaacgagaa gctgtacctg tactacctgc agaatgggcg ggatatgtac gtggaccagg    4260
aactggacat caaccggctg tccgactacg atgtggacgc catcgtgcct cagagctttc    4320
tgaaggacga ctccatcgac aacaaggtgc tgaccagaag cgacaagaac cggggcaaga    4380
gcgacaacgt gccctccgaa gaggtcgtga agaagatgaa aactactggc ggcagctgc    4440 tgaacgccaa gctgattacc cagagaaagt tcgacaatct gaccaaggcc gagagaggcg    4500
gcctgagcga actggataag gccggcttca tcaagagaca gctggtggaa acccggcaga    4560
tcacaaagca cgtggcacag atcctggact cccggatgaa cactaagtac gacgagaatg    4620
acaagctgat ccgggaagtg aaagtgatca cccctgaagtc caagctggtg tccgatttcc    4680
ggaaggattt ccagttttac aaagtgcgcg agatcaacaa ctaccaccac gcccacgacg    4740
cctacctgaa cgccgtcgtg ggaaccgccc tgatcaaaaa gtaccctaag ctggaaagcg    4800
agttcgtgta cggcgactac aaggtgtacg acgtgcggaa gatgatcgcc aagagcgagc    4860
aggaaatcgg caaggctacc gccaagtact tcttctacag caacatcatg aacttttca    4920 agaccgagat taccctggcc aacggcgaga tccggaagcg gcctctgatc gagacaaacg    4980
gcgaaaccgg ggagatcgtg tgggataagg gccgggattt tgccaccgtg cggaaagtgc    5040
tgagcatgcc ccaagtgaat atcgtgaaaa agaccgaggt gcagacaggc ggcttcagca    5100
aagagtctat cctgcccaag aggaacagcg ataagctgat cgccagaaag aaggactggg    5160
accctaagaa gtacggcggc ttcgacagcc ccaccgtggc ctattctgtg ctggtggtgg    5220
ccaaagtgga aaagggcaag tccaagaaac tgaagagtgt gaaagagctg ctggggatca    5280
ccatcatgga aagaagcagc ttcgagaaga atcccatcga ctttctggaa gccagggctc    5340
acaaagaagt gaaaaaggac ctgatcatca agctgcctaa gtactccctg ttcgagctgg    5400
```

```
aaaacggccg gaagagaatg ctggcctctg ccggcgaact gcagaaggga acgaactgg     5460 ccctgccctc caaatatgtg aacttcctgt acctggccag ccactatgag aagctgaagg    5520
gctcccccga ggataatgag cagaaacagc tgtttgtgga acagcacaag cactacctgg    5580
acgagatcat cgagcagatc agcgagttct ccaagagagt gatcctggcc gacgctaatc    5640
tggacaaagt gctgtccgcc tacaacaagc accgggataa gcccatcaga gagcaggccg    5700
agaatatcat ccacctgttt accctgacca atctgggagc cctgccgcc ttcaagtact     5760 ttgacaccac catcgaccgg aagaggtaca ccagcaccaa agaggtgctg acgccaccc     5820 tgatccacca gagcatcacc ggcctgtacg agacacggat cgacctgtct cagctgggag    5880
gcgacagccc caagaagaag agaaaggtgg aggccagcgg tggcggagga tccgaactgc    5940
ccacctgcag ctgtcttgat cgagttatac aaaaagacaa aggcccatat tatacacacc    6000
ttggggcagg accaagtgtt gctgctgtca gggaaatcat ggagaatagg tatggtcaaa    6060
aaggaaacgc aataaggata gaaatagtag tgtacaccgg taaagaaggg aaaagctctc    6120
atgggtgtcc aattgctaag tgggttttaa gaagaagcag tgatgaagaa aaagttcttt    6180
gtttggtccg gcagcgtaca ggccaccact gtccaactgc tgtgatggtg gtgctcatca    6240
tggtgtggga tggcatccct cttccaatgg ccgaccggct atacacagag ctcacagaga    6300
atctaaagtc atacaatggg cacccctaccg acagaagatg cacccctcaat gaaaatcgta   6360 cctgtacatg tcaaggaatt gatccagaga cttgtggagc ttcattctct tttggctgtt    6420
catggagtat gtactttaat ggctgtaagt ttggtagaag cccaagcccc agaagattta    6480
gaattgatcc aagctctccc ttacatgaaa aaaaccttga agataactta cagagtttgg    6540
ctacacgatt agctccaatt tataagcagt atgctccagt agcttaccaa aatcaggtgg    6600
aatatgaaaa tgttgcccga gaatgtcggc ttggcagcaa ggaaggtcgt cccttctctg    6660
gggtcactgc ttgcctggac ttctgtgctc atccccacag ggacattcac aacatgaata    6720
atggaagcac tgtggtttgt accttaactc gagaagataa ccgctctttg ggtgttattc    6780
ctcaagatga gcagtccat gtgctacctc tttataagct ttcagacaca gatgagtttg     6840
gctccaagga aggaatggaa gccaagatca aatctggggc catcgaggtc ctggcacccc    6900
gccgcaaaaa aagaacgtgt ttcactcagc ctgttccccg ttctggaaag aagagggctg    6960
cgatgatgac agaggttctt gcacataaga taagggcagt ggaaagaaaa cctattcccc    7020
gaatcaagcg gaagaataac tcaacaacaa caaacaacag taagccttcg tcactgccaa    7080
ccttagggag taacactgag accgtgcaac ctgaagtaaa aagtgaaacc gaaccccatt    7140
ttatcttaaa aagttcagac aacactaaaa cttattcgct gatgccatcc gctcctcacc    7200
cagtgaaaga ggcatctcca ggcttctcct ggtccccgaa gactgcttca gccacaccag    7260
ctccactgaa gaatgacgca acagcctcat gcggttttc agaaagaagc agcactcccc    7320
actgtacgat gccttcggga agactcagtg gtgccaatgc agctgctgct gatggccctg    7380
gcatttcaca gcttggcgaa gtggctcctc tccccaccct gtctgctcct gtgatggagc    7440
ccctcattaa ttctgagcct tccactggtg tgactgagcc gctaacgcct catcagccaa    7500
accaccagcc ctccttcctc acctctcctc aagaccttgc ctcttctcca atggaagaag    7560
atgagcagca ttctgaagca gatgagcctc atcagacga accctatct gatgaccccc     7620 tgtcacctgc tgaggagaaa ttgccccaca ttgatgagta ttggtcagac agtgagcaca    7680 tcttttgga tgcaaatatt ggtggggtgg ccatcgcacc tgctcacggc tcggttttga    7740
```

-continued

```
ttgagtgtgc ccggcgagag ctgcacgcta ccactcctgt tgagcacccc aaccgtaatc      7800
atccaacccg cctctcccct tgtcttttacc agcacaaaaa cctaaataag ccccaacatg     7860
gttttgaact aaacaagatt aagtttgagg ctaaagaagc taagaataag aaaatgaagg      7920
cctcagagca aaaagaccag gcagctaatg aaggtccaga acagtcctct gaagtaaatg     7980
aattgaacca aattccttct cataaagcat taacattaac ccatgacaat gttgtcaccg     8040
tgtcccctta tgctctcaca cacgttgcgg ggccctataa ccattgggtc tgagcggccg     8100
cgactctaga tcataatcag ccataccaca tttgtagagg ttttacttgc tttaaaaaac    8160
ctcccacacc tccccctgaa cctgaaacat aaaatgaatg caattgttgt tgttaacttg    8220
tttattgcag cttataatgg ttacaaataa agcaatagca tcacaaattt cacaaataaa     8280
gcatttttt cactgcattc tagttgtggt ttgtccaaac tcatcaatgt atcttaaggc      8340
gtaaattgta agcgttaata ttttgttaaa attcgcgtta aattttttgtt aaatcagctc    8400
atttttaac caataggccg aaatcggcaa atcccttat aaatcaaaag aatagaccga     8460
gatagggttg agtgttgttc cagtttggaa caagagtcca ctattaaaga acgtggactc    8520
caacgtcaaa gggcgaaaaa ccgtctatca gggcgatggc ccactacgtg aaccatcacc   8580
ctaatcaagt ttttgggggt cgaggtgccg taaagcacta atcggaacc ctaaagggag   8640
cccccgattt agagcttgac ggggaaagcc ggcgaacgtg gcgagaaagg aagggaagaa    8700
agcgaaagga gcgggcgcta gggcgctggc aagtgtagcg gtcacgctgc gcgtaaccac    8760
cacacccgcc gcgcttaatg cgccgctaca gggcgcgtca ggtggcactt tcggggaaa    8820
tgtgcgcgga acccctattt gtttattttt ctaaatacat tcaaatatgt atccgctcat    8880
gagacaataa ccctgataaa tgcttcaata atattgaaaa aggaagagtc ctgaggcgga    8940
aagaaccagc tgtggaatgt gtgtcagtta gggtgtggaa agtccccagg ctccccagca    9000
ggcagaagta tgcaaagcat gcatctcaat tagtcagcaa ccaggtgtgg aaagtccca   9060
ggctccccag caggcagaag tatgcaaagc atgcatctca attagtcagc aaccatagtc    9120
ccgcccctaa ctccgcccat cccgcccta actccgccca gttccgccca ttctccgccc    9180
catggctgac taatttttttt tatttatgca gaggccgagg ccgcctcggc ctctgagcta   9240
ttccagaagt agtgaggagg ctttttggga ggcctaggct tttgcaaaga tcgatcaaga   9300
gacaggatga ggatcgtttc gcatgattga acaagatgga ttgcacgcag gttctccggc   9360
cgcttgggtg gagaggctat tcggctatga ctgggcacaa cagacaatcg gctgctctga   9420
tgccgccgtg ttccggctgt cagcgcaggg gcgcccggtt ctttttgtca agaccgacct    9480
gtccggtgcc ctgaatgaac tgcaagacga ggcagcgcgg ctatcgtggc tggccacgac    9540
gggcgttcct tgcgcagctg tgctcgacgt tgtcactgaa gcgggaaggg actggctgct    9600
attgggcgaa gtgccggggc aggatctcct gtcatctcac cttgctcctg ccgagaaagt    9660
atccatcatg gctgatgcaa tgcggcggct gcatacgctt gatccggcta cctgcccatt    9720
cgaccaccaa gcgaaacatc gcatcgagcg agcacgtact cggatggaag ccggtcttgt    9780
cgatcaggat gatctggacg aagagcatca ggggctcgcg ccagccgaac tgttcgccag    9840
gctcaaggcg agcatgcccg acggcgagga tctcgtcgtg acccatggcg atgcctgctt    9900
gccgaatatc atggtggaaa atggccgctt ttctggattc atcgactgtg gccggctggg    9960
tgtggcggac cgctatcagg acatagcgtt ggctacccgt gatattgctg aagagcttgg   10020
cggcgaatgg gctgaccgct tcctcgtgct ttacggtatc gccgctcccg attcgcagcg   10080
catcgccttc tatcgccttc ttgacgagtt cttctgagcg ggactctggg gttcgaaatg   10140
```

```
accgaccaag cgacgcccaa cctgccatca cgagatttcg attccaccgc cgccttctat    10200
gaaaggttgg gcttcggaat cgttttccgg gacgccggct ggatgatcct ccagcgcggg    10260
gatctcatgc tggagttctt cgcccaccct aggggaggc taactgaaac acggaaggag    10320
acaataccgg aaggaacccg cgctatgacg gcaataaaaa gacagaataa aacgcacggt    10380
gttgggtcgt ttgttcataa acgcggggtt cggtcccagg gctggcactc tgtcgatacc    10440
ccaccgagac cccattgggg ccaatacgcc cgcgtttctt ccttttcccc accccacccc    10500
ccaagttcgg gtgaaggccc agggctcgca gccaacgtcg gggcggcagg ccctgccata    10560
gcctcaggtt actcatatat actttagatt gatttaaaac ttcattttta atttaaaagg    10620
atctaggtga agatcctttt tgataatctc atgaccaaaa tcccttaacg tgagttttcg    10680
ttccactgag cgtcagaccc cgtagaaaag atcaaaggat cttcttgaga tcctttttt    10740 ctgcgcgtaa tctgctgctt gcaaacaaaa aaaccaccgc taccagcggt ggtttgtttg    10800
ccggatcaag agctaccaac tcttttccg aaggtaactg gcttcagcag agcgcagata    10860
ccaaatactg tccttctagt gtagccgtag ttaggccacc acttcaagaa ctctgtagca    10920
ccgcctacat acctcgctct gctaatcctg ttaccagtgg ctgctgccag tggcgataag    10980
tcgtgtctta ccgggttgga ctcaagacga tagttaccgg ataaggcgca gcggtcgggc    11040
tgaacggggg gttcgtgcac acagcccagc ttggagcgaa cgacctacac cgaactgaga    11100
tacctacagc gtgagctatg agaaagcgcc acgcttcccg aagggagaaa ggcggacagg    11160
tatccggtaa gcggcagggt cggaacagga gagcgcacga gggagcttcc agggggaaac    11220
gcctggtatc tttatagtcc tgtcgggttt cgccacctct gacttgagcg tcgatttttg    11280
tgatgctcgt cagggggggcg gagcctatgg aaaaacgcca gcaacgcggc cttttacgg    11340 ttcctggcct tttgctggcc ttttgctcac atgttctttc ctgcgttatc ccctgattct    11400
gtggataacc gtattaccgc catgcat                                         11427
```

<210> SEQ ID NO 7
<211> LENGTH: 10188
<212> TYPE: DNA
<213> ORGANISM: Artificial Sequence
<220> FEATURE:
<223> OTHER INFORMATION: pCAG-dCas9-10xGCN4_v4

<400> SEQUENCE: 7

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catgggtcga ggtgagcccc acgttctgct tcactctccc catctcccc cctccccac     420 ccccaatttt gtatttattt attttttaat tattttgtgc agcgatgggg gcggggggg     480 ggggggcgcg cgccaggcgg ggcggggcgg ggcgagggg ggggcgggc gaggcggaga     540 ggtgcggcgg cagccaatca gagcggcgcg ctccgaaagt ttccttttat ggcgaggcgg     600
cggcggcggc ggccctataa aaagcgaagc gcgcggcggg cggagtcgc tgcgttgcct     660 tcgccccgtg ccccgctccg cgccgcctcg cgccgcccgc cccggctctg actgaccgcg     720
```

-continued

```
ttactcccac aggtgagcgg gcgggacggc ccttctcctc cgggctgtaa ttagcgcttg    780
gtttaatgac ggctcgtttc ttttctgtgg ctgcgtgaaa gccttaaagg gctccgggag    840
ggcccttttgt gcggggggga gcggctcggg gggtgcgtgc gtgtgtgtgt gcgtggggag    900
cgccgcgtgc ggcccgcgct gcccggcggc tgtgagcgct gcgggcgcgg cgcggggctt    960
tgtgcgctcc gcgtgtgcgc gaggggagcg cggccggggg cggtgccccg cggtgcgggg    1020
gggctgcgag gggaacaaag gctgcgtgcg gggtgtgtgc gtggggggt gagcaggggg    1080
tgtgggcgcg gcggtcgggc tgtaaccccc ccctgcaccc ccctcccga gttgctgagc    1140
acggcccggc ttcgggtgcg gggctccgtg cggggcgtgg cgcggggctc gccgtgccgg    1200
gcggggggtg gcggcaggtg ggggtgccgg gcggggcggg gccgcctcgg gccggggagg    1260
gctcggggga ggggcgcggc ggccccggag cgccggcggc tgtcgaggcg cggcgagccg    1320
cagccattgc ctttttatggt aatcgtgcga gagggcgcag ggacttcctt tgtcccaaat    1380
ctggcggagc cgaaatctgg gaggcgccgc cgcacccct ctagcgggcg cgggcgaagc    1440
ggtgcggcgc cggcaggaag gaaatgggcg gggagggcct tcgtgcgtcg ccgcgccgcc    1500
gtccccttct ccatctccag cctcggggct gccgcagggg gacggctgcc ttcgggggg    1560
acggggcagg gcggggttcg gcttctggcg tgtgaccggc ggctctagag cctctgctaa    1620
ccatgttcat gccttcttct ttttcctaca gctcctgggc aacgtgctgg ttgttgtgct    1680
gtctcatcat tttggcaaag aattctgcag tcgacggtac cgcggggccc ctaggctacg    1740
cgcgccacca tgcccaagaa gaagcgcaag gtgggacgcg tctgcaggat atcaagcttg    1800
cggtaccgcg ggcccgggat cgccaccatg gacaagaagt acagcatcgg cctggccatc    1860
ggcaccaact ctgtgggctg gccgtgatc accgacgagt acaaggtgcc cagcaagaaa    1920
ttcaaggtgc tgggcaacac cgaccggcac agcatcaaga gaacctgat cggcgccctg    1980
ctgttcgaca gcggagaaac agccgaggcc accggctga agagaaccgc cagaagaaga    2040
tacaccagac ggaagaaccg gatctgctat ctgcaagaga tcttcagcaa cgagatggcc    2100
aaggtggacg acagcttctt ccacagactg gaagagtcct tcctggtgga agaggataag    2160
aagcacgagc ggcaccccat cttcggcaac atcgtggacg aggtggccta ccacgagaag    2220
taccccacca tctaccacct gagaaagaaa ctggtggaca gcaccgacaa ggccgacctg    2280
cggctgatct atctggccct ggcccacatg atcaagttcc ggggccactt cctgatcgag    2340
ggcgacctga accccgacaa cagcgacgtg gacaagctgt tcatccagct ggtgcagacc    2400
tacaaccagc tgttcgagga aaaccccatc aacgccagcg gcgtggacgc caaggccatc    2460
ctgtctgcca gactgagcaa gagcagacgg ctggaaaatc tgatcgccca gctgcccggc    2520
gagaagaaga atggcctgtt cggcaacctg attgccctga gcctgggcct gacccccaac    2580
ttcaagagca acttcgacct ggccgaggat gccaaactgc agctgagcaa ggacacctac    2640
gacgacgacc tggacaacct gctggcccag atcggcgacc agtacgccga cctgtttctg    2700
gccgccaaga acctgtccga cgccatcctg ctgagcgaca tcctgagagt gaacaccgag    2760
atcaccaagg ccccctgag cgcctctatg atcaagagat acgacgagca ccaccaggac    2820
ctgacccctgc tgaaagctct cgtgcggcag cagctgcctg agaagtacaa agagattttc    2880
ttcgaccaga gcaagaacgg ctacgccggc tacatcgatg gcggagccag ccaggaagag    2940
ttctacaagt tcatcaagcc catcctggaa aagatggacg gcaccgagga actgctcgtg    3000
aagctgaaca gagaggacct gctgcggaag cagcggacct tcgacaacgg cagcatcccc    3060
caccagatcc acctgggaga gctgcacgcc attctgcggc ggcaggaaga tttttaccca    3120
```

```
ttcctgaagg acaaccggga aaagatcgag aagatcctga ccttccgcat ccctactac    3180 gtgggccctc tggccagggg aaacagcaga ttcgcctgga tgaccagaaa gagcgaggaa    3240
accatcaccc cctggaactt cgaggaagtg gtggacaagg gcgccagcgc ccagagcttc    3300
atcgagcgga tgaccaactt cgataagaac ctgcccaacg agaaggtgct gcccaagcac    3360
agcctgctgt acgagtactt caccgtgtac aacgagctga ccaaagtgaa atacgtgacc    3420
gagggaatga gaaagcccgc cttcctgagc ggcgagcaga aaaagccat cgtggacctg    3480 ctgttcaaga ccaaccggaa agtgaccgtg aagcagctga agaggacta cttcaagaaa    3540 atcgagtgct tcgactccgt ggaaatctcc ggcgtggaag atcggttcaa cgcctccctg    3600
ggcacatacc acgatctgct gaaaattatc aaggacaagg acttcctgga caatgaggaa    3660
aacgaggaca ttctggaaga tatcgtgctg accctgacac tgtttgagga cagagagatg    3720
atcgaggaac ggctgaaaac ctatgcccac ctgttcgacg acaaagtgat gaagcagctg    3780
aagcggcgga gataccaccg gctggggcag gctgagccgga agctgatcaa cggcatccgg    3840
gacaagcagt ccggcaagac aatcctggat ttcctgaagt ccgacggctt cgccaacaga    3900
aacttcatgc agctgatcca cgacgacagc ctgaccttta aagaggacat ccagaaagcc    3960
caggtgtccg gccagggcga tagcctgcac gagcacattg ccaatctggc cggcagcccc    4020
gccattaaga agggcatcct gcagacagtg aaggtggtgg acgagctcgt gaaagtgatg    4080
ggccggcaca agcccgagaa catcgtgatc gaaatggcca gagagaacca gaccacccag    4140
aagggacaga gaacagccg cgagagaatg aagcggatcg aagagggcat caaagagctg    4200
ggcagccaga tcctgaaaga acaccccgtg gaaaacaccc agctgcagaa cgagaagctg    4260
tacctgtact acctgcagaa tgggcgggat atgtacgtgg accaggaact ggacatcaac    4320
cggctgtccg actacgatgt ggacgctatc gtgcctcaga gctttctgaa ggacgactcc    4380
atcgataaca aagtgctgac tcggagcgac aagaaccggg gcaagagcga caacgtgccc    4440
tccgaagagg tcgtgaagaa gatgaagaac tactggcgcc agctgctgaa tgccaagctg    4500
attacccaga ggaagttcga caatctgacc aaggccgaga aggcggcct gagcgaactg    4560 gataaggccg gcttcatcaa gagacagctg gtggaaaccc ggcagatcac aaagcacgtg    4620
gcacagatcc tggactcccg gatgaacact aagtacgacg agaacgacaa actgatccgg    4680
gaagtgaaag tgatcaccct gaagtccaag ctggtgtccg atttccggaa ggatttccag    4740
ttttacaaag tgcgcgagat caacaactac caccacgccc acgacgccta cctgaacgcc    4800
gtcgtgggaa ccgccctgat caaaaagtac cctaagctgg aaagcgagtt cgtgtacggc    4860
gactacaagg tgtacgacgt gcggaagatg atcgccaaga gcgagcagga atcggcaag    4920 gctaccgcca gtacttctt ctacagcaac atcatgaact tttttcaagac cgagattacc    4980 ctggccaacg gcgagatccg gaagcggcct ctgatcgaga caaacggcga aacaggcgag    5040
atcgtgtggg ataagggccg ggactttgcc accgtgcgga aagtgctgtc tatgccccaa    5100
gtgaatatcg tgaaaaagac cgaggtgcag acaggcggct tcagcaaaga gtctatcctg    5160
cccaagagga acagcgacaa gctgatcgcc agaaagaagg actgggaccc taagaagtac    5220
ggcggcttcg acagccccac cgtggcctat tctgtgctgg tggtggccaa agtggaaaag    5280
ggcaagtcca gaaaactgaa gagtgtgaaa gagctgctgg ggatcaccat catggaaaga    5340
agcagcttcg agaagaatcc catcgacttt ctggaagcca agggctacaa agaagtgaaa    5400
aaggacctga tcatcaagct gcctaagtac tccctgttcg agctggaaaa cggccggaag    5460
```

```
agaatgctgg cctctgccgg cgaactgcag aagggaaacg aactggccct gccctccaaa   5520
tatgtgaact tcctgtacct ggccagccac tatgagaagc tgaagggctc ccccgaggat   5580
aatgagcaga acagctgtt tgtggaacag cacaaacact acctggacga gatcatcgag    5640
cagatcagcg agttctccaa gagagtgatc ctggccgacg ctaatctgga caaggtgctg   5700
agcgcctaca acaagcacag agacaagcct atcagagagc aggccgagaa tatcatccac   5760
ctgtttaccc tgaccaatct gggagcccct gccgccttca agtactttga caccaccatc   5820
gaccggaaga ggtacaccag caccaaagag gtgctggacg ccaccctgat ccaccagagc   5880
atcaccggcc tgtacgagac acggatcgac ctgtctcagc tgggaggcga cgcctatccc   5940
tatgacgtgc ccgattatgc cagcctgggc agcggctccc ccaagaaaaa acgcaaggtg   6000
gaagatccta agaaaaagcg gaaagtggac ggcattggta gtgggagcaa cggcagcagc   6060
ggatccaacg gtccgactga cgccgcggaa gaagaacttt tgagcaagaa ttatcatctt   6120
gagaacgaag tggctcgtct taagaaaggt tctggcagtg gagaagaact gctttcaaag   6180
aattaccacc tggaaaatga ggtagctaga ctgaaaaagg ggagcggaag tggggaggag   6240
ttgctgagca aaaattatca tttggagaac gaagtagcac gactaaagaa agggtccgga   6300
tcgggtgagg agttactctc gaaaaattat catctcgaaa acgaagtggc tcggctaaaa   6360
aagggcagtg gttctggaga agagctatta tctaaaaact accacctcga aaatgaggtg   6420
gcacgcttaa aaaagggaag tggcagtggt gaagagctac tatccaagaa ttatcatctt   6480
gagaacgagg tagcgcgttt gaagaagggt tccggctcag gagaggaact gctctcgaag   6540
aactatcatc ttgaaaatga ggtcgctcga ttaaaaaagg gatcgggcag tggtgaggaa   6600
ctactttcaa agaattacca cctcgaaaac gaagtagctc gattaaagaa aggttcaggg   6660
tcgggtgaag aattactgag taaaaattat catctggaaa atgaggtagc gagactaaaa   6720
aaggggagtg gttctggcga ggaattgcta tcgaaaaatt atcatcttga gaacgaagtt   6780
gctaggctca aaaagggctc aggctcaggc accgcggtaa acataggtgg tggaaccggt   6840
ccgatggatc tacagcggcc gcgactctag atcataatca gccataccac atttgtagag   6900
gttttacttg cttaaaaaaa cctcccacac ctccccctga acctgaaaca taaaatgaat   6960
gcaattgttg ttgttaactt gtttattgca gcttataatg gttacaaata aagcaatagc   7020
atcacaaatt tcacaaataa agcatttttt tcactgcatt ctagttgtgg tttgtccaaa   7080
ctcatcaatg tatcttaagg cgtaaattgt aagcgttaat attttgttaa aattcgcgtt   7140
aaatttttgt taaatcagct catttttta ccaataggcc gaaatcggca aaatccctta   7200
taaatcaaaa gaatagaccg agatagggtt gagtgttgtt ccagtttgga acaagagtcc   7260
actattaaag aacgtggact ccaacgtcaa agggcgaaaa accgtctatc agggcgatgg   7320
cccactacgt gaaccatcac cctaatcaag ttttttgggg tcgaggtgcc gtaaagcact   7380
aaatcggaac cctaaaggga gcccccgatt tagagcttga cggggaaagc cggcgaacgt   7440
ggcgagaaag gaagggaaga aagcgaaagg agcgggcgct agggcgctgg caagtgtagc   7500
ggtcacgctg cgcgtaacca ccacacccgc cgcgcttaat gcgccgctac agggcgcgtc   7560
aggtggcact tttcggggaa atgtgcgcgg aaccccta tt tgtttatttt tctaaataca   7620
ttcaaatatg tatccgctca tgagacaata accctgataa atgcttcaat aatattgaaa   7680
aaggaagagt cctgaggcgg aaagaaccag ctgtggaatg tgtgtcagtt agggtgtgga   7740
aagtccccag gctccccagc aggcagaagt atgcaaagca tgcatctcaa ttagtcagca   7800
accaggtgtg gaaagtcccc aggctcccca gcaggcagaa gtatgcaaag catgcatctc   7860
```

```
aattagtcag caaccatagt cccgcccta actccgccca tcccgcccct aactccgccc    7920
agttccgccc attctccgcc ccatggctga ctaattttttt ttatttatgc agaggccgag   7980
gccgcctcgg cctctgagct attccagaag tagtgaggag gcttttttgg aggcctaggc   8040
ttttgcaaag atcgatcaag agacaggatg aggatcgttt cgcatgattg aacaagatgg   8100
attgcacgca ggttctccgg ccgcttgggt ggagaggcta ttcggctatg actgggcaca   8160
acagacaatc ggctgctctg atgccgccgt gttccggctg tcagcgcagg ggcgcccggt   8220
tcttttttgtc aagaccgacc tgtccggtgc cctgaatgaa ctgcaagacg aggcagcgcg   8280
gctatcgtgg ctggccacga cgggcgttcc ttgcgcagct gtgctcgacg ttgtcactga   8340
agcgggaagg gactggctgc tattgggcga agtgccgggg caggatctcc tgtcatctca   8400
ccttgctcct gccgagaaag tatccatcat ggctgatgca atgcggcggc tgcatacgct   8460
tgatccggct acctgcccat tcgaccacca agcgaaacat cgcatcgagc gagcacgtac   8520
tcggatggaa gccggtcttg tcgatcagga tgatctggac gaagagcatc aggggctcgc   8580
gccagccgaa ctgttcgcca ggctcaaggc gagcatgccc gacggcgagg atctcgtcgt   8640
gacccatggc gatgcctgct tgccgaatat catggtggaa aatggccgct tttctggatt   8700
catcgactgt ggccggctgg gtgtggcgga ccgctatcag gacatagcgt tggctacccg   8760
tgatattgct gaagagcttg gcggcgaatg ggctgaccgc ttcctcgtgc tttacggtat   8820
cgccgctccc gattcgcagc gcatcgcctt ctatcgcctt cttgacgagt tcttctgagc   8880
gggactctgg ggttcgaaat gaccgaccaa gcgacgccca acctgccatc acgagatttc   8940
gattccaccg ccgccttcta tgaaaggttg ggcttcggaa tcgttttccg ggacgccggc   9000
tggatgatcc tccagcgcgg ggatctcatg ctggagttct cgcccacccc tagggggagg   9060
ctaactgaaa cacggaagga gacaataccg gaaggaaccc gcgctatgac ggcaataaaa   9120
agacagaata aaacgcacgg tgttgggtcg tttgttcata aacgcggggt tcggtcccag   9180
ggctggcact ctgtcgatac cccaccgaga ccccattggg gccaatacgc ccgcgtttct   9240
tccttttccc cacccacccc ccaagttcg ggtgaaggcc cagggctcgc agccaacgtc   9300
ggggcggcag gccctgccat agcctcaggt tactcatata tactttagat tgatttaaaa   9360
cttcattttt aatttaaaag gatctaggtg aagatccttt ttgataatct catgaccaaa   9420
atcccttaac gtgagttttc gttccactga gcgtcagacc ccgtagaaaa gatcaaagga   9480
tcttcttgag atcctttttt tctgcgcgta atctgctgct tgcaaacaaa aaaaccaccg   9540
ctaccagcgg tggtttgttt gccggatcaa gagctaccaa ctctttttcc gaaggtaact   9600
ggcttcagca gagcgcagat accaaatact gtccttctag tgtagccgta gttaggccac   9660
cacttcaaga actctgtagc accgcctaca tacctcgctc tgctaatcct gttaccagtg   9720
gctgctgcca gtggcgataa gtcgtgtctt accgggttgg actcaagacg atagttaccg   9780
gataaggcgc agcggtcggg ctgaacgggg gttcgtgca cacagcccag cttggagcga   9840
acgacctaca ccgaactgag atacctacag cgtgagctat gagaaagcgc cacgcttccc   9900
gaagggagaa aggcggacag gtatccggta agcggcaggg tcggaacagg agagcgcacg   9960
agggagcttc caggggggaaa cgcctggtat ctttatagtc ctgtcgggtt tcgccacctc   10020
tgacttgagc gtcgattttt gtgatgctcg tcagggggggc ggagcctatg gaaaaacgcc   10080
agcaacgcgg cctttttacg gttcctggcc ttttgctggc cttttgctca catgttcttt   10140
cctgcgttat cccctgattc tgtggataac cgtattaccg ccatgcat               10188
```

<210> SEQ ID NO 8
<211> LENGTH: 8829
<212> TYPE: DNA
<213> ORGANISM: Artificial Sequence
<220> FEATURE:
<223> OTHER INFORMATION: pCAG-scFvGCN4sfGFPTET1CD

<400> SEQUENCE: 8

| | | | | | |
|---|---|---|---|---|---|
| tagttattaa | tagtaatcaa | ttacggggtc | attagttcat | agcccatata | tggagttccg | 60 |
| cgttacataa | cttacggtaa | atggcccgcc | tggctgaccg | cccaacgacc | cccgcccatt | 120 |
| gacgtcaata | atgacgtatg | ttcccatagt | aacgccaata | gggactttcc | attgacgtca | 180 |
| atgggtggac | tatttacggt | aaactgccca | cttggcagta | catcaagtgt | atcatatgcc | 240 |
| aagtacgccc | cctattgacg | tcaatgacgg | taaatggccc | gcctggcatt | atgcccagta | 300 |
| catgacctta | tgggactttc | ctacttggca | gtacatctac | gtattagtca | tcgctattac | 360 |
| catgggtcga | ggtgagcccc | acgttctgct | tcactctccc | catctccccc | cctccccac | 420 |
| ccccaattt | gtatttattt | atttttaat | tattttgtgc | agcgatgggg | gcggggggg | 480 |
| ggggggcgcg | cgccaggcgg | ggcggggcgg | ggcgagggc | ggggcgggc | gaggcggaga | 540 |
| ggtgcggcgg | cagccaatca | gagcggcgcg | ctccgaaagt | ttccttttat | ggcgaggcgg | 600 |
| cggcggcggc | ggccctataa | aaagcgaagc | gcgcggcggg | cgggagtcgc | tgcgttgcct | 660 |
| tcgccccgtg | ccccgctccg | cgccgcctcg | cgccgcccgc | cccggctctg | actgaccgcg | 720 |
| ttactcccac | aggtgagcgg | gcgggacggc | ccttctcctc | cgggctgtaa | ttagcgcttg | 780 |
| gtttaatgac | ggctcgtttc | ttttctgtgg | ctgcgtgaaa | gccttaaagg | gctccgggag | 840 |
| ggccctttgt | gcggggggga | gcggctcggg | gggtgcgtgc | gtgtgtgtgt | gcgtggggag | 900 |
| cgccgcgtgc | ggccccgcgct | gcccggcggc | tgtgagcgct | gcgggcgcgg | cgcggggctt | 960 |
| tgtgcgctcc | gcgtgtgcgc | gaggggagcg | cggccggggg | cggtgccccg | cggtgcgggg | 1020 |
| gggctgcgag | ggaacaaag | gctgcgtgcg | gggtgtgtgc | gtggggggt | gagcaggggg | 1080 |
| tgtgggcgcg | gcggtcgggc | tgtaaccccc | ccctgcaccc | ccctccccga | gttgctgagc | 1140 |
| acggcccggc | ttcgggtgcg | ggctccgtg | cggggcgtgg | gcgcggggctc | gccgtgccgg | 1200 |
| gcggggggtg | gcggcaggtg | ggggtgccgg | gcggggcggg | gccgcctcgg | gccggggagg | 1260 |
| gctcggggga | ggggcgcggc | ggccccggag | cgccggcggc | tgtcgaggcg | cggcgagccg | 1320 |
| cagccattgc | cttttatggt | aatcgtgcga | gagggcgcag | ggacttcctt | tgtcccaaat | 1380 |
| ctggcggagc | cgaaatctgg | gaggcgccgc | cgcaccccct | ctagcgggcg | cgggcgaagc | 1440 |
| ggtgcggcgc | cggcaggaag | gaaatgggcg | gggagggcct | tcgtgcgtcg | ccgcgccgcc | 1500 |
| gtccccttct | ccatctccag | cctcggggct | gccgcagggg | gacggctgcc | ttcgggggg | 1560 |
| acggggcagg | gcggggttcg | gcttctggcg | tgtgaccggc | ggctctagag | cctctgctaa | 1620 |
| ccatgttcat | gccttcttct | ttttcctaca | gctcctgggc | aacgtgctgg | ttgttgtgct | 1680 |
| gtctcatcat | tttggcaaag | aattctgcag | tcgacggtac | catgggcccc | gacatcgtga | 1740 |
| tgacccagag | ccccagcagc | ctgagcgcca | gcgtgggcga | ccgcgtgacc | atcacctgcc | 1800 |
| gcagcagcac | cggcgccgtg | accaccagca | actacgccag | ctgggtgcag | agaagcccg | 1860 |
| gcaagctgtt | caagggcctg | atcggcggca | ccaacaaccg | cgcccccggc | gtgcccagcc | 1920 |
| gcttcagcgg | cagcctgatc | ggcgacaagg | ccaccctgac | catcagcagc | ctgcagcccg | 1980 |
| aggacttcgc | cacctacttc | tgcgcccctg | ggtacagcaa | ccactgggtg | ttcggccagg | 2040 |
| gcaccaaggt | ggagctgaag | cgcggcggcg | gcggcagcgg | cggcggcggc | agcggcggcg | 2100 |

```
gcggcagcag cggcggcggc agcgaggtga agctgctgga gagcggcggc ggcctggtgc    2160
agcccggcgg cagcctgaag ctgagctgcg ccgtgagcgg cttcagcctg accgactacg    2220
gcgtgaactg ggtgcgccag gcccccggcc gcggcctgga gtggatcggc gtgatctggg    2280
gcgacggcat caccgactac aacagcgccc tgaaggaccg cttcatcatc agcaaggaca    2340
acggcaagaa caccgtgtac ctgcagatga gcaaggtgcg cagcgacgac accgccctgt    2400
actactgcgt gaccggcctg ttcgactact ggggccaggg caccctggtg accgtgagca    2460
gctacccata cgatgttcca gattacgctg gtggaggcgg aggttctggg ggaggaggta    2520
gtggcggtgg tggttcagga ggcggcggaa gcttggatcc aggtggaggt ggaagcggta    2580
gcaaaggaga agaactttc actggagttg tcccaattct tgttgaatta gatggtgatg    2640
ttaatgggca caaattttct gtccgtggag agggtgaagg tgatgctaca aacgaaaaac    2700
tcacccttaa atttatttgc actactggaa aactacctgt tccgtggcca cacttgtca    2760 ctactctgac ctatggtgtt caatgctttt cccgttatcc ggatcacatg aaacggcatg    2820
actttttcaa gagtgccatg cccgaaggtt atgtacagga acgcactata tctttcaaag    2880
atgacgggac ctacaagacg cgtgctgaag tcaagtttga aggtgatacc cttgttaatc    2940
gtatcgagtt aaagggtatt gattttaaag aagatggaaa cattcttgga cacaaactcg    3000
agtacaactt taactcacac aatgtataca tcacggcaga caacaaaag aatgaatca    3060 aagctaactt caaaattcgc cacaacgttg aagatggttc cgttcaacta gcagaccatt    3120
atcaacaaaa tactccaatt ggcgatggcc ctgtcctttt accagacaac cattacctgt    3180
cgacacaatc tgtcctttcg aaagatccca acgaaaagcg tgaccacatg gtccttcttg    3240
agtttgtaac tgctgctggg attacacatg gcatggatga ctctacaaa ggtgaggtc    3300 ggaccggtgg cggtggcgga ggggctagca gatccgaact gcccacctgc agctgtcttg    3360
atcgagttat acaaaaagac aaaggcccat attatacaca ccttgggca ggaccaagtg    3420 ttgctgctgt cagggaaatc atggagaata ggtatggtca aaaaggaaac gcataagga    3480 tagaaatagt agtgtacacc ggtaaagaag gaaaagctc tcatgggtgt ccaattgcta    3540
agtgggtttt aagaagaagc agtgatgaag aaaaagttct ttgtttggtc cggcagcgta    3600
caggccacca ctgtccaact gctgtgatgg tggtgctcat catggtgtgg gatggcatcc    3660
ctcttccaat ggccgaccgg ctatacacag agctcacaga gaatctaaag tcatacaatg    3720
ggcaccctac cgacagaaga tgcaccctca atgaaaatcg tacctgtaca tgtcaaggaa    3780
ttgatccaga gacttgtgga gcttcattct cttttggctg ttcatggagt atgtacttta    3840
atggctgtaa gtttggtaga agcccaagcc ccagaagatt tagaattgat ccaagctctc    3900
ccttacatga aaaaaccttg aagataact tacagagttt ggctacacga ttagctccaa    3960
tttataagca gtatgctcca gtagcttacc aaaatcaggt ggaatatgaa atgttgccc    4020 gagaatgtcg gcttggcagc aaggaaggtc gtcccttctc tggggtcact gcttgcctgg    4080
acttctgtgc tcatcccac agggacattc acaacatgaa taatggaagc actgtggttt    4140
gtaccttaac tcgagaagat aaccgctctt gggtgttat tcctcaagat gagcagctcc    4200
atgtgctacc tcttttataag ctttcagaca cagatgagtt tggctccaag gaaggaatgg    4260
aagccaagat caaatctggg gccatcgagg tcctggcacc ccgccgcaaa aaagaacgt    4320 gtttcactca gcctgttccc cgttctggaa agaagagggc tgcgatgatg acagaggttc    4380
ttgcacataa gataagggca gtggaaaaga aacctattcc ccgaatcaag cggaagaata    4440
```

-continued

```
actcaacaac aacaaacaac agtaagcctt cgtcactgcc aaccttaggg agtaacactg    4500
agaccgtgca acctgaagta aaagtgaaa ccgaacccca ttttatctta aaaagttcag    4560
acaacactaa aacttattcg ctgatgccat ccgctcctca cccagtgaaa gaggcatctc    4620
caggcttctc ctggtccccg aagactgctt cagccacacc agctccactg aagaatgacg    4680
caacagcctc atgcgggttt tcagaaagaa gcagcactcc ccactgtacg atgccttcgg    4740
gaagactcag tggtgccaat gcagctgctg ctgatggccc tggcatttca cagcttggcg    4800
aagtggctcc tctccccacc ctgtctgctc ctgtgatgga gcccctcatt aattctgagc    4860
cttccactgg tgtgactgag ccgctaacgc ctcatcagcc aaaccaccag ccctccttcc    4920
tcacctctcc tcaagacctt gcctcttctc caatggaaga agatgagcag cattctgaag    4980
cagatgagcc tccatcagac gaaccccctat ctgatgaccc cctgtcacct gctgaggaga    5040
aattgcccca cattgatgag tattggtcag acagtgagca catcttttg gatgcaaata    5100
ttggtggggt ggccatcgca cctgctcacg gctcggtttt gattgagtgt gcccggcgag    5160
agctgcacgc taccactcct gttgagcacc ccaaccgtaa tcatccaacc cgcctctccc    5220
ttgtcttta ccagcacaaa aacctaaata gccccaaca tggttttgaa ctaaacaaga    5280
ttaagtttga ggctaaagaa gctaagaata gaaaatgaa ggcctcagag caaaaagacc    5340
aggcagctaa tgaaggtcca gaacagtcct ctgaagtaaa tgaattgaac caaattcctt    5400
ctcataaagc attaacatta acccatgaca atgttgtcac cgtgtcccct tatgctctca    5460
cacacgttgc ggggccctat aaccattggg tctgagcggc cgcgactcta gatcataatc    5520
agccatacca catttgtaga ggttttactt gctttaaaaa acctcccaca cctcccctg    5580
aacctgaaac ataaaatgaa tgcaattgtt gttgttaact tgtttattgc agcttataat    5640
ggttacaaat aaagcaatag catcacaaat ttcacaaata aagcattttt ttcactgcat    5700
tctagttgtg gtttgtccaa actcatcaat gtatcttaag gcgtaaattg taagcgttaa    5760
tattttgtta aaattcgcgt taaattttg ttaaatcagc tcatttttta accaataggc    5820
cgaaatcggc aaaatccctt ataaatcaaa agaatagacc gagatagggt tgagtgttgt    5880
tccagtttgg aacaagagtc cactattaaa gaacgtggac tccaacgtca aagggcgaaa    5940
aaccgtctat cagggcgatg gcccactacg tgaaccatca ccctaatcaa gttttttggg    6000
gtcgaggtgc cgtaaagcac taaatcggaa ccctaaaggg agcccccgat ttagagcttg    6060
acggggaaag ccggcgaacg tggcgagaaa ggaagggaag aaagcgaaag gagcgggcgc    6120
tagggcgctg gcaagtgtag cggtcacgct gcgcgtaacc accacacccg ccgcgcttaa    6180
tgcgccgcta cagggcgcgt caggtggcac ttttcgggga atgtgcgcg aacccctat    6240
ttgtttattt ttctaaatac attcaaatat gtatccgctc atgagacaat aaccctgata    6300
aatgcttcaa taatattgaa aaaggaagag tcctgaggcg gaaagaacca gctgtggaat    6360
gtgtgtcagt tagggtgtgg aaagtcccca ggctccccag caggcagaag tatgcaaagc    6420
atgcatctca attagtcagc aaccaggtgt ggaaagtccc caggctcccc agcaggcaga    6480
agtatgcaaa gcatgcatct caattagtca gcaaccatag tcccgcccct aactccgccc    6540
atcccgcccc taactccgcc cagttccgcc cattctccgc cccatggctg actaattttt    6600
tttatttatg cagaggccga ggccgcctcg gcctctgagc tattccagaa gtagtgagga    6660
ggcttttttg gaggcctagg cttttgcaaa gatcgatcaa gagacaggat gaggatcgtt    6720
tcgcatgatt gaacaagatg gattgcacgc aggttctccg gccgcttggg tggagaggct    6780
attcggctat gactgggcac aacagacaat cggctgctct gatgccgccg tgttccggct    6840
```

```
gtcagcgcag gggcgcccgg ttcttttttgt caagaccgac ctgtccggtg ccctgaatga   6900
actgcaagac gaggcagcgc ggctatcgtg gctggcacg acgggcgttc cttgcgcagc    6960
tgtgctcgac gttgtcactg aagcgggaag ggactggctg ctattgggcg aagtgccggg    7020
gcaggatctc ctgtcatctc accttgctcc tgccgagaaa gtatccatca tggctgatgc    7080
aatgcggcgg ctgcatacgc ttgatccggc tacctgccca ttcgaccacc aagcgaaaca    7140
tcgcatcgag cgagcacgta ctcggatgga agccggtctt gtcgatcagg atgatctgga    7200
cgaagagcat caggggctcg cgccagccga actgttcgcc aggctcaagg cgagcatgcc    7260
cgacggcgag gatctcgtcg tgacccatgg cgatgcctgc ttgccgaata tcatggtgga    7320
aaatggccgc ttttctggat tcatcgactg tggccggctg ggtgtggcgg accgctatca    7380
ggacatagcg ttggctaccc gtgatattgc tgaagagctt ggcggcgaat gggctgaccg    7440
cttcctcgtg ctttacggta tcgccgctcc cgattcgcag cgcatcgcct tctatcgcct    7500
tcttgacgag ttcttctgag cgggactctg gggttcgaaa tgaccgacca agcgacgccc    7560
aacctgccat cacgagattt cgattccacc gccgccttct atgaaaggtt gggcttcgga    7620
atcgttttcc gggacgccgg ctggatgatc ctccagcgcg ggatctcat gctggagttc    7680 ttcgcccacc ctaggggag gctaactgaa acacggaagg agacaatacc ggaaggaacc    7740
cgcgctatga cggcaataaa aagacagaat aaaacgcacg gtgttgggtc gtttgttcat    7800
aaacgcgggg ttcggtccca gggctggcac tctgtcgata ccccaccgag accccattgg    7860
ggccaatacg cccgcgtttc ttccttttcc cacccacc cccaagttc gggtgaaggc     7920 ccagggctcg cagccaacgt cggggcggca ggccctgcca tagcctcagg ttactcatat    7980
atactttaga ttgatttaaa acttcatttt taatttaaaa ggatctaggt gaagatcctt    8040
tttgataatc tcatgaccaa aatcccttaa cgtgagtttt cgttccactg agcgtcagac    8100
cccgtagaaa agatcaaagg atcttcttga gatccttttt ttctgcgcgt aatctgctgc    8160
ttgcaaacaa aaaaccacc gctaccagcg gtggtttgtt tgccggatca agagctacca    8220
actctttttc cgaaggtaac tggcttcagc agagcgcaga taccaaatac tgtccttcta    8280
gtgtagccgt agttaggcca ccacttcaag aactctgtag caccgcctac atacctcgct    8340
ctgctaatcc tgttaccagt ggctgctgcc agtggcgata agtcgtgtct taccgggttg    8400
gactcaagac gatagttacc ggataaggcg cagcggtcgg gctgaacggg gggttcgtgc    8460
acacagccca gcttggagcg aacgacctac accgaactga gatacctaca gcgtgagcta    8520
tgagaaagcg ccacgcttcc cgaagggaga aaggcggaca ggtatccggt aagcggcagg    8580
gtcggaacag gagagcgcac gagggagctt ccaggggaa acgcctggta tctttatagt    8640
cctgtcgggt ttcgccacct ctgacttgag cgtcgatttt tgtgatgctc gtcaggggg    8700 cggagcctat ggaaaaacgc cagcaacgcg gcctttttac ggttcctggc cttttgctgg    8760
ccttttgctc acatgttctt tcctgcgtta tcccctgatt ctgtggataa ccgtattacc    8820
gccatgcat                                                            8829
```

<210> SEQ ID NO 9  
<211> LENGTH: 10042  
<212> TYPE: DNA  
<213> ORGANISM: Artificial Sequence  
<220> FEATURE:  
<223> OTHER INFORMATION: pCAG-dCas9-5xPlat2Afl D

<400> SEQUENCE: 9

-continued

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggac tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catgggtcga ggtgagcccc acgttctgct tcactctccc catctccccc cctccccac   420
ccccaatttt gtatttattt attttttaat tattttgtgc agcgatgggg gcggggggg   480
gggggcgcg cgccaggcgg ggcggggcgg ggcgagggggc gggcggggc gaggcggaga    540
ggtgcggcgg cagccaatca gagcggcgcg ctccgaaagt ttcctttat ggcgaggcgg    600
cggcggcggc ggccctataa aaagcgaagc gcgcggcggg cggagtcgc tgcgttgcct    660
tcgcccgtg cccgctccg cgccgcctcg cgccgcccgc cccggctctg actgaccgcg    720
ttactcccac aggtgagcgg gcgggacggc ccttctcctc cgggctgtaa ttagcgcttg    780
gtttaatgac ggctcgtttc ttttctgtgg ctgcgtgaaa gccttaaagg gctccgggag    840
ggcccttgt gcggggggga gcggctcggg gggtgcgtgc gtgtgtgtgt gcgtgggag    900
cgccgcgtgc ggcccgcgct gcccggcggc tgtgagcgct gcgggcgcgg cgcggggctt    960
tgtgcgctcc gcgtgtgcgc gagggggagc cggccggggg cggtgcccg cggtgcgggg   1020
gggctgcgag gggaacaaag gctgcgtgcg gggtgtgtgc gtgggggggt gagcaggggg   1080
tgtgggcgcg gcgtcgggc tgtaaccccc ccctgcaccc ccctcccga gttgctgagc    1140
acggcccggc ttcgggtgcg gggctccgtg cggggcgtgg cgcggggctc gccgtgccgg   1200
gcggggggtg gcggcaggtg ggggtgccgg gcggggcggg gccgcctcgg gccggggagg   1260
gctcggggga ggggcgcggc ggccccggag cgccggcggc tgtcgaggcg cggcgagccg   1320
cagccattgc cttttatggt aatcgtgcga gagggcgcag ggacttcctt tgtcccaaat   1380
ctggcggagc cgaaatctgg gaggcgccgc cgcaccccct ctagcgggcg cgggcgaagc   1440
ggtgcggcgc cggcaggaag gaaatgggcg ggagggggcct tcgtgcgtcg ccgcgccgcc   1500
gtccccttct ccatctccag cctcggggct gccgcagggg gacggctgcc ttcgggggg   1560
acggggcagg gcggggttcg gcttctggcg tgtgaccggc ggctctagag cctctgctaa   1620
ccatgttcat gccttcttct ttttcctaca gctcctgggc aacgtgctgg ttgttgtgct   1680
gtctcatcat tttggcaaag aattctgcag tcgacggtac gcgggcccc ctaggctacg    1740
cgcgccacca tgcccaagaa gaagcgcaag gtgggacgcg tctgcaggat atcaagcttg   1800
cggtaccgcg ggcccgggat cgccaccatg gacaagaagt acagcatcgg cctggccatc   1860
ggcaccaact ctgtgggctg gccgtgatc accgacgagt acaaggtgcc cagcaagaaa   1920
ttcaaggtgc tgggcaacac cgaccggcac agcatcaaga gaacctgat cggcgccctg   1980
ctgttcgaca gcggagaaac agccgaggcc acccggctga agagaaccgc cagaagaaga   2040
tacaccagac ggaagaaccg gatctgctat ctgcaagaga tcttcagcaa cgagatggcc   2100
aaggtggaca cagcttctt ccacagactg gaagagtcct tcctggtgga agaggataag   2160
aagcacgagc ggcaccccat cttcggcaac atcgtggacg aggtggccta ccacgagaag   2220
tacccccacca tctaccacct gagaaagaaa ctggtggaca gcaccgacaa ggccgacctg   2280
cggctgatct atctggccct ggcccacatg atcaagttcc gggccacttt cctgatcgag   2340
ggcgacctga accccgacaa cagcgacgtg gacaagctgt tcatccagct ggtgcagacc   2400
```

```
tacaaccagc tgttcgagga aaacccatc aacgccagcg gcgtggacgc caaggccatc    2460
ctgtctgcca gactgagcaa gagcagacgg ctggaaaatc tgatcgccca gctgccggc    2520 gagaagaaga atggcctgtt cggcaacctg attgccctga gcctgggcct gaccccaac    2580 ttcaagagca acttcgacct ggccgaggat gccaaactgc agctgagcaa ggacacctac    2640
gacgacgacc tggacaacct gctggcccag atcggcgacc agtacgccga cctgtttctg    2700
gccgccaaga acctgtccga cgccatcctg ctgagcgaca tcctgagagt gaacaccgag    2760
atcaccaagg ccccctgag cgcctctatg atcaagagat acgacgagca ccaccaggac    2820
ctgaccctgc tgaaagctct cgtgcggcag cagctgcctg agaagtacaa agagattttc    2880
ttcgaccaga gcaagaacgg ctacgccggc tacatcgatg gcggagccag ccaggaagag    2940
ttctacaagt tcatcaagcc catcctggaa aagatggacg gcaccgagga actgctcgtg    3000
aagctgaaca gagaggacct gctgcggaag cagcggacct tcgacaacgg cagcatcccc    3060
caccagatcc acctgggaga gctgcacgcc attctgcggc ggcaggaaga tttttaccca    3120
ttcctgaagg acaaccggga aaagatcgag aagatcctga ccttccgcat ccctactac    3180 gtgggccctc tggccagggg aaacagcaga ttcgcctgga tgaccagaaa gagcgaggaa    3240
accatcaccc cctggaactt cgaggaagtg gtggacaagg cgccagcgc ccagagcttc    3300 atcgagcgga tgaccaactt cgataagaac ctgcccaacg agaaggtgct gcccaagcac    3360
agcctgctgt acgagtactt caccgtgtac aacgagctga ccaaagtgaa atacgtgacc    3420
gagggaatga gaaagcccgc cttcctgagc ggcgagcaga aaaagagcat cgtggacctg    3480
ctgttcaaga ccaaccggaa agtgaccgtg aagcagctga agaggacta cttcaagaaa    3540 atcgagtgct tcgactccgt ggaaatctcc ggcgtggaag atcggttcaa cgcctccctg    3600
ggcacatacc acgatctgct gaaaattatc aaggacaagg acttcctgga caatgaggaa    3660
aacgaggaca ttctggaaga tatcgtgctg accctgacac tgtttgagga cagagagatg    3720
atcgaggaac ggctgaaaac ctatgcccac ctgttcgacg acaaagtgat gaagcagctg    3780
aagcggcgga gatacaccgg ctggggcagg ctgagccgga agctgatcaa cggcatccgg    3840
gacaagcagt ccggcaagac aatcctggat ttcctgaagt ccgacggctt cgccaacaga    3900
aacttcatgc agctgatcca cgacgacagc ctgacctttta agaggacat ccagaaagcc    3960 caggtgtccg gccagggcga tagcctgcac gagcacattg ccaatctggc cggcagcccc    4020
gccattaaga agggcatcct gcagacagtg aaggtggtgg acgagctcgt gaaagtgatg    4080
ggccggcaca agcccgagaa catcgtgatc gaaatggcca gagagaacca gaccacccag    4140
aagggacaga agaacagccg cgagagaatg aagcggatcg aagagggcat caaagagctg    4200
ggcagccaga tcctgaaaga acaccccgtg gaaaacaccc agctgcagaa cgagaagctg    4260
tacctgtact acctgcagaa tgggcgggat atgtacgtgg accaggaact ggacatcaac    4320
cggctgtccg actacgatgt ggacgctatc gtgcctcaga gctttctgaa ggacgactcc    4380
atcgataaca aagtgctgac tcggagcgac aagaaccggg gcaagagcga caacgtgccc    4440
tccgaagagg tcgtgaagaa gatgaagaac tactggcgcc agctgctgaa tgccaagctg    4500
attacccaga ggaagttcga caatctgacc aaggccgaga gaggcggcct gagcgaactg    4560
gataaggccg gcttcatcaa gagacagctg gtggaaaccc ggcagatcac aaagcacgtg    4620
gcacagatcc tggactcccg gatgaacact aagtacgacg agaacgacaa actgatccgg    4680
gaagtgaaag tgatcaccct gaagtccaag ctggtgtccg atttccggaa ggatttccag    4740
```

-continued

```
ttttacaaag tgcgcgagat caacaactac caccacgccc acgacgccta cctgaacgcc    4800
gtcgtgggaa ccgccctgat caaaaagtac cctaagctgg aaagcgagtt cgtgtacggc    4860
gactacaagg tgtacgacgt gcggaagatg atcgccaaga gcgagcagga aatcggcaag    4920
gctaccgcca agtacttctt ctacagcaac atcatgaact ttttcaagac cgagattacc    4980
ctggccaacg gcgagatccg gaagcggcct ctgatcgaga caaacggcga aacaggcgag    5040
atcgtgtggg ataagggccg ggactttgcc accgtgcgga aagtgctgtc tatgccccaa    5100
gtgaatatcg tgaaaaagac cgaggtgcag acaggcggct tcagcaaaga gtctatcctg    5160
cccaagagga acagcgacaa gctgatcgcc agaaagaagg actgggaccc taagaagtac    5220
ggcggcttcg acagccccac cgtggcctat tctgtgctgg tggtggccaa agtggaaaag    5280
ggcaagtcca agaaactgaa gagtgtgaaa gagctgctgg ggatcaccat catggaaaga    5340
agcagcttcg agaagaatcc catcgacttt ctggaagcca agggctacaa agaagtgaaa    5400
aaggacctga tcatcaagct gcctaagtac tccctgttcg agctggaaaa cggccggaag    5460
agaatgctgg cctctgccgg cgaactgcag aagggaaacg aactgccct gcctccaaa     5520
tatgtgaact tcctgtacct ggccagccac tatgagaagc tgaagggctc ccccgaggat    5580
aatgagcaga acagctgtt tgtggaacag cacaaacact acctggacga gatcatcgag    5640
cagatcagcg agttctccaa gagagtgatc ctggccgacg ctaatctgga caaggtgctg    5700
agcgcctaca acaagcacag agacaagcct atcagagagc aggccgagaa tatcatccac    5760
ctgtttaccc tgaccaatct gggagccct gccgccttca agtactttga caccaccatc     5820
gaccggaaga ggtacaccag caccaaagag gtgctggacg ccaccctgat ccaccagagc    5880
atcaccggcc tgtacgagac acggatcgac ctgtctcagc tgggaggcga cgcctatccc    5940
tatgacgtgc ccgattatgc cagcctgggc agcggctccc ccaagaaaaa acgcaaggtg    6000
gaagatccta gaaaaagcg gaaagtggac ggcattggta gtgggagcaa cggcagcagc    6060
ggatccaacg gtccgactga cgccgcgaa gaggagcttc tgagcaaaaa ctatcacctc    6120
gaaaacgagg ttgcgcgact gaagaaagga agcgggtccg gtggaagtgg ctccggatct    6180
ggaggttctg gcagcggagg tagcggcagt ggcgaagagc tccttagtaa gaactatcat    6240
ctggaaaatg aggtagcgcg cttaaagaaa gggtcgggaa gtggcggcag cggaagtggg    6300
agtggaggga gcggttctgg cggttccggc agtggagagg agttgctgtc taagaactac    6360
cacttagaaa acgaagtcgc acggctaaaa aaaggttccg gctccggcgg ctccggttct    6420
ggaagcgggg gctcgggatc aggtggatct ggatcaggag aggaattgct ttccaaaaac    6480
taccaccttg agaatgaggt ggccaggtta agaaggggga gcggctcggg gggtagtgga    6540
tcggggtcgg gcgggtcagg aagcggtggt agcggatctg ggaggagct gctctcgaag    6600
aattaccatt tggagaacga agtggcgaga ctaaagaagg gaagcggtag tggtggttca    6660
gggtctggtt caggtggcag tgggtctggg ggctcaggt ccgggtaggc ggccgcgact     6720
ctagatcata atcagccata ccacatttgt agaggtttta cttgctttaa aaaacctccc    6780
acacctcccc ctgaacctga acataaaat gaatgcaatt gttgttgtta acttgtttat    6840
tgcagcttat aatggttaca ataaagcaa tagcatcaca aatttcacaa ataaagcatt     6900
ttttcactg cattctagtt gtggtttgtc caaactcatc aatgtatctt aaggcgtaaa    6960
ttgtaagcgt taatattttg ttaaaattcg cgttaaattt ttgttaaatc agctcatttt    7020
ttaaccaata ggccgaaatc ggcaaaatcc cttataaatc aaaagaatag accgagatag    7080
ggttgagtgt tgttccagtt tggaacaaga gtccactatt aaagaacgtg gactccaacg    7140
```

```
tcaaagggcg aaaaaccgtc tatcagggcg atggcccact acgtgaacca tcaccctaat    7200
caagtttttt ggggtcgagg tgccgtaaag cactaaatcg gaaccctaaa gggagccccc    7260
gatttagagc ttgacgggga aagccggcga acgtggcgag aaaggaaggg aagaaagcga    7320
aaggagcggg cgctagggcg ctggcaagtg tagcggtcac gctgcgcgta accaccacac    7380
ccgccgcgct taatgcgccg ctacagggcg cgtcaggtgg cacttttcgg ggaaatgtgc    7440
gcggaacccc tatttgttta ttttctaaa tacattcaaa tatgtatccg ctcatgagac     7500
aataaccctg ataaatgctt caataatatt gaaaaggaa gagtcctgag gcggaaagaa     7560
ccagctgtgg aatgtgtgtc agttagggtg tggaaagtcc ccaggctccc cagcaggcag    7620
aagtatgcaa agcatgcatc tcaattagtc agcaaccagg tgtggaaagt ccccaggctc    7680
cccagcaggc agaagtatgc aaagcatgca tctcaattag tcagcaacca tagtcccgcc    7740
cctaactccg cccatcccgc cctaactcc gcccagttcc gcccattctc cgccccatgg     7800
ctgactaatt ttttttattt atgcagaggc cgaggccgcc tcggcctctg agctattcca    7860
gaagtagtga ggaggctttt ttggaggcct aggcttttgc aaagatcgat caagagacag    7920
gatgaggatc gtttcgcatg attgaacaag atggattgca cgcaggttct ccggccgctt    7980
gggtggagag gctattcggc tatgactggg cacaacagac aatcggctgc tctgatgccg    8040
ccgtgttccg gctgtcagcg caggggcgcc cggttctttt tgtcaagacc gacctgtccg    8100
gtgccctgaa tgaactgcaa gacgaggcag cgcggctatc gtggctggcc acgacgggcg    8160
ttccttgcgc agctgtgctc gacgttgtca ctgaagcggg aagggactgg ctgctattgg    8220
gcgaagtgcc ggggcaggat ctcctgtcat ctcaccttgc tcctgccgag aaagtatcca    8280
tcatggctga tgcaatgcgg cggctgcata cgcttgatcc ggctacctgc ccattcgacc    8340
accaagcgaa acatcgcatc gagcgagcac gtactcggat ggaagccggt cttgtcgatc    8400
aggatgatct ggacgaagag catcaggggc tcgcgccagc cgaactgttc gccaggctca    8460
aggcgagcat gcccgacggc gaggatctcg tcgtgaccca tggcgatgcc tgcttgccga    8520
atatcatggt ggaaaatggc cgcttttctg gattcatcga ctgtggccgg ctgggtgtgg    8580
cggaccgcta tcaggacata gcgttggcta cccgtgatat tgctgaagag cttggcggcg    8640
aatgggctga ccgcttcctc gtgctttacg gtatcgccgc tcccgattcg cagcgcatcg    8700
ccttctatcg ccttcttgac gagttcttct gagcgggact ctggggttcg aaatgaccga    8760
ccaagcgacg cccaacctgc catcacgaga tttcgattcc accgccgcct tctatgaaag    8820
gttgggcttc ggaatcgttt tccgggacgc cggctgatg atcctccagc gcgggatct     8880 catgctggag ttcttcgccc accctagggg gaggctaact gaaacacgga aggagacaat    8940
accgaaggaa acccgcgcta tgacggcaat aaaaagacag aataaaacgc acggtgttgg    9000
gtcgtttgtt cataaacgcg gggttcggtc ccagggctgg cactctgtcg ataccccacc    9060 gagacccat tggggccaat acgcccgcgt tcttcctttt tccccacccc accccccaag     9120
ttcgggtgaa ggcccagggc tcgcagccaa cgtcggggcg caggccctg ccatagcctc     9180 aggttactca tatatacttt agattgattt aaaacttcat ttttaattta aaaggatcta    9240
ggtgaagatc cttttgata atctcatgac caaaatccct taacgtgagt ttcgttcca     9300 ctgagcgtca gaccccgtag aaaagatcaa aggatcttct tgagatcctt ttttctgcg    9360 cgtaatctgc tgcttgcaaa caaaaaaacc accgctacca gcggtggttt gtttgccgga    9420
tcaagagcta ccaactcttt ttccgaaggt aactggcttc agcagagcgc agataccaaa    9480
```

-continued

| | |
|---|---|
| tactgtcctt ctagtgtagc cgtagttagg ccaccacttc aagaactctg tagcaccgcc | 9540 |
| tacataccte gctctgctaa tcctgttacc agtggctgct gccagtggcg ataagtcgtg | 9600 |
| tcttaccggg ttggactcaa gacgatagtt accggataag gcgcagcggt cgggctgaac | 9660 |
| ggggggttcg tgcacacagc ccagcttgga gcgaacgacc tacaccgaac tgagatacct | 9720 |
| acagcgtgag ctatgagaaa gcgccacgct cccgaaggg agaaaggcgg acaggtatcc | 9780 |
| ggtaagcggc agggtcggaa caggagagcg cacgagggag cttccagggg gaaacgcctg | 9840 |
| gtatctttat agtcctgtcg ggtttcgcca cctctgactt gagcgtcgat ttttgtgatg | 9900 |
| ctcgtcaggg gggcggagcc tatggaaaaa cgccagcaac gcggcctttt tacggttcct | 9960 |
| ggccttttgc tggccttttg ctcacatgtt ctttcctgcg ttatcccctg attctgtgga | 10020 |
| taaccgtatt accgccatgc at | 10042 |

<210> SEQ ID NO 10
<211> LENGTH: 10042
<212> TYPE: DNA
<213> ORGANISM: Artificial Sequence
<220> FEATURE:
<223> OTHER INFORMATION: pCAG-dCas9-3.5xSuper

<400> SEQUENCE: 10

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggac tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtcga ggtgagcccc acgttctgct tcactctccc catctccccc cctccccac | 420 |
| ccccaattt gtatttattt attttttaat tattttgtgc agcgatgggg gcggggggg | 480 |
| gggggcgcg cgccaggcgg ggcggggcgg ggcgagggc gggcgggc gaggcggaga | 540 |
| ggtgcggcg cagccaatca gagcggcgcg ctccgaaagt tcctttttat ggcgaggcgg | 600 |
| cggcggcggc ggccctataa aaagcgaagc gcgcggcggg cgggagtcgc tgcgttgcct | 660 |
| tcgccccgtg ccccgctccg cgccgcctcg cgccgcccgc cccggctctg actgaccgcg | 720 |
| ttactcccac aggtgagcgg gcgggacggc ccttctcctc cgggctgtaa ttagcgcttg | 780 |
| gtttaatgac ggctcgtttc ttttctgtgg ctgcgtgaaa gccttaaagg gctccgggag | 840 |
| ggccctttgt gcgggggga gcggctcggg gggtgcgtgc gtgtgtgtgt gcgtggggag | 900 |
| cgccgcgtgc ggcccgcgct gcccggcggc tgtgagcgct gcgggcgcgg cgcgggctt | 960 |
| tgtgcgctcc gcgtgtgcgc gaggggagcg cggccggggg cggtgccccg cggtgcgggg | 1020 |
| gggctgcgag gggaacaaag gctgcgtgcg gggtgtgtgc gtggggggt gagcagggg | 1080 |
| tgtgggcgcg gcggtcgggc tgtaaccccc ccctgcaccc ccctccccga gttgctgagc | 1140 |
| acggcccggc ttcgggtgcg gggctccgtg cggggcgtgg cgcggggctc gccgtgccgg | 1200 |
| gcggggggtg gcggcaggtg ggggtgccgg cggggcgggg gccgcctcgg gccggggagg | 1260 |
| gctcggggga ggggcgcggc ggccccggag cgccggcggc tgtcgaggcg cggcgagccg | 1320 |
| cagccattgc cttttatggt aatcgtgcga gagggcgcag ggacttcctt tgtcccaaat | 1380 |
| ctggcggagc cgaaatctgg gaggcgccgc cgcaccccct ctagcgggcg cgggcgaagc | 1440 |
| ggtgcggcgc cggcaggaag gaaatgggcg gggagggcct tcgtgcgtcg ccgcgccgcc | 1500 |

```
gtccccttct ccatctccag cctcggggct gccgcagggg gacggctgcc ttcgggggg      1560
acggggcagg gcggggttcg gcttctggcg tgtgaccggc ggctctagag cctctgctaa      1620
ccatgttcat gccttcttct ttttcctaca gctcctgggc aacgtgctgg ttgttgtgct      1680
gtctcatcat tttggcaaag aattctgcag tcgacggtac cgcgggcccc ctaggctacg      1740
cgcgccacca tgcccaagaa gaagcgcaag gtgggacgcg tctgcaggat atcaagcttg      1800
cggtaccgcg ggcccgggat cgccaccatg gacaagaagt acagcatcgg cctgccatc       1860
ggcaccaact ctgtgggctg gccgtgatc accgacgagt acaaggtgcc cagcaagaaa       1920
ttcaaggtgc tggcaacac cgaccggcac agcatcaaga gaacctgat cggcgccctg        1980
ctgttcgaca gcggagaaac agccgaggcc accggctga agagaaccgc cagaagaaga      2040
tacaccagac ggaagaaccg gatctgctat ctgcaagaga tcttcagcaa cgagatggcc     2100
aaggtggacg acagcttctt ccacagactg aagagtcct tcctggtgga agaggataag      2160
aagcacgagc ggcaccccat cttcggcaac atcgtggacg aggtggccta ccacgagaag     2220
taccccacca tctaccacct gagaaagaaa ctggtggaca gcaccgacaa ggccgacctg     2280
cggctgatct atctggccct ggcccacatg atcaagttcc ggggccactt cctgatcgag     2340
ggcgacctga accccgacaa cagcgacgtg gacaagctgt tcatccagct ggtgcagacc     2400
tacaaccagc tgttcgagga aaaccccatc aacgccagcg gcgtggacgc caaggccatc     2460
ctgtctgcca gactgagcaa gagcagacgg ctggaaaatc tgatcgccca gctgcccggc    2520
gagaagaaga atggcctgtt cggcaacctg attgccctga gcctgggcct gacccccaac    2580
ttcaagagca acttcgacct ggccgaggat gccaaactgc agctgagcaa ggacacctac    2640
gacgacgacc tggacaacct gctggcccag atcggcgacc agtacgccga cctgtttctg    2700
gccgccaaga acctgtccga cgccatcctg ctgagcgaca tcctgagagt gaacaccgag    2760
atcaccaagg cccccctgag cgcctctatg atcaagagat acgacgagca ccaccaggac    2820
ctgacccctgc tgaaagctct cgtgcggcag cagctgcctg agaagtacaa agagattttc    2880
ttcgaccaga gcaagaacgg ctacgccggc tacatcgatg gcggagccag ccaggaagag    2940
ttctacaagt tcatcaagcc catcctggaa aagatggacg gcaccgagga actgctcgtg    3000
aagctgaaca gagaggacct gctgcggaag cagcggacct tcgacaacgg cagcatcccc    3060
caccagatcc acctgggaga gctgcacgcc attctgcggc ggcaggaaga tttttaccca    3120
ttcctgaagg acaaccggga aaagatcgag aagatcctga ccttccgcat ccctactac     3180
gtgggccctc tggccagggg aaacagcaga ttcgcctgga tgaccagaaa gagcgaggaa    3240
accatcaccc cctggaactt cgaggaagtg gtggacaagg gcgccagcgc ccagagcttc    3300
atcgagcgga tgaccaactt cgataagaac ctgcccaacg agaaggtgct gcccaagcac    3360
agcctgctgt acgagtactt caccgtgtac aacgagctga ccaaagtgaa atacgtgacc    3420
gagggaatga gaaagcccgc cttcctgagc ggcgagcaga aaaaagccat cgtggacctg    3480
ctgttcaaga ccaaccggaa agtgaccgtg aagcagctga aggaggacta cttcaagaaa    3540
atcgagtgct tcgactccgt ggaaatctcc ggcgtggaag atcggttcaa cgcctccctg    3600
ggcacatacc acgatctgct gaaaattatc aaggacaagg acttcctgga caatgaggaa    3660
aacgaggaca ttctggaaga tatcgtgctg accctgacac tgtttgagga cagagagatg    3720
atcgaggaac ggctgaaaac ctatgcccac ctgttcgacg acaaagtgat gaagcagctg    3780
aagcggcgga gatacaccgg ctggggcagg ctgagccgga agctgatcaa cggcatccgg    3840
```

-continued

```
gacaagcagt ccggcaagac aatcctggat ttcctgaagt ccgacggctt cgccaacaga   3900
aacttcatgc agctgatcca cgacgacagc ctgacctttA aagaggacat ccagaaagcc   3960
caggtgtccg gccagggcga tagcctgcac gagcacattg ccaatctggc cggcagcccc   4020
gccattaaga agggcatcct gcagacagtg aaggtggtgg acgagctcgt gaaagtgatg   4080
ggccggcaca agcccgagaa catcgtgatc gaaatggcca gagagaacca gaccacccag   4140
aagggacaga agaacagccg cgagagaatg aagcggatcg aagagggcat caaagagctg   4200
ggcagccaga tcctgaaaga acaccccgtg aaaacaccc agctgcagaa cgagaagctg   4260
tacctgtact acctgcagaa tgggcgggat atgtacgtgg accaggaact ggacatcaac   4320
cggctgtccg actacgatgt ggacgctatc gtgcctcaga gctttctgaa ggacgactcc   4380
atcgataaca aagtgctgac tcggagcgac aagaaccggg gcaagagcga caacgtgccc   4440
tccgaagagg tcgtgaagaa gatgaagaac tactggcgcc agctgctgaa tgccaagctg   4500
attacccaga ggaagttcga caatctgacc aaggccgaga aggcggcct gagcgaactg   4560 gataaggccg gcttcatcaa gagacagctg gtggaaaccc ggcagatcac aaagcacgtg   4620
gcacagatcc tggactcccg gatgaacact aagtacgacg agaacgacaa actgatccgg   4680
gaagtgaaag tgatcaccct gaagtccaag ctggtgtccg atttccggaa ggatttccag   4740
ttttacaaag tgcgcgagat caacaactac caccacgccc acgacgccta cctgaacgcc   4800
gtcgtgggaa ccgccctgat caaaaagtac cctaagctgg aaagcgagtt cgtgtacggc   4860
gactacaagg tgtacgacgt gcggaagatg atcgccaaga gcgagcagga aatcggcaag   4920
gctaccgcca gtacttctt ctacagcaac atcatgaact ttttcaagac cgagattacc   4980
ctggccaacg gcgagatccg gaagcggcct ctgatcgaga caaacggcga aacaggcgag   5040
atcgtgtggg ataagggccg ggactttgcc accgtgcgga agtgctgtc tatgcccccaa   5100 gtgaatatcg tgaaaaagac cgaggtgcag acaggcggct tcagcaaaga gtctatcctg   5160
cccaagagga cagcgacaa gctgatcgcc agaaagaagg actgggaccc taagaagtac   5220
ggcggcttcg acagccccac cgtggcctat tctgtgctgg tggtggccaa agtggaaaag   5280
ggcaagtcca gaaactgaa gagtgtgaaa gagctgctgg ggatcaccat catggaaaga   5340
agcagcttcg agaagaatcc catcgacttt ctggaagcca agggctacaa agaagtgaaa   5400
aaggacctga tcatcaagct gcctaagtac tccctgttcg agctgaaaaa cggccggaag   5460
agaatgctgg cctctgccgg cgaactgcag aagggaaacg aactggccct gccctccaaa   5520
tatgtgaact tcctgtacct ggccagccac tatgagaagc tgaagggctc ccccgaggat   5580
aatgagcaga aacagctgtt tgtggaacag cacaaacact acctggacga gatcatcgag   5640
cagatcagcg agttctccaa gagagtgatc ctggccgacg ctaatctgga caaggtgctg   5700
agcgcctaca acaagcacag agacaagcct atcagagagc aggccgagaa tatcatccac   5760
ctgtttaccc tgaccaatct gggagcccct gccgccttca gtactttga caccaccatc   5820 gaccggaaga ggtacaccag caccaaagag gtgctggacg ccaccctgat ccaccagagc   5880
atcaccggcc tgtacgagac acggatcgac ctgtctcagc tgggaggcga cgcctatccc   5940
tatgacgtgc ccgattatgc cagcctgggc agcggctccc ccaagaaaaa acgcaaggtg   6000
gaagatccta gaaaaagcg aaagtggac ggcattggta gtgggagcaa cggcagcagc   6060
ggatccaacg gtccgactga cgccgcggaa gaggaactcc tatcaaagaa ttatcacttg   6120
gaaaacgaag tggctagact gaaaaagggg tcggaagcg gaggtagtgg gtctggagga   6180
agcggatcag gaggtagcgg ctccggcgga tcgggtgggt ccggctcagg cggatcgggt   6240
```

```
tctgggggt caggttcagg tggatctggt tccggcgaag aactcctttc caagaactac   6300
catttggaga atgaagtggc cagactcaag aaagggagcg gtccggtgg ctccggatct    6360 ggtggatcgg gaagtggggg atcaggttcc ggagggtcag gcggttcagg gtcaggaggc   6420
agtggctcgg gggggagcgg ctctggcggc tcagggtcgg gagaggagtt actcagtaag   6480
aactatcacc tcgaaaatga agtcgctcgc ctcaaaaaag gatcaggatc tggcgggtct   6540
gggagtggcg gcagcggtag cggcggaagt ggttctggtg ggtcagggg ctccggtagc    6600 gggggaagtg gcagtggagg gtcgggtagc ggtggttcag gttcggggga agaacttctc   6660
agcaagaatt accacctaga gaacgaagta gcccgcctaa aaagtaggc ggccgcgact    6720 ctagatcata atcagccata ccacatttgt agaggtttta cttgctttaa aaaacctccc   6780
acacctcccc ctgaacctga aacataaaat gaatgcaatt gttgttgtta acttgtttat   6840
tgcagcttat aatggttaca aataaagcaa tagcatcaca aatttcacaa ataaagcatt   6900
tttttcactg cattctagtt gtggtttgtc caaactcatc aatgtatctt aaggcgtaaa   6960
ttgtaagcgt taatatttg ttaaaattcg cgttaaattt tgttaaatc agctcattt      7020 ttaaccaata ggccgaaatc ggcaaaatcc cttataaatc aaaagaatag accgagatag   7080
ggttgagtgt tgttccagtt tggaacaaga gtccactatt aaagaacgtg gactccaacg   7140
tcaaagggcg aaaaaccgtc tatcagggcg atggcccact acgtgaacca tcaccctaat   7200
caagtttttt ggggtcgagg tgccgtaaag cactaaatcg gaaccctaaa gggagccccc   7260
gatttagagc ttgacgggga aagccggcga acgtggcgag aaaggaaggg aagaaagcga   7320
aaggagcggg cgctagggcg ctggcaagtg tagcggtcac gctgcgcgta accaccacac   7380
ccgccgcgct taatgcgccg ctacagggcg cgtcaggtgg cacttttcgg ggaaatgtgc   7440
gcggaacccc tatttgttta tttttctaaa tacattcaaa tatgtatccg ctcatgagac   7500
aataaccctg ataaatgctt caataatatt gaaaaaggaa gagtcctgag gcggaaagaa   7560
ccagctgtgg aatgtgtgtc agttagggtg tggaaagtcc ccaggctccc cagcaggcag   7620
aagtatgcaa agcatgcatc tcaattagtc agcaaccagg tgtggaaagt ccccaggctc   7680
cccagcaggc agaagtatgc aaagcatgca tctcaattag tcagcaacca tagtcccgcc   7740
cctaactccg cccatcccgc ccctaactcc gcccagttcc gcccattctc cgccccatgg   7800
ctgactaatt tttttttattt atgcagaggc cgaggccgcc tcggcctctg agctattcca   7860
gaagtagtga ggaggctttt ttggaggcct aggcttttgc aaagatcgat caagagacag   7920
gatgaggatc gtttcgcatg attgaacaag atggattgca cgcaggttct ccggccgctt   7980
gggtggagag gctattcggc tatgactggg cacaacagac aatcggctgc tctgatgccg   8040
ccgtgttccg gctgtcagcg caggggcgcc cggttctttt tgtcaagacc gacctgtccg   8100
gtgccctgaa tgaactgcaa gacgaggcag cgcggctatc gtggctggcc acgacgggcg   8160
ttccttgcgc agctgtgctc gacgttgtca ctgaagcggg aagggactgg ctgctattgg   8220
gcgaagtgcc ggggcaggat ctcctgtcat ctcaccttgc tcctgccgag aaagtatcca   8280
tcatggctga tgcaatgcgg cggctgcata cgcttgatcc ggctacctgc ccattcgacc   8340
accaagcgaa acatcgcatc gagcgagcac gtactcggat ggaagccggt cttgtcgatc   8400
aggatgatct ggacgaagag catcaggggc tcgcgccagc cgaactgttc gccaggctca   8460
aggcgagcat gcccgacggc gaggatctcg tcgtgaccca tggcgatgcc tgcttgccga   8520
atatcatggt ggaaaatggc cgcttttctg gattcatcga ctgtggccgg ctgggtgtgg   8580
```

```
cggaccgcta tcaggacata gcgttggcta cccgtgatat tgctgaagag cttggcggcg      8640
aatgggctga ccgcttcctc gtgctttacg gtatcgccgc tcccgattcg cagcgcatcg      8700
ccttctatcg ccttcttgac gagttcttct gagcgggact ctggggttcg aaatgaccga      8760
ccaagcgacg cccaacctgc catcacgaga tttcgattcc accgccgcct tctatgaaag      8820
gttgggcttc ggaatcgttt tccgggacgc cggctggatg atcctccagc gcggggatct      8880
catgctggag ttcttcgccc accctagggg gaggctaact gaaacacgga aggagacaat      8940
accggaagga acccgcgcta tgacggcaat aaaaagacag aataaaacgc acggtgttgg      9000
gtcgtttgtt cataaacgcg gggttcggtc ccagggctgg cactctgtcg ataccccacc      9060
gagacccat tggggccaat acgcccgcgt ttcttccttt tccccacccc accccccaag       9120
ttcgggtgaa ggcccagggc tcgcagccaa cgtcggggcg gcaggccctg ccatagcctc      9180
aggttactca tatatacttt agattgattt aaaacttcat ttttaattta aaaggatcta      9240
ggtgaagatc cttttttgata atctcatgac caaaatccct taacgtgagt tttcgttcca     9300
ctgagcgtca gaccccgtag aaaagatcaa aggatcttct tgagatcctt ttttttctgcg     9360
cgtaatctgc tgcttgcaaa caaaaaaacc accgctacca gcggtggttt gtttgccgga     9420
tcaagagcta ccaactcttt ttccgaaggt aactggcttc agcagagcgc agataccaaa     9480
tactgtcctt ctagtgtagc cgtagttagg ccaccacttc aagaactctg tagcaccgcc     9540
tacataccctc gctctgctaa tcctgttacc agtggctgct gccagtggcg ataagtcgtg    9600
tcttaccggg ttggactcaa gacgatagtt accggataag gcgcagcggt cgggctgaac     9660
gggggggttcg tgcacacagc ccagcttgga gcgaacgacc tacaccgaac tgagatacct    9720
acagcgtgag ctatgagaaa gcgccacgct tcccgaaggg agaaaggcgg acaggtatcc     9780
ggtaagcggc agggtcggaa caggagagcg cacgagggag cttccagggg gaaacgcctg     9840
gtatctttat agtcctgtcg ggtttcgcca cctctgactt gagcgtcgat ttttgtgatg     9900
ctcgtcaggg gggcggagcc tatggaaaaa cgccagcaac gcggcctttt tacgttcct     9960
ggccttttgc tggccttttg ctcacatgtt ctttcctgcg ttatcccctg attctgtgga     10020
taaccgtatt accgccatgc at                                              10042
```

<210> SEQ ID NO 11
<211> LENGTH: 14283
<212> TYPE: DNA
<213> ORGANISM: Artificial Sequence
<220> FEATURE:
<223> OTHER INFORMATION: pPlatTET-gRNA2

<400> SEQUENCE: 11

```
tagttattaa tagtaatcaa ttacggggtc attagttcat agcccatata tggagttccg       60
cgttacataa cttacggtaa atggcccgcc tggctgaccg cccaacgacc cccgcccatt      120
gacgtcaata atgacgtatg ttcccatagt aacgccaata gggactttcc attgacgtca      180
atgggtggac tatttacggt aaactgccca cttggcagta catcaagtgt atcatatgcc      240
aagtacgccc cctattgacg tcaatgacgg taaatggccc gcctggcatt atgcccagta      300
catgacctta tgggactttc ctacttggca gtacatctac gtattagtca tcgctattac      360
catgggtcga ggtgagcccc acgttctgct tcactctccc catctccccc cctccccac      420
ccccaatttt gtatttattt attttttaat tattttgtgc agcgatgggg gcgggggggg      480
gggggggcgcg cgccaggcgg ggcggggcgg ggcgagggg ggggcggggc gaggcggaga      540
ggtgcggcgg cagccaatca gagcggcgcg ctccgaaagt ttccttttat ggcgaggcgg      600
```

```
cggcggcggc ggccctataa aaagcgaagc gcgcggcggg cgggagtcgc tgcgttgcct      660
tcgccccgtg ccccgctccg cgccgcctcg cgccgcccgc cccggctctg actgaccgcg      720
ttactcccac aggtgagcgg gcgggacggc ccttctcctc cgggctgtaa ttagcgcttg      780
gtttaatgac ggctcgtttc ttttctgtgg ctgcgtgaaa gccttaaagg ctccgggag       840
ggcccttgt gcgggggga gcggctcggg gggtgcgtgc gtgtgtgtgt gcgtggggag        900
cgccgcgtgc ggcccgcgct gcccggcggc tgtgagcgct gcgggcgcgg cgcgggctt       960
tgtgcgctcc gcgtgtgcgc gaggggagcg cggccggggg cggtgccccg cggtgcgggg     1020
gggctgcgag gggaacaaag gctgcgtgcg gggtgtgtgc gtggggggt gagcaggggg      1080
tgtgggcgcg gcggtcgggc tgtaaccccc ccctgcaccc ccctccccga gttgctgagc     1140
acggcccggc ttcgggtgcg gggctccgtg cggggcgtgg cgcggggctc gccgtgccgg     1200
gcgggggtg gcggcaggtg ggggtgccgg gcggggcggg gccgcctcgg gccggggagg      1260
gctcggggga ggggcgcggc ggccccggag cgccggcggc tgtcgaggcg cggcgagccg     1320
cagccattgc ctttatggt aatcgtgcga gagggcgcag ggacttcctt tgtcccaaat      1380
ctggcggagc cgaaatctgg gaggcgccgc cgcacccct ctagcgggcg cgggcgaagc     1440
ggtgcggcgc cggcaggaag gaaatgggcg gggagggcct tcgtgcgtcg ccgcgccgcc     1500
gtccccttct ccatctccag cctcggggct gccgcagggg gacggctgcc ttcgggggg     1560
acggggcagg gcggggttcg gcttctggcg tgtgaccggc ggctctagag cctctgctaa     1620
ccatgttcat gccttcttct ttttcctaca gctcctgggc aacgtgctgg ttgttgtgct     1680
gtctcatcat tttggcaaag aattcccccg cgatcgcgcc accatgccca agaagaagcg     1740
caaggtggga cgcgtctgca ggatatcaag cttgcggtac cgcggcccg ggatcgccac     1800
catggacaag aagtacagca tcggcctggc catcggcacc aactctgtgg gctgggccgt     1860
gatcaccgac gagtacaagg tgcccagcaa gaaattcaag gtgctgggca acaccgaccg     1920
gcacagcatc aagaagaacc tgatcggcgc cctgctgttc gacagcggag aaacagccga     1980
ggccacccgg ctgaagagaa ccgccagaag aagatacacc agacggaaga accggatctg     2040
ctatctgcaa gagatcttca gcaacgagat ggccaaggtg gacgacagct tcttccacag     2100
actggaagag tccttcctgg tggaagagga taagaagcac gagcggcacc ccatcttcgg     2160
caacatcgtg gacgaggtgg cctaccacga gaagtacccc accatctacc acctgagaaa     2220
gaaactggtg gacagcaccg acaaggccga cctgcggctg atctatctgg ccctggccca     2280
catgatcaag ttccggggcc acttcctgat cgagggcgac ctgaacccg acaacagcga     2340
cgtggacaag ctgttcatcc agctggtgca gacctacaac cagctgttcg aggaaaaccc     2400
catcaacgcc agcggcgtgg acgccaaggc catcctgtct gccagactga gcaagagcag     2460
acggctggaa aatctgatcg cccagctgcc cggcgagaag aagaatggcc tgttcggcaa     2520
cctgattgcc ctgagcctgg gcctgacccc caacttcaag agcaacttcg acctggccga     2580
ggatgccaaa ctgcagctga gcaaggacac ctacgacgac gacctggaca acctgctggc     2640
ccagatcggc gaccagtacg ccgacctgtt tctggccgcc aagaacctgt ccgacgccat     2700
cctgctgagc gacatcctga gtgaacac cgagatcacc aaggcccccc tgagcgcctc     2760
tatgatcaag agatacgacg agcaccacca ggacctgacc ctgctgaaag ctctcgtgcg     2820
gcagcagctg cctgagaagt acaaagagat tttcttcgac cagagcaaga acggctacgc     2880
cggctacatc gatggcggag ccagccagga agagttctac aagttcatca gcccatcct     2940
```

```
ggaaaagatg gacggcaccg aggaactgct cgtgaagctg aacagagagg acctgctgcg   3000
gaagcagcgg accttcgaca acggcagcat cccccaccag atccacctgg agagctgca    3060 cgccattctg cggcggcagg aagattttta cccattcctg aaggacaacc gggaaaagat   3120
cgagaagatc ctgaccttcc gcatccccta ctacgtgggc cctctggcca ggggaaacag   3180
cagattcgcc tggatgacca aaagagcga ggaaaccatc accccctgga acttcgagga    3240
agtggtggac aagggcgcca cgcccagag cttcatcgag cggatgacca acttcgataa    3300
gaacctgccc aacgagaagg tgctgcccaa gcacagcctg ctgtacgagt acttcaccgt   3360
gtacaacgag ctgaccaaag tgaaatacgt gaccgaggga atgagaaagc ccgccttcct   3420
gagcggcgag cagaaaaaag ccatcgtgga cctgctgttc aagaccaacc ggaaagtgac   3480
cgtgaagcag ctgaaagagg actacttcaa gaaaatcgag tgcttcgact ccgtggaaat   3540
ctccggcgtg aagatcggt tcaacgcctc cctgggcaca taccacgatc tgctgaaaat    3600
tatcaaggac aaggacttcc tggacaatga ggaaaacgag acattctgg aagatatcgt    3660 gctgaccctg acactgtttg aggacagaga gatgatcgag gaacggctga aaacctatgc   3720
ccacctgttc gacgacaaag tgatgaagca gctgaagcgg cggagataca ccggctgggg   3780
caggctgagc cggaagctga tcaacggcat ccgggacaag cagtccggca agacaatcct   3840
ggatttcctg aagtccgacg gcttcgccaa cagaaacttc atgcagctga tccacgacga   3900
cagcctgacc tttaaagagg acatccagaa agcccaggtg tccggccagg gcgatagcct   3960
gcacgagcac attgccaatc tggccggcag cccccgccat aagaagggca tcctgcagac   4020
agtgaaggtg gtggacgagc tcgtgaaagt gatgggccgg cacaagcccg agaacatcgt   4080
gatcgaaatg gccagagaga accagaccac ccagaaggga cagaagaaca gccgcgagag   4140
aatgaagcgg atcgaagagg gcatcaaaga gctgggcagc cagatcctga aagaacaccc   4200
cgtggaaaac acccagctgc agaacgagaa gctgtacctg tactacctgc agaatgggcg   4260
ggatatgtac gtgaccagg aactggacat caaccggctg tccgactacg atgtggacgc     4320
tatcgtgcct cagagctttc tgaaggacga ctccatcgat aacaaagtgc tgactcggag   4380
cgacaagaac cgggggcaaga gcgacaacgt gcccctccgaa gaggtcgtga agaagatgaa   4440
gaactactgg cgccagctgc tgaatgccaa gctgattacc cagaggaagt tcgacaatct   4500
gaccaaggcc gagagaggcg gcctgagcga actggataag gccggcttca tcaagagaca   4560
gctggtggaa acccggcaga tcacaaagca cgtggcacag atcctggact cccggatgaa   4620
cactaagtac gacgagaacg acaaactgat ccgggaagtg aaagtgatca ccctgaagtc   4680
caagctggtg tccgatttcc ggaaggattt ccagttttac aaagtgcgcg agatcaacaa   4740
ctaccaccac gcccacgacg cctacctgaa cgccgtcgtg ggaaccgccc tgatcaaaaa   4800
gtaccctaag ctggaaagcg agttcgtgta cggcgactac aaggtgtacg acgtgcggaa   4860
gatgatcgcc aagagcgagc aggaaatcgg caaggctacc gccaagtact tcttctacag   4920
caacatcatg aactttttca agaccgagat taccctggcc aacggcgaga tccggaagcg   4980
gcctctgatc gagacaaacg gcgaaacagg cgagatcgtg tgggataagg gccgggactt   5040
tgccaccgtg cggaaagtgc tgtctatgcc ccaagtgaat atcgtgaaaa agaccgaggt   5100
gcagacaggc ggcttcagca agagtctat cctgcccaag aggaacagcg acaagctgat   5160
cgccagaaag aaggactggg accctaagaa gtacggcggc ttcgacagcc ccaccgtggc   5220
ctattctgtg ctggtggtgg ccaaagtgga aaagggcaag tccaagaaac tgaagagtgt   5280
gaaagagctg ctggggatca ccatcatgga aagaagcagc ttcgagaaga atccccatcga   5340
```

```
ctttctggaa gccaagggct acaaagaagt gaaaaaggac ctgatcatca agctgcctaa      5400
gtactccctg ttcgagctgg aaaacggccg gaagagaatg ctggcctctg ccggcgaact      5460
gcagaaggga aacgaactgg ccctgccctc caaatatgtg aacttcctgt acctggccag      5520
ccactatgag aagctgaagg ctcccccga ggataatgag cagaaacagc tgtttgtgga      5580
acagcacaaa cactacctgg acgagatcat cgagcagatc agcgagttct ccaagagagt      5640
gatcctggcc gacgctaatc tggacaaggt gctgagcgcc tacaacaagc acagagacaa      5700
gcctatcaga gagcaggccg agaatatcat ccacctgttt accctgacca atctgggagc      5760
ccctgccgcc ttcaagtact tgacaccac catcgaccgg aagaggtaca ccagcaccaa      5820
agaggtgctg gacgccaccc tgatccacca gagcatcacc ggcctgtacg agacacggat      5880
cgacctgtct cagctgggag cgacgcctaa tccctatgac gtgcccgatt atgccagcct      5940
gggcagcggc tcccccaaga aaaacgcaa ggtggaagat cctaagaaaa agcggaaagt      6000
ggacggcatt ggtagtggga gcaacggcag cagcggatcc aacggtccga ctgacgccgc      6060
ggaagaggag cttctgagca aaaactatca cctcgaaaac gaggttgcgc gactgaagaa      6120
aggaagcggg tccggtggaa gtggctccgg atctggaggt tctggcagcg gaggtagcgg      6180
cagtggcgaa gagctcctta gtaagaacta tcatctggaa aatgaggtag cgcgcttaaa      6240
gaaagggtcg ggaagtggcg gcagcggaag tgggagtgga gggagcggtt ctggcggttc      6300
cggcagtgga gaggagttgc tgtctaagaa ctaccactta gaaaacgaag tcgcacggct      6360
aaaaaaaggt tccggctccg gcggctccgg ttctggaagc gggggctcgg gatcaggtgg      6420
atctggatca ggagaggaat tgctttccaa aaactaccac cttgagaatg aggtggccag      6480
gttaaagaag gggagcggct cggggggtag tggatcgggg tcgggcgggt caggaagcgg      6540
tggtagcgga tctggggagg agctgctctc gaagaattac catttggaga cgaagtggc      6600 gagactaaag aagggaagcg gtagtggtgg ttcagggtct ggttcaggtg gcagtgggtc      6660
tgggggctca gggtccggga cggccggcct cggaagcgga gctactaact tcagcctgct      6720
gaagcaggct ggagacgtgg aggagaaccc tggacctagt accatgggcc ccgacatcgt      6780
gatgacccag agcccagca gcctgagcgc cagcgtgggc gaccgcgtga ccatcacctg      6840
ccgcagcagc accggcgcc tgaccaccag caactacgcc agctgggtgc aggagaagcc      6900
cggcaagctg ttcaagggcc tgatcggcgg caccaacaac cgcgccccg cgtgcccag      6960 ccgcttcagc ggcagcctga tcggcgacaa ggccaccctg accatcagca gcctgcagcc      7020
cgaggacttc gccacctact tctgcgccct gtggtacagc aaccactggg tgttcggcca      7080
gggcaccaag gtggagctga gcgcggcgg cggcggcagc ggcggcggcg cagcggcgg      7140 cggcggcagc agcggcggcg cagcgaggt gaagctgctg gagagcggcg gcggcctggt      7200
gcagcccggc ggcagcctga gctgagctg cgccgtgagc ggcttcagcc tgaccgacta      7260
cggcgtgaac tgggtgcgcc aggcccccgg ccgcggcctg gagtggatcg gcgtgatctg      7320
gggcgacggc atcaccgact acaacagcgc cctgaaggac cgcttcatca tcagcaagga      7380
caacggcaag aacaccgtgt acctgcagat gagcaaggtg cgcagcgacg acaccgccct      7440
gtactactgc gtgaccggcc tgttcgacta ctggggccag ggcaccctgg tgaccgtgag      7500
cagctaccca tacgatgttc cagattacgc tggtggaggc ggaggttctg ggggaggagg      7560
tagtggcggt ggtggttcag gaggcggcgg aagcttggat ccaggtggag gtggaagcgg      7620
tagcaaagga gaagaacttt tcactggagt tgtcccaatt cttgttgaat tagatggtga      7680
```

```
tgttaatggg cacaaatttt ctgtccgtgg agagggtgaa ggtgatgcta caaacggaaa    7740 actcacccett aaatttattt gcactactgg aaaactacct gttccgtggc aacacttgt    7800 cactactctg acctatggtg ttcaatgctt ttcccgttat ccggatcaca tgaaacggca    7860 tgacttttc aagagtgcca tgcccgaagg ttatgtacag aacgcacta tatctttcaa     7920 agatgacggg acctacaaga cgcgtgctga agtcaagttt gaaggtgata cccttgttaa    7980
tcgtatcgag ttaaagggta ttgattttaa agaagatgga acattcttg gacacaaact    8040 cgagtacaac tttaactcac acaatgtata catcacggca gacaaacaaa gaatggaat    8100 caaagctaac ttcaaaattc gccacaacgt tgaagatggt tccgttcaac tagcagacca    8160
ttatcaacaa aatactccaa ttggcgatgg ccctgtcctt ttaccagaca accattacct    8220
gtcgacacaa tctgtccttt cgaaagatcc aacgaaaag cgtgaccaca tggtccttct    8280
tgagtttgta actgctgctg ggattacaca tggcatggat gagctctaca aggtggagg    8340 tcggaccggt ggcggtggcg gaggggctag cagatccgaa ctgcccacct gcagctgtct    8400
tgatcgagtt atacaaaaag acaaaggccc atattataca caccttgggg caggaccaag    8460
tgttgctgct gtcagggaaa tcatggagaa taggtatggt caaaaaggaa acgcaataag    8520
gatagaaata gtagtgtaca ccggtaaaga agggaaaagc tctcatgggt gtccaattgc    8580
taagtgggtt ttaagaagaa gcagtgatga agaaaaagtt ctttgtttgg tccggcagcg    8640
tacaggccac cactgtccaa ctgctgtgat ggtggtgctc atcatggtgt gggatggcat    8700
ccctcttcca atggccgacc ggctatacac agagctcaca gagaatctaa agtcatacaa    8760 tgggcacct accgacagaa gatgcaccct caatgaaaat cgtacctgta catgtcaagg    8820
aattgatcca gagacttgtg gagcttcatt ctcttttggc tgttcatgga gtatgtactt    8880
taatggctgt aagtttggta gaagcccaag ccccagaaga tttagaattg atccaagctc    8940
tcccttacat gaaaaaaacc ttgaagataa cttacagagt ttggctacac gattagctcc    9000
aatttataag cagtatgctc cagtagctta ccaaaatcag gtggaatatg aaaatgttgc    9060
ccgagaatgt cggcttggca gcaaggaagg tcgtcccttc tctggggtca ctgcttgcct    9120
ggacttctgt gctcatcccc acaggacat tcacaacatg aataatggaa gcactgtggt     9180 ttgtaccta actcgagaag ataaccgctc tttgggtgtt attcctcaag atgagcagct    9240
ccatgtgcta cctctttata agcttttcaga cacagatgag tttggctcca aggaaggaat    9300
ggaagccaag atcaaatctg gggccatcga ggtcctggca ccccgccgca aaaaaagaac    9360
gtgtttcact cagcctgttc cccgttctgg aaagaagagg gctgcgatga tgacagaggt    9420
tcttgcacat aagataaggg cagtggaaaa gaaacctatt ccccgaatca gcggaagaa    9480 taactcaaca acaacaaaca acagtaagcc ttcgtcactg ccaaccttag ggagtaacac    9540
tgagaccgtg caacctgaag taaaaagtga aaccgaaccc cattttatct taaaaagttc    9600
agacaacact aaaaacttatt cgctgatgcc atccgctcct cacccagtga agaggcatc    9660 tccaggcttc tcctggtccc cgaagactgc ttcagccaca ccagctccac tgaagaatga    9720
cgcaacagcc tcatgcgggt tttcagaaag aagcagcact ccccactgta cgatgccttc    9780
gggaagactc agtggtgcca atgcagctgc tgctgatggc cctggcattt cacagcttgg    9840
cgaagtggct cctctccccca ccctgtctgc tcctgtgatg gagcccctca ttaattctga    9900
gccttccact ggtgtgactg agccgctaac gcctcatcag ccaaaccacc agccctcctt    9960
cctcacctct cctcaagacc ttgcctcttc tccaatggaa gaagatgagc agcattctga   10020
agcagatgag cctccatcag acgaaccct atctgatgac cccctgtcac ctgctgagga   10080
```

```
gaaattgccc cacattgatg agtattggtc agacagtgag cacatctttt tggatgcaaa    10140
tattggtggg gtggccatcg cacctgctca cggctcggtt ttgattgagt gtgcccggcg    10200
agagctgcac gctaccactc ctgttgagca ccccaaccgt aatcatccaa cccgcctctc    10260
ccttgtcttt taccagcaca aaaacctaaa taagccccaa catggttttg aactaaacaa    10320
gattaagttt gaggctaaag aagctaagaa taagaaaatg aaggcctcag agcaaaaaga    10380
ccaggcagct aatgaaggtc cagaacagtc ctctgaagta aatgaattga accaaattcc    10440
ttctcataaa gcattaacat taacccatga caatgttgtc accgtgtccc cttatgctct    10500
cacacacgtt gcggggccct ataaccattg ggtctgagcg gccgcgactc tagatcataa    10560
tcagccatac cacatttgta gaggttttac ttgctttaaa aaacctccca cacctccccc    10620
tgaacctgaa acataaaatg aatgcaattg ttgttgttaa cttgtttatt gcagcttata    10680
atggttacaa ataaagcaat agcatcacaa atttcacaaa taaagcattt ttttcactgc    10740
attctagttg tggtttgtcc aaactcatca atgtatcttg gcgcgcctgt acaaaaaagc    10800
aggctttaaa ggaaccaatt cagtcgactg gatccggtac caaggtcggg caggaagagg    10860
gcctatttcc catgattcct tcatatttgc atatacgata caaggctgtt agagagataa    10920
ttagaattaa tttgactgta aacacaaaga tattagtaca aaatacgtga cgtagaaagt    10980
aataatttct gggtagttt gcagttttaa aattatgttt taaatggac tatcatatgc    11040 ttaccgtaac ttgaaagtat ttcgatttct tggctttata tatcttaagt taaaataagg    11100
ctagtccgtt atcaacttga aaaagtggca ccgagtcggt gcttttttc tagacccagc    11160 tttcttgtac aaagttggca ttaggcgcgc caaggcgtaa attgtaagcg ttaatatttt    11220
gttaaaattc gcgttaaatt tttgttaaat cagctcattt tttaaccaat aggccgaaat    11280
cggcaaaatc ccttataaat caaaagaata gaccgagata gggttgagtg ttgttccagt    11340
ttggaacaag agtccactat taagaacgt ggactccaac gtcaaagggc gaaaaaccgt    11400
ctatcagggc gatggcccac tacgtgaacc atcaccctaa tcaagttttt tggggtcgag    11460
gtgccgtaaa gcactaaatc ggaacccaa agggagcccc cgatttagag cttgacgggg    11520
aaagccggcg aacgtggcga gaaaggaagg gaagaaagcg aaaggagcgg gcgctagggc    11580
gctggcaagt gtagcggtca cgctgcgcgt aaccaccaca cccgccgcgc ttaatgcgcc    11640
gctacagggc gcgtcaggtg gcactttttcg gggaaatgtg cgcggaaccc ctatttgttt    11700
atttttctaa atacattcaa atatgtatcc gctcatgaga caataaccct gataaatgct    11760
tcaataatat tgaaaaagga agagtcctga ggcggaaaga accagctgtg gaatgtgtgt    11820
cagttagggt gtggaaagtc cccaggctcc ccagcaggca gaagtatgca aagcatgcat    11880
ctcaattagt cagcaaccag gtgtggaaag tccccaggct ccccagcagg cagaagtatg    11940
caaagcatgc atctcaatta gtcagcaacc atagtcccgc ccctaactcc gcccatcccg    12000
cccctaactc cgcccagttc cgcccattct ccgccccatg ctgactaat tttttttatt    12060 tatgcagagg ccgaggccgc ctcggcctct gagctattcc agaagtagtg aggaggcttt    12120
tttggaggcc taggcttttg caaagatcga tcaagagaca ggatgaggat cgtttcgcat    12180
gattgaacaa gatggattgc acgcaggttc tccggccgct tgggtggaga ggctattcgg    12240
ctatgactgg gcacaacaga caatcggctg ctctgatgcc gccgtgttcc ggctgtcagc    12300
gcaggggcgc ccggttcttt ttgtcaagac cgacctgtcc ggtgccctga atgaactgca    12360
agacgaggca gcgcggctat cgtggctggc cacgacgggc gttccttgcg cagctgtgct    12420
```

```
cgacgttgtc actgaagcgg gaagggactg gctgctattg ggcgaagtgc cggggcagga    12480
tctcctgtca tctcaccttg ctcctgccga gaaagtatcc atcatggctg atgcaatgcg    12540
gcggctgcat acgcttgatc cggctacctg cccattcgac caccaagcga acatcgcat     12600 cgagcgagca cgtactcgga tggaagccgg tcttgtcgat caggatgatc tggacgaaga    12660
gcatcagggg ctcgcgccag ccgaactgtt cgccaggctc aaggcgagca tgcccgacgg    12720
cgaggatctc gtcgtgaccc atggcgatgc ctgcttgccg aatatcatgg tggaaaatgg    12780
ccgcttttct ggattcatcg actgtggccg gctgggtgtg gcggaccgct atcaggacat    12840
agcgttggct acccgtgata ttgctgaaga gcttggcggc gaatgggctg accgcttcct    12900
cgtgctttac ggtatcgccg ctcccgattc gcagcgcatc gccttctatc gccttcttga    12960
cgagttcttc tgagcgggac tctgggttc gaaatgaccg accaagcgac gcccaacctg     13020
ccatcacgag atttcgattc caccgccgcc ttctatgaaa ggttgggctt cggaatcgtt    13080
ttccgggacg ccggctggat gatcctccag cgcggggatc tcatgctgga gttcttcgcc    13140
caccctaggg ggaggctaac tgaaacacgg aaggagacaa taccggaagg aacccgcgct    13200
atgacggcaa taaaaagaca gaataaaacg cacggtgttg ggtcgtttgt tcataaacgc    13260
ggggttcggt cccagggctg gcactctgtc gataccccac cgagacccca ttggggccaa    13320
tacgcccgcg tttcttcctt ttccccaccc cacccccaa gttcgggtga aggcccaggg     13380
ctcgcagcca acgtcgggc ggcaggccct gccatagcct caggttactc atatatactt     13440
tagattgatt taaaacttca ttttttaattt aaaaggatct aggtgaagat ccttttttgat  13500 aatctcatga ccaaaatccc ttaacgtgag ttttcgttcc actgagcgtc agacccccgta   13560 gaaaagatca aggatcttc ttgagatcct ttttttctgc gcgtaatctg ctgcttgcaa     13620
acaaaaaaac caccgctacc agcggtggtt tgtttgccgg atcaagagct accaactctt    13680
tttccgaagg taactggctt cagcagagcg cagataccaa atactgtcct tctagtgtag    13740
ccgtagttag gccaccactt caagaactct gtagcaccgc ctacatacct cgctctgcta    13800
atcctgttac cagtggctgc tgccagtggc gataagtcgt gtcttaccgg gttggactca    13860
agacgatagt taccggataa ggcgcagcgg tcgggctgaa cggggggttc gtgcacacag    13920
cccagcttgg agcgaacgac ctacaccgaa ctgagatacc tacagcgtga gctatgagaa    13980
agcgccacgc ttcccgaagg gagaaaggcg gacaggtatc cggtaagcgg cagggtcgga    14040
acaggagagc gcacgaggga gcttccaggg ggaaacgcct ggtatcttta tagtcctgtc    14100
gggtttcgcc acctctgact tgagcgtcga ttttgtgat gctcgtcagg ggggcggagc     14160
ctatggaaaa acgccagcaa cgcggccttt ttacggttcc tggccttttg ctggcctttt    14220
gctcacatgt tctttcctgc gttatcccct gattctgtgg ataaccgtat taccgccatg    14280
cat                                                                   14283
```

<210> SEQ ID NO 12
<211> LENGTH: 23
<212> TYPE: DNA
<213> ORGANISM: Artificial Sequence
<220> FEATURE:
<223> OTHER INFORMATION: Gfap_1

<400> SEQUENCE: 12
atagacataa tggtcagggg tgg                                                23

<210> SEQ ID NO 13
<211> LENGTH: 23

<212> TYPE: DNA
<213> ORGANISM: Artificial Sequence
<220> FEATURE:
<223> OTHER INFORMATION: Gfap_2

<400> SEQUENCE: 13
ggatgccagg atgtcagccc cgg                                              23

<210> SEQ ID NO 14
<211> LENGTH: 23
<212> TYPE: DNA
<213> ORGANISM: Artificial Sequence
<220> FEATURE:
<223> OTHER INFORMATION: Gfap_3

<400> SEQUENCE: 14
atatggcaag ggcagccccg tgg                                              23

<210> SEQ ID NO 15
<211> LENGTH: 23
<212> TYPE: DNA
<213> ORGANISM: Artificial Sequence
<220> FEATURE:
<223> OTHER INFORMATION: H19DMR_1

<400> SEQUENCE: 15
gtgggggggc tctttaggtt tgg                                              23

<210> SEQ ID NO 16
<211> LENGTH: 23
<212> TYPE: DNA
<213> ORGANISM: Artificial Sequence
<220> FEATURE:
<223> OTHER INFORMATION: H19DMR_2

<400> SEQUENCE: 16
accctggtct ttacacacaa agg                                              23

<210> SEQ ID NO 17
<211> LENGTH: 23
<212> TYPE: DNA
<213> ORGANISM: Artificial Sequence
<220> FEATURE:
<223> OTHER INFORMATION: H19DMR_3

<400> SEQUENCE: 17
gaagctgtta tgtgcaacaa ggg                                              23

<210> SEQ ID NO 18
<211> LENGTH: 23
<212> TYPE: DNA
<213> ORGANISM: Artificial Sequence
<220> FEATURE:
<223> OTHER INFORMATION: H19DMR_4

<400> SEQUENCE: 18
cagatttggc tatagctaaa tgg                                              23

<210> SEQ ID NO 19
<211> LENGTH: 20
<212> TYPE: DNA
<213> ORGANISM: Artificial Sequence
<220> FEATURE:
<223> OTHER INFORMATION: UR_1

<400> SEQUENCE: 19

```
ccattattgc attaatctga                                          20

<210> SEQ ID NO 20
<211> LENGTH: 20
<212> TYPE: DNA
<213> ORGANISM: Artificial Sequence
<220> FEATURE:
<223> OTHER INFORMATION: UR_2

<400> SEQUENCE: 20
taatgcagcc agaaaatgac                                          20

<210> SEQ ID NO 21
<211> LENGTH: 20
<212> TYPE: DNA
<213> ORGANISM: Artificial Sequence
<220> FEATURE:
<223> OTHER INFORMATION: UR_3

<400> SEQUENCE: 21
tcagggatca aattctgagc                                          20

<210> SEQ ID NO 22
<211> LENGTH: 25
<212> TYPE: DNA
<213> ORGANISM: Artificial Sequence
<220> FEATURE:
<223> OTHER INFORMATION: GfapSTAT3-B3

<400> SEQUENCE: 22
ttggttagtt tttaggattt ttttt                                    25

<210> SEQ ID NO 23
<211> LENGTH: 26
<212> TYPE: DNA
<213> ORGANISM: Artificial Sequence
<220> FEATURE:
<223> OTHER INFORMATION: GfapSTAT3-B4

<400> SEQUENCE: 23
aaaacttcaa acccatctat ctcttc                                   26

<210> SEQ ID NO 24
<211> LENGTH: 25
<212> TYPE: DNA
<213> ORGANISM: Artificial Sequence
<220> FEATURE:
<223> OTHER INFORMATION: H19DMR-B1

<400> SEQUENCE: 24
aaggagatta tgttttattt ttgga                                    25

<210> SEQ ID NO 25
<211> LENGTH: 25
<212> TYPE: DNA
<213> ORGANISM: Artificial Sequence
<220> FEATURE:
<223> OTHER INFORMATION: H19DMR-B2

<400> SEQUENCE: 25
aaaaaaactc aatcaattac aatcc                                    25

<210> SEQ ID NO 26
<211> LENGTH: 28
<212> TYPE: DNA
<213> ORGANISM: Artificial Sequence
```

```
<220> FEATURE:
<223> OTHER INFORMATION: Gfap_O1B1

<400> SEQUENCE: 26
ttgtaaaggt aggattaata agggaatt                                          28

<210> SEQ ID NO 27
<211> LENGTH: 26
<212> TYPE: DNA
<213> ORGANISM: Artificial Sequence
<220> FEATURE:
<223> OTHER INFORMATION: Gfap_O1B2

<400> SEQUENCE: 27
aaaaaaaacc cttcaaaaaa aatcta                                            26

<210> SEQ ID NO 28
<211> LENGTH: 25
<212> TYPE: DNA
<213> ORGANISM: Artificial Sequence
<220> FEATURE:
<223> OTHER INFORMATION: Gfap_O2B1

<400> SEQUENCE: 28
ttattattta tatttggagg gaggg                                             25

<210> SEQ ID NO 29
<211> LENGTH: 25
<212> TYPE: DNA
<213> ORGANISM: Artificial Sequence
<220> FEATURE:
<223> OTHER INFORMATION: Gfap_O2B2

<400> SEQUENCE: 29
attacaccaa aaaaatttta aaaac                                             25

<210> SEQ ID NO 30
<211> LENGTH: 25
<212> TYPE: DNA
<213> ORGANISM: Artificial Sequence
<220> FEATURE:
<223> OTHER INFORMATION: Gfap_O3B1

<400> SEQUENCE: 30
tttaaatttt tttatgtgaa tatgg                                             25

<210> SEQ ID NO 31
<211> LENGTH: 25
<212> TYPE: DNA
<213> ORGANISM: Artificial Sequence
<220> FEATURE:
<223> OTHER INFORMATION: Gfap_O3B2

<400> SEQUENCE: 31
aaacatttaa ttcattaata cacac                                             25

<210> SEQ ID NO 32
<211> LENGTH: 25
<212> TYPE: DNA
<213> ORGANISM: Artificial Sequence
<220> FEATURE:
<223> OTHER INFORMATION: GfapSTAT3-B1

<400> SEQUENCE: 32
gttgaagatt tggtagtgtt gagtt                                             25
```

<210> SEQ ID NO 33
<211> LENGTH: 25
<212> TYPE: DNA
<213> ORGANISM: Artificial Sequence
<220> FEATURE:
<223> OTHER INFORMATION: GfapSTAT3-B2

<400> SEQUENCE: 33
taaaacatat aacaaaaaca ccccc                                         25

<210> SEQ ID NO 34
<211> LENGTH: 26
<212> TYPE: DNA
<213> ORGANISM: Artificial Sequence
<220> FEATURE:
<223> OTHER INFORMATION: H19DMR-B3

<400> SEQUENCE: 34
gggttttttt ggttattgaa ttttaa                                        26

<210> SEQ ID NO 35
<211> LENGTH: 26
<212> TYPE: DNA
<213> ORGANISM: Artificial Sequence
<220> FEATURE:
<223> OTHER INFORMATION: H19DMR-B4

<400> SEQUENCE: 35
aatacacaca tcttaccacc cctata                                        26

<210> SEQ ID NO 36
<211> LENGTH: 25
<212> TYPE: DNA
<213> ORGANISM: Artificial Sequence
<220> FEATURE:
<223> OTHER INFORMATION: H19DMR-B5

<400> SEQUENCE: 36
tttttgggta gttttttttag ttttg                                        25

<210> SEQ ID NO 37
<211> LENGTH: 28
<212> TYPE: DNA
<213> ORGANISM: Artificial Sequence
<220> FEATURE:
<223> OTHER INFORMATION: H19DMR-B6

<400> SEQUENCE: 37
acacaaatac ctaatccctt tattaaac                                      28

<210> SEQ ID NO 38
<211> LENGTH: 23
<212> TYPE: DNA
<213> ORGANISM: Artificial Sequence
<220> FEATURE:
<223> OTHER INFORMATION: off target 1

<400> SEQUENCE: 38
gtgacacagg atgtcagccc ggg                                           23

<210> SEQ ID NO 39
<211> LENGTH: 23
<212> TYPE: DNA
<213> ORGANISM: Artificial Sequence
<220> FEATURE:
<223> OTHER INFORMATION: off target 2

<400> SEQUENCE: 39
ccatgctggg atgtcagccc tgg                                                23

<210> SEQ ID NO 40
<211> LENGTH: 23
<212> TYPE: DNA
<213> ORGANISM: Artificial Sequence
<220> FEATURE:
<223> OTHER INFORMATION: off target 3

<400> SEQUENCE: 40
gtcaccttgg atgtcagccc cgg                                                23

<210> SEQ ID NO 41
<211> LENGTH: 9243
<212> TYPE: DNA
<213> ORGANISM: Artificial Sequence
<220> FEATURE:
<223> OTHER INFORMATION: pCAG-scFvGCN4sfGFPDnmt3bF

<400> SEQUENCE: 41

```
tagttattaa tagtaatcaa ttacggggtc attagttcat agcccatata tggagttccg        60
cgttacataa cttacggtaa atggcccgcc tggctgaccg cccaacgacc cccgcccatt       120
gacgtcaata atgacgtatg ttcccatagt aacgccaata gggactttcc attgacgtca       180
atgggtggac tatttacggt aaactgccca cttggcagta catcaagtgt atcatatgcc       240
aagtacgccc cctattgacg tcaatgacgg taaatggccc gcctggcatt atgcccagta       300
catgacctta tgggactttc ctacttggca gtacatctac gtattagtca tcgctattac       360
catggtcga ggtgagcccc acgttctgct tcactctccc catctccccc cctccccac        420
ccccaatttt gtatttattt attttttaat tattttgtgc agcgatgggg gcggggggg        480
gggggcgcg cgccaggcgg ggcggggcgg ggcgagggc ggggcgggc gaggcggaga          540
ggtgcggcgg cagccaatca gagcggcgcg ctccgaaagt ttccttttat ggcgaggcgg       600
cggcggcggc ggccctataa aaagcgaagc gcgcggcggg cgggagtcgc tgcgttgcct       660
tcgccccgtg ccccgctccg cgccgcctcg cgccgcccgc cccggctctg actgaccgcg       720
ttactcccac aggtgagcgg gcgggacggc ccttctcctc cgggctgtaa ttagcgcttg       780
gtttaatgac ggctcgtttc ttttctgtgg ctgcgtgaaa gccttaaagg ctccggggag       840
ggccctttgt gcggggggga gcggctcggg gggtgcgtgc gtgtgtgtgt gcgtggggag       900
cgccgcgtgc ggcccgcgct gcccggcggc tgtgagcgct gcgggcgcgg cgcggggctt       960
tgtgcgctcc gcgtgtgcgc gaggggagcg cggccggggg cggtgccccg cggtgcgggg      1020
gggctgcgag gggaacaaag gctgcgtgcg gggtgtgtgc gtgggggggt gagcaggggg      1080
tgtgggcgcg gcggtcgggc tgtaaccccc cctgcacccc cctccccga gttgctgagc       1140
acggcccggc ttcgggtgcg gggctccgta cggggcgtgg cgcggggctc gccgtgccgg      1200
gcggggggtg gcggcaggtg ggggtgccgg gcggggcggg gccgcctcgg gccggggagg      1260
gctcggggga ggggcgcggc ggccccggag cgcggcggc tgtcgaggcg cggcgagccg      1320
cagccattgc cttttatggt aatcgtgcga gagggcgcag ggacttcctt tgtcccaaat      1380
ctggcggagc cgaaatctgg gaggcgccgc cgcacccct ctagcgggcg cgggcgaagc      1440
ggtgcggcgc cggcaggaag gaaatggcg gggaggcct cgtgcgtcg ccgcgccgcc        1500
gtccccttct ccatctccag cctcggggct gccgcagggg gacggctgcc ttcggggggg      1560
```

```
acggggcagg gcggggttcg gcttctggcg tgtgaccggc ggctctagag cctctgctaa    1620
ccatgttcat gccttcttct ttttcctaca gctcctgggc aacgtgctgg ttgttgtgct    1680
gtctcatcat tttggcaaag aattctgcag tcgacggtac catgggcccc gacatcgtga    1740
tgacccagag ccccagcagc ctgagcgcca gcgtgggcga ccgcgtgacc atcacctgcc    1800
gcagcagcac cggcgccgtg accaccagca actacgccag ctgggtgcag agaagcccg    1860
gcaagctgtt caagggcctg atcggcggca ccaacaaccg cgcccccggc gtgcccagcc    1920
gcttcagcgg cagcctgatc ggcgacaagg ccaccctgac catcagcagc ctgcagcccg    1980
aggacttcgc cacctacttc tgcgccctgt ggtacagcaa ccactgggtg ttcggccagg    2040
gcaccaaggt ggagctgaag cgcggcggcg gcggcagcgg cggcggcggc agcggcggcg    2100
gcggcagcag cggcggcggc agcgaggtga agctgctgga gagcggcggc ggcctggtgc    2160
agcccggcgg cagcctgaag ctgagctgcg ccgtgagcgg cttcagcctg accgactacg    2220
gcgtgaactg ggtgcgccag gcccccggcc gcggcctgga gtggatcggc gtgatctggg    2280
gcgacggcat caccgactac aacagcgccc tgaaggaccg cttcatcatc agcaaggaca    2340
acggcaagaa caccgtgtac ctgcagatga gcaaggtgcg cagcgacgac accgccctgt    2400
actactgcgt gaccggcctg ttcgactact ggggccaggg caccctggtg accgtgagca    2460
gctacccata cgatgttcca gattacgctg tggaggcgg aggttctggg ggaggaggta    2520
gtggcggtgg tggttcagga ggcggcggaa gcttggatcc aggtggaggt ggaagcggta    2580
gcaaaggaga agaactttc actggagttg tcccaattct tgttgaatta gatggtgatg    2640
ttaatgggca caaattttct gtccgtggag agggtgaagg tgatgctaca aacgaaaaac    2700
tcacccttaa atttatttgc actactggaa aactacctgt tccgtggcca cacttgtca    2760
ctactctgac ctatggtgtt caatgctttt cccgttatcc ggatcacatg aaacggcatg    2820
acttttcaa gagtgccatg cccgaaggtt atgtacagga acgcactata tctttcaaag    2880
atgacgggac ctacaagacg cgtgctgaag tcaagtttga aggtgatacc cttgttaatc    2940
gtatcgagtt aaagggtatt gattttaaag aagatggaaa cattcttgga cacaaactcg    3000
agtacaactt taactcacac aatgtataca tcacggcaga caaacaaaag aatggaatca    3060
aagctaactt caaaattcgc cacaacgttg aagatggttc cgttcaacta gcagaccatt    3120
atcaacaaaa tactccaatt ggcgatggcc ctgtccttt accagacaac cattacctgt    3180
cgacacaatc tgtcctttcg aaagatccca acgaaaagcg tgaccacatg gtccttcttg    3240
agtttgtaac tgctgctggg attacacatg gcatggatga actctacaaa ggtggaggtc    3300
ggaccggtgg cggtggcgga ggggctagca tgaagggaga cagcagacat ctgaatgaag    3360
aagagggtgc cagcgggtat gaggagtgca ttatcgttaa tgggaacttc agtgaccagt    3420
cctcagacac gaaggatgct ccctcacccc cagtcttgga ggcaatctgc acagagccag    3480
tctgcacacc agagaccaga ggccgcaggt caagctcccg gctgtctaag agggaggtct    3540
ccagccttct gaattacacg caggacatga caggagatgg agacagagat gatgaagtag    3600
atgatgggaa tggctctgat attctaatgc aaagctcac ccgtgagacc aaggacacca    3660
gacgcgctc tgaaagcccg ctgtccgaa cccgacatag caatgggacc tccagcttgg    3720
agaggcaaag agcctccccc agaatcaccc gaggtcggca gggccgccac catgtgcagg    3780
agtaccctgt ggagtttccg gctaccaggt ctcggagacg tcgagcatca tcttcagcaa    3840
gcacgccatg gtcatcccct gccagcgtcg acttcatgga agaagtgaca cctaagagcg    3900
tcagtacccc atcagttgac ttgagccagg atggagatca ggagggtatg gataccacac    3960
```

```
aggtggatgc agagagcaga gatggagaca gcacagagta tcaggatgat aaagagtttg    4020
gaataggtga cctcgtgtgg ggaaagatca agggcttctc ctggtggcct gccatggtgg    4080
tgtcctggaa agccacctcc aagcgacagg ccatgcccgg aatgcgctgg gtacagtggt    4140
ttggtgatgg caagttttct gagatctctg ctgacaaact ggtggctctg ggctgttca    4200 gccagcactt taatctggct accttcaata agctggtttc ttataggaag gccatgtacc    4260
acactctgga gaaagccagg gttcgagctg caagaccttc tccagcagt cctggagagt    4320 cactggagga ccagctgaag cccatgctgg agtgggccca cggtggcttc aagcctactg    4380
ggatcgaggg cctcaaaccc aacaagaagc aaccagtggt taataagtcg aaggtgcgtc    4440
gttcagacag taggaactta gaacccagga gacgcgagaa caaaagtcga agacgcacaa    4500
ccaatgactc tgctgcttct gagtcccccc cacccaagcg cctcaagaca aatagctatg    4560
gcgggaagga ccgaggggag gatgaggaga gccgagaacg gatggcttct gaagtcacca    4620
acaacaaggg caatctggaa gaccgctgtt tgtcctgtgg aaagaagaac cctgtgtcct    4680 tccacccct ctttgagggt gggctctgtc agagttgccg ggatcgcttc ctagagctct    4740
tctacatgta tgatgaggac ggctatcagt cctactgcac cgtgtgctgt gagggccgtg    4800
aactgctgct gtgcagtaac acaagctgct gcagatgctt ctgtgtggag tgtctggagg    4860
tgctggtggg cgcaggcaca gctgaggatg ccaagctgca ggaaccctgg agctgctata    4920
tgtgcctccc tcagcgctgc catggggtcc tccgacgcag gaaagattgg aacatgcgcc    4980
tgcaagactt cttcactact gatcctgacc tggaagaatt tgagccaccc aagttgtacc    5040
cagcaattcc tgcagccaaa aggaggccca ttagagtcct gtctctgttt gatggaattg    5100
caacggggta cttggtgctc aaggagttgg gtattaaagt ggaaaagtac attgcctccg    5160
aagtctgtgc agagtccatc gctgtgggaa ctgttaagca tgaaggccag atcaaatatg    5220
tcaatgacgt ccggaaaatc accaagaaaa atattgaaga gtgggcccg ttcgacttgg    5280 tgattggtgg aagcccatgc aatgatctct ctaacgtcaa tcctgcccgc aaaggtttat    5340
atgagggcac aggaaggctc ttcttcgagt tttaccactt gctgaattat acccgcccca    5400
aggagggcga caaccgtcca ttcttctgga tgttcgagaa tgttgtggcc atgaaagtga    5460
atgacaagaa agacatctca agattcctgg catgtaaccc agtgatgatc gatgccatca    5520
aggtgtctgc tgctcacagg gcccggtact tctggggtaa cctacccgga atgaacaggc    5580
ccgtgatggc ttcaaagaat gataagctcg agctgcagga ctgcctggag ttcagtagga    5640
cagcaaagtt aaagaaagtg cagacaataa ccaccaagtc gaactccatc agacagggca    5700
aaaaccagct tttccctgta gtcatgaatg caaggacga cgttttgtgg tgcactgagc    5760
tcgaaaggat cttcggcttc cctgctcact acacggacgt gtccaacatg ggccgcggcg    5820
cccgtcagaa gctgctgggc aggtcctgga gtgtaccggt catcagacac ctgtttgccc    5880
ccttgaagga ctactttgcc tgtgaatagg cggccgcgac tctagatcat aatcagccat    5940
accacatttg tagaggtttt acttgcttta aaaaacctcc cacacctccc cctgaacctg    6000
aaacataaaa tgaatgcaat tgttgttgtt aacttgttta ttgcagctta taatggttac    6060
aaataaagca atagcatcac aaatttcaca aataaagcat ttttttcact gcattctagt    6120
tgtggtttgt ccaaactcat caatgtatct taaggcgtaa attgtaagcg ttaatatttt    6180
gttaaaattc gcgttaaatt tttgttaaat cagctcattt tttaaccaat aggccgaaat    6240
cggcaaaatc ccttataaat caaaagaata gaccgagata gggttgagtg ttgttccagt    6300
```

```
ttggaacaag agtccactat taaagaacgt ggactccaac gtcaagggc gaaaaaccgt    6360
ctatcagggc gatggcccac tacgtgaacc atcaccctaa tcaagttttt tggggtcgag   6420
gtgccgtaaa gcactaaatc ggaaccctaa agggagcccc cgatttagag cttgacgggg   6480
aaagccggcg aacgtggcga gaaaggaagg gaagaaagcg aaaggagcgg gcgctagggc   6540
gctggcaagt gtagcggtca cgctgcgcgt aaccaccaca cccgccgcgc ttaatgcgcc   6600
gctacagggc gcgtcaggtg gcacttttcg gggaaatgtg cgcggaaccc ctatttgttt   6660
attttctaa atacattcaa atatgtatcc gctcatgaga caataaccct gataaatgct    6720
tcaataatat tgaaaaagga agagtcctga ggcggaaaga accagctgtg gaatgtgtgt   6780
cagttagggt gtggaaagtc cccaggctcc ccagcaggca gaagtatgca aagcatgcat   6840
ctcaattagt cagcaaccag gtgtggaaag tccccaggct ccccagcagg cagaagtatg   6900
caaagcatgc atctcaatta gtcagcaacc atagtcccgc ccctaactcc gcccatcccg   6960
cccctaactc cgcccagttc cgcccattct ccgcccatg gctgactaat ttttttatt     7020
tatgcagagg ccgaggccgc ctcggcctct gagctattcc agaagtagtg aggaggcttt   7080
tttggaggcc taggcttttg caaagatcga tcaagagaca ggatgaggat cgtttcgcat   7140
gattgaacaa gatggattgc acgcaggttc tccggccgct tgggtggaga ggctattcgg   7200
ctatgactgg gcacaacaga caatcggctg ctctgatgcc gccgtgttcc ggctgtcagc   7260
gcaggggcgc ccggttcttt ttgtcaagac cgacctgtcc ggtgccctga atgaactgca   7320
agacgaggca gcgcggctat cgtggctggc cacgacgggc gttccttgcg cagctgtgct   7380
cgacgttgtc actgaagcgg gaagggactg gctgctattg ggcgaagtgc ggggcagga   7440
tctcctgtca tctcaccttg ctcctgccga aaagtatcc atcatggctg atgcaatgcg   7500
gcggctgcat acgcttgatc cggctacctg cccattcgac caccaagcga acatcgcat   7560
cgagcgagca cgtactcgga tggaagccgg tcttgtcgat caggatgatc tggacgaaga   7620
gcatcagggg ctcgcgccag ccgaactgtt cgccaggctc aaggcgagca tgcccgacgg   7680
cgaggatctc gtcgtgaccc atggcgatgc ctgcttgccg aatatcatgg tggaaaatgg   7740
ccgcttttct ggattcatcg actgtggccg gctgggtgtg gcggaccgct atcaggacat   7800
agcgttggct acccgtgata ttgctgaaga gcttggcggc gaatgggctg accgcttcct   7860
cgtgctttac ggtatcgccg ctcccgattc gcagcgcatc gccttctatc gccttcttga   7920
cgagttcttc tgagcgggac tctggggttc gaaatgaccg accaagcgac gcccaacctg   7980
ccatcacgag atttcgattc caccgccgcc ttctatgaaa ggttgggctt cggaatcgtt   8040
ttccgggacg ccggctggat gatcctccag cgcggggatc tcatgctgga gttcttcgcc   8100
cacccctaggg ggaggctaac tgaaacacgg aaggagacaa taccggaagg aacccgcgct  8160
atgacggcaa taaaaagaca gaataaaacg cacggtgttg ggtcgtttgt tcataaacgc   8220
ggggttcggt cccagggctg gcactctgtc gataccccac cgagacccca ttggggccaa   8280
tacgcccgcg tttcttcctt ttccccaccc caccccccaa gttcgggtga aggcccaggg   8340
ctcgcagcca acgtcgggc ggcaggccct gccatagcct caggttactc atatatactt    8400
tagattgatt taaaacttca ttttttaattt aaaaggatct aggtgaagat ccttttttgat 8460
aatctcatga ccaaaatccc ttaacgtgag ttttcgttcc actgagcgtc agaccccgta   8520
gaaaagatca aaggatcttc ttgagatcct ttttttctgc gcgtaatctg ctgcttgcaa   8580
acaaaaaaac caccgctacc agcggtggtt tgtttgccgg atcaagagct accaactctt   8640
tttccgaagg taactggctt cagcagagcg cagataccaa atactgtcct tctagtgtag   8700
```

| | |
|---|---:|
| ccgtagttag gccaccactt caagaactct gtagcaccgc ctacatacct cgctctgcta | 8760 |
| atcctgttac cagtggctgc tgccagtggc gataagtcgt gtcttaccgg gttggactca | 8820 |
| agacgatagt taccggataa ggcgcagcgg tcgggctgaa cggggggttc gtgcacacag | 8880 |
| cccagcttgg agcgaacgac ctacaccgaa ctgagatacc tacagcgtga gctatgagaa | 8940 |
| agcgccacgc ttcccgaagg gagaaaggcg gacaggtatc cggtaagcgg cagggtcgga | 9000 |
| acaggagagc gcacgaggga gcttccaggg ggaaacgcct ggtatcttta tagtcctgtc | 9060 |
| gggtttcgcc acctctgact tgagcgtcga ttttttgtgat gctcgtcagg ggggcggagc | 9120 |
| ctatggaaaa acgccagcaa cgcggccttt ttacggttcc tggccttttg ctggccttt | 9180 |
| gctcacatgt tctttcctgc gttatcccct gattctgtgg ataaccgtat taccgccatg | 9240 |
| cat | 9243 |

<210> SEQ ID NO 42
<211> LENGTH: 9264
<212> TYPE: DNA
<213> ORGANISM: Artificial Sequence
<220> FEATURE:
<223> OTHER INFORMATION: pCAG-scFvGCN4sfGFPDnmt3bFNLS

<400> SEQUENCE: 42

| | |
|---|---:|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggac tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catgggtcga ggtgagcccc acgttctgct tcactctccc catctccccc ccctccccac | 420 |
| ccccaatttt gtatttattt attttttaat tattttgtgc agcgatgggg gcggggggg | 480 |
| gggggcgcg cgccaggcgg ggcggggcgg ggcgagggc ggggcgggc gaggcggaga | 540 |
| ggtgcggcgg cagccaatca gagcggcgcg ctccgaaagt ttcctttat ggcgaggcgg | 600 |
| cggcggcggc ggccctataa aaagcgaagc gcgcggcggg cgggagtcgc tgcgttgcct | 660 |
| tcgccccgtg ccccgctccg cgccgcctcg cgccgcccgc cccggctctg actgaccgcg | 720 |
| ttactcccac aggtgagcgg gcgggacggc ccttctcctc cgggctgtaa ttagcgcttg | 780 |
| gtttaatgac ggctcgtttc ttttctgtgg ctgcgtgaaa gccttaaagg gctccggag | 840 |
| ggccctttgt gcgggggga gcggctcggg gggtgcgtgc gtgtgtgtgt gcgtggggag | 900 |
| cgccgcgtgc ggcccgcgct gcccggcggc tgtgagcgct gcgggcgcgg cgcggggctt | 960 |
| tgtgcgctcc gcgtgtgcgc gaggggagcg cggccggggg cggtgccccg cggtgcgggg | 1020 |
| gggctgcgag gggaacaaag gctgcgtgcg gggtgtgtgc gtggggggt gagcagggg | 1080 |
| tgtgggcgcg gcggtcgggc tgtaaccccc ccctgcaccc ccctccccga gttgctgagc | 1140 |
| acggcccggc ttcgggtgcg gggctccgtg cggggcgtgg cgcggggctc gccgtgccgg | 1200 |
| gcgggggtg gcgcaggtg ggggtgccgg gcggggcggg gccgctcgg gccggggagg | 1260 |
| gctcggggga ggggcgcggc ggccccggag cgccggcggc tgtcgaggcg cggcgagccg | 1320 |
| cagccattgc cttttatggt aatcgtgcga gaggggcgcag ggacttcctt tgtcccaaat | 1380 |
| ctggcggagc cgaaatctgg gaggcgccgc cgcacccct ctagcgggcg cgggcgaagc | 1440 |

```
ggtgcggcgc cggcaggaag gaaatgggcg gggagggcct tcgtgcgtcg ccgcgccgcc    1500
gtccccttct ccatctccag cctcggggct gccgcagggg gacggctgcc ttcgggggg     1560 acggggcagg gcggggttcg gcttctggcg tgtgaccggc ggctctagag cctctgctaa    1620
ccatgttcat gccttcttct ttttcctaca gctcctgggc aacgtgctgg ttgttgtgct    1680
gtctcatcat tttggcaaag aattctgcag tcgacggtac catgggcccc gacatcgtga    1740
tgacccagag ccccagcagc ctgagcgcca gcgtgggcga ccgcgtgacc atcacctgcc    1800
gcagcagcac cggcgccgtg accaccagca actacgccag ctgggtgcag agaagcccg    1860 gcaagctgtt caagggcctg atcggcggca ccaacaaccg cgcccccggc gtgcccagcc    1920
gcttcagcgg cagcctgatc ggcgacaagg ccaccctgac catcagcagc ctgcagcccg    1980
aggacttcgc cacctacttc tgcgccctgt ggtacagcaa ccactgggtg ttcggccagg    2040
gcaccaaggt ggagctgaag cgcggcggcg gcggcagcgg cggcggcggc agcggcggcg    2100
gcggcagcag cggcggcggc agcgaggtga agctgctgga gagcggcggc ggcctggtgc    2160
agcccggcgg cagcctgaag ctgagctgcg ccgtgagcgg cttcagcctg accgactacg    2220
gcgtgaactg ggtgcgccag gcccccggcc gcggcctgga gtggatcggc gtgatctggg    2280
gcgacggcat caccgactac aacagcgccc tgaaggaccg cttcatcatc agcaaggaca    2340
acggcaagaa caccgtgtac ctgcagatga gcaaggtgcg cagcgacgac accgccctgt    2400
actactgcgt gaccggcctg ttcgactact ggggccaggg caccctggtg accgtgagca    2460
gctacccata cgatgttcca gattacgctg gtggaggcgg aggttctggg ggaggaggta    2520
gtggcggtgg tggttcagga ggcggcggaa gcttggatcc aggtggaggt ggaagcggta    2580
gcaaaggaga agaactttc actggagttg tcccaattct tgttgaatta gatggtgatg    2640
ttaatgggca caattttct gtccgtggag agggtgaagg tgatgctaca aacggaaaac    2700
tcacccttaa atttatttgc actactggaa aactacctgt tccgtggcca cacttgtca    2760 ctactctgac ctatggtgtt caatgctttt cccgttatcc ggatcacatg aaacggcatg    2820 acttttcaa gagtgccatg cccgaaggtt atgtacagga acgcactata tctttcaaag    2880
atgacgggac ctacaagacg cgtgctgaag tcaagtttga aggtgatacc cttgttaatc    2940
gtatcgagtt aaagggtatt gattttaaag aagatggaaa cattcttgga cacaaactcg    3000
agtacaactt taactcacac aatgtataca tcacggcaga caaacaaaag aatggaatca    3060
aagctaactt caaaattcgc cacaacgttg aagatggttc cgttcaacta gcagaccatt    3120
atcaacaaaa tactccaatt ggcgatggcc ctgtcctttt accagacaac cattacctgt    3180
cgacacaatc tgtcctttcg aaagatccca acgaaaagcg tgaccacatg gtccttcttg    3240
agtttgtaac tgctgctggg attacacatg gcatggatga gctctacaaa ggtgaggtc    3300 ggaccggtgg cggtggcgga ggggctagca tgaagggaga cagcagacat ctgaatgaag    3360
aagagggtgc cagcgggtat gaggagtgca ttatcgttaa tgggaacttc agtgaccagt    3420
cctcagacac gaaggatgct ccctcacccc cagtcttgga ggcaatctgc acagagccag    3480
tctgcacacc agagaccaga ggccgcaggt caagctcccg gctgtctaag agggaggtct    3540
ccagccttct gaattacacg caggacatga caggagatgg agacagagat gatgaagtag    3600
atgatgggaa tggctctgat attctaatgc aaaagctcac ccgtgagacc aaggacacca    3660
ggacgcgctc tgaaagcccg ctgtccgaa cccgacatag caatgggacc tccagcttgg    3720
agaggcaaag agcctccccc agaatcaccc gaggtcggca gggccgccac catgtgcagg    3780
agtaccctgt ggagtttccg gctaccaggt ctcggagacg tcgagcatca tcttcagcaa    3840
```

```
gcacgccatg gtcatcccct gccagcgtcg acttcatgga agaagtgaca cctaagagcg    3900
tcagtacccc atcagttgac ttgagccagg atggagatca ggagggtatg ataccacac     3960 aggtggatgc agagagcaga gatggagaca gcacagagta tcaggatgat aaagagtttg    4020
gaataggtga cctcgtgtgg ggaaagatca agggcttctc ctggtggcct gccatggtgg    4080
tgtcctggaa agccacctcc aagcgacagg ccatgcccgg aatgcgctgg gtacagtggt    4140
ttggtgatgg caagttttct gagatctctg ctgacaaact ggtggctctg ggctgttca     4200 gccagcactt taatctggct accttcaata agctggtttc ttataggaag gccatgtacc    4260
acactctgga gaaagccagg gttcgagctg caagaccttc tccagcagt cctggagagt     4320 cactggagga ccagctgaag cccatgctgg agtgggccca cggtggcttc aagcctactg    4380
ggatcgaggc cctcaaaccc aacaagaagc aaccagtggt taataagtcg aaggtgcgtc    4440
gttcagacag taggaactta gaacccagga gacgcgagaa caaaagtcga agacgcacaa    4500
ccaatgactc tgctgcttct gagtcccccc cacccaagcg cctcaagaca aatagctatg    4560
gcgggaagga ccgaggggag gatgaggaga gccgagaacg gatggcttct gaagtcacca    4620
acaacaaggg caatctggaa gaccgctgtt gtgcctgtgg aaagaagaac cctgtgtcct    4680 tccacccct ctttgagggt gggctctgtc agagttgccg ggatcgcttc ctagagctct     4740
tctacatgta tgatgaggac ggctatcagt cctactgcac cgtgtgctgt gagggccgtg    4800
aactgctgct gtgcagtaac acaagctgct gcagatgctt ctgtgtggag tgtctggagg    4860
tgctggtggg cgcaggcaca gctgaggatg ccaagctgca ggaaccctgg agctgctata    4920
tgtgcctccc tcagcgctgc catggggtcc tccgacgcag gaaagattgg aacatgcgcc    4980
tgcaagactt cttcactact gatcctgacc tggaagaatt tgagccaccc aagttgtacc    5040
cagcaattcc tgcagccaaa aggaggccca ttagagtcct gtctctgttt gatggaattg    5100
caacggggta cttggtgctc aaggagttgg gtattaaagt ggaaaagtac attgcctccg    5160
aagtctgtgc agagtccatc gctgtgggaa ctgttaagca tgaaggccag atcaaatatg    5220
tcaatgacgt ccggaaaatc accaagaaaa atattgaaga gtgggcccg ttcgacttgg     5280 tgattggtgg aagcccatgc aatgatctct ctaacgtcaa tcctgcccgc aaaggtttat    5340
atgagggcac aggaaggctc ttcttcgagt tttaccactt gctgaattat acccgcccca    5400
aggagggcga caaccgtcca ttcttctgga tgttcgagaa tgttgtggcc atgaaagtga    5460
atgacaagaa agacatctca agattcctgg catgtaaccc agtgatgatc gatgccatca    5520
aggtgtctgc tgctcacagg gcccggtact tctggggtaa cctacccgga tgaacaggc     5580 ccgtgatggc ttcaaagaat gataagctcg agctgcagga ctgcctggag ttcagtagga    5640
cagcaaagtt aaagaaagtg cagacaataa ccaccaagtc gaactccatc agacagggca    5700
aaaaccagct tttccctgta gtcatgaatg gcaaggacga cgttttgtgg tgcactgagc    5760
tcgaaaggat cttcggcttc cctgctcact acacggacgt gtccaacatg gccgcggcg     5820 cccgtcagaa gctgctgggc aggtcctgga gtgtaccggt catcagacac ctgtttgccc    5880
ccttgaagga ctactttgcc tgtgaaccaa aaaagaagcg gaaagtctag gcggccgcga    5940
ctctagatca taatcagcca taccacattt gtagaggttt tacttgcttt aaaaaacctc    6000
ccacacctcc ccctgaacct gaaacataaa atgaatgcaa ttgttgttgt taacttgttt    6060
attgcagctt ataatggtta caaataaagc aatagcatca caaatttcac aaataaagca    6120
tttttttcac tgcattctag ttgtggtttg tccaaactca tcaatgtatc ttaaggcgta    6180
```

```
aattgtaagc gttaatatttt tgttaaaatt cgcgttaaat ttttgttaaa tcagctcatt    6240
ttttaaccaa taggccgaaa tcggcaaaat cccttataaa tcaaaagaat agaccgagat    6300
agggttgagt gttgttccag tttggaacaa gagtccacta ttaaagaacg tggactccaa    6360
cgtcaaaggg cgaaaaaccg tctatcaggg cgatggccca ctacgtgaac catcacccta    6420
atcaagtttt ttggggtcga ggtgccgtaa agcactaaat cggaacccta aagggagccc    6480
ccgatttaga gcttgacggg gaaagccggc gaacgtggcg agaaaggaag ggaagaaagc    6540
gaaaggagcg ggcgctaggg cgctggcaag tgtagcggtc acgctgcgcg taaccaccac    6600
acccgccgcg cttaatgcgc cgctacaggg cgcgtcaggt ggcacttttc ggggaaatgt    6660
gcgcggaacc cctatttgtt tatttttcta aatacattca aatatgtatc cgctcatgag    6720
acaataaccc tgataaatgc ttcaataata ttgaaaaagg aagagtcctg aggcggaaag    6780
aaccagctgt ggaatgtgtg tcagttaggg tgtggaaagt ccccaggctc cccagcaggc    6840
agaagtatgc aaagcatgca tctcaattag tcagcaacca ggtgtggaaa gtccccaggc    6900
tccccagcag gcagaagtat gcaaagcatg catctcaatt agtcagcaac catagtcccg    6960
cccctaactc cgcccatccc gcccctaact ccgcccagtt ccgcccattc tccgccccat    7020
ggctgactaa ttttttttat ttatgcagag gccgaggccg cctcggcctc tgagctattc    7080
cagaagtagt gaggaggctt ttttggaggc ctaggctttt gcaaagatcg atcaagagac    7140
aggatgagga tcgtttcgca tgattgaaca agatggattg cacgcaggtt ctccggccgc    7200
ttgggtggag aggctattcg gctatgactg ggcacaacag acaatcggct gctctgatgc    7260
cgccgtgttc cggctgtcag cgcaggggcg cccggttctt tttgtcaaga ccgacctgtc    7320
cggtgccctg aatgaactgc aagacgaggc agcgcggcta tcgtggctgg ccacgacggg    7380
cgttccttgc gcagctgtgc tcgacgttgt cactgaagcg ggaagggact ggctgctatt    7440
gggcgaagtg ccggggcagg atctcctgtc atctcacctt gctcctgccg agaaagtatc    7500
catcatggct gatgcaatgc ggcggctgca tacgcttgat ccggctacct gcccattcga    7560
ccaccaagcg aaacatcgca tcgagcgagc acgtactcgg atggaagccg gtcttgtcga    7620
tcaggatgat ctggacgaag agcatcaggg gctcgcgcca gccgaactgt tcgccaggct    7680
caaggcgagc atgcccgacg gcgaggatct cgtcgtgacc catggcgatg cctgcttgcc    7740
gaatatcatg gtggaaaatg gccgcttttc tggattcatc gactgtggcc ggctgggtgt    7800
ggcggaccgc tatcaggaca tagcgttggc tacccgtgat attgctgaag agcttggcgg    7860
cgaatgggct gaccgcttcc tcgtgcttta cggtatcgcc gctcccgatt cgcagcgcat    7920
cgccttctat cgccttcttg acgagttctt ctgagcggga ctctggggtt cgaaatgacc    7980
gaccaagcga cgcccaacct gccatcacga gatttcgatt ccaccgccgc cttctatgaa    8040
aggttgggct tcggaatcgt tttccgggac gccggctgga tgatcctcca gcgcgggat    8100 ctcatgctgg agttcttcgc ccaccctagg gggaggctaa ctgaaacacg gaaggagaca    8160
ataccggaag gaacccgcgc tatgacggca ataaaaagac agaataaaac gcacggtgtt    8220
gggtcgtttg ttcataaacg cggggttcgg tcccagggct ggcactctgt cgataccca    8280 ccgagacccc attggggcca atacgcccgc gtttcttcct tttccccacc caccccccca    8340
agttcgggtg aaggcccagg gctcgcagcc aacgtcgggg cggcaggccc tgccatagcc    8400
tcaggttact catatatact ttagattgat ttaaaacttc attttaatt taaaaggatc    8460 taggtgaaga tcctttttga taatctcatg accaaaatcc cttaacgtga gttttcgttc    8520
cactgagcgt cagaccccgt agaaaagatc aaaggatctt cttgagatcc ttttttttctg    8580
```

```
cgcgtaatct gctgcttgca aacaaaaaaa ccaccgctac cagcggtggt ttgtttgccg    8640
gatcaagagc taccaactct ttttccgaag gtaactggct tcagcagagc gcagatacca    8700
aatactgtcc ttctagtgta gccgtagtta ggccaccact tcaagaactc tgtagcaccg    8760
cctacatacc tcgctctgct aatcctgtta ccagtggctg ctgccagtgg cgataagtcg    8820
tgtcttaccg ggttggactc aagacgatag ttaccggata aggcgcagcg gtcgggctga    8880 acgggggggtt cgtgcacaca gcccagcttg gagcgaacga cctacaccga actgagatac    8940
ctacagcgtg agctatgaga aagcgccacg cttcccgaag ggagaaaggc ggacaggtat    9000
ccggtaagcg gcagggtcgg aacaggagag cgcacgaggg agcttccagg gggaaacgcc    9060
tggtatcttt atagtcctgt cgggtttcgc cacctctgac ttgagcgtcg atttttgtga    9120
tgctcgtcag ggggggcggag cctatggaaa aacgccagca acgcggcctt tttacggttc    9180
ctggcctttt gctggccttt tgctcacatg ttctttcctg cgttatcccc tgattctgtg    9240
gataaccgta ttaccgccat gcat                                            9264

<210> SEQ ID NO 43
<211> LENGTH: 9264
<212> TYPE: DNA
<213> ORGANISM: Artificial Sequence
<220> FEATURE:
<223> OTHER INFORMATION: pCAG-scFvGCN4sfGFPDnmt3bS1

<400> SEQUENCE: 43
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catgggtcga ggtgagcccc acgttctgct tcactctccc catctccccc cctccccac     420 ccccaatttt gtatttattt attttttaat tattttgtgc agcgatgggg gcggggggg     480 ggggggcgcg cgccaggcgg ggcggggcgg ggcgagggc ggggcgggc gaggcggaga      540 ggtgcggcgg cagccaatca gagcggcgcg ctccgaaagt ttccttttat ggcgaggcgg    600
cggcggcggc ggccctataa aaagcgaagc gcgcggcggg cgggagtcgc tgcgttgcct    660
tcgccccgtg ccccgctccg cgccgcctcg cgccgcccgc cccggctctg actgaccgcg    720
ttactcccac aggtgagcgg gcgggacggc ccttctcctc cgggctgtaa ttagcgcttg    780
gtttaatgac ggctcgtttc ttttctgtgg ctgcgtgaaa gccttaaagg ctccggag     840 ggcccttttgt gcggggggga gcggctcggg gggtgcgtgc gtgtgtgtgt gcgtggggag     900
cgccgcgtgc ggcccgcgct gcccggccgg tgtgagcgct gcgggcgcgg cgcggggctt     960
tgtgcgctcc gcgtgtgcgc gaggggagcg cggccggggg cggtgcccg cggtgcgggg   1020 gggctgcgag gggaacaaag gctgcgtgcg gggtgtgtgc gtggggggt gagcagggg    1080 tgtgggcgcg gcggtcgggc tgtaaccccc ccctgcaccc cctcccga gttgctgagc     1140 acggcccggc ttcgggtgcg gggctccgtg cggggcgtgg cgcggggctc gccgtgccgg   1200 gcgggggggtg gcggcaggtg ggggtgccgg cggggcggg gccgcctcgg gccggggagg   1260 gctcgggggga ggggcgcggc ggccccggag cgccggcggc tgtcgaggcg cggcgagccg   1320
```

```
cagccattgc cttttatggt aatcgtgcga gagggcgcag ggacttcctt tgtcccaaat   1380
ctggcggagc cgaaatctgg gaggcgccgc cgcaccccct ctagcgggcg cgggcgaagc   1440
ggtgcggcgc cggcaggaag gaaatgggcg gggagggcct tcgtgcgtcg ccgcgccgcc   1500
gtcccttct ccatctccag cctcggggct gccgcagggg gacggctgcc ttcgggggg    1560
acggggcagg gcggggttcg gcttctggcg tgtgaccggc ggctctagag cctctgctaa   1620
ccatgttcat gccttcttct ttttcctaca gctcctgggc aacgtgctgg ttgttgtgct   1680
gtctcatcat tttggcaaag aattctgcag tcgacggtac catgggcccc gacatcgtga   1740
tgacccagag ccccagcagc ctgagcgcca gcgtgggcga ccgcgtgacc atcacctgcc   1800
gcagcagcac cggcgccgtg accaccagca actacgccag ctgggtgcag agaagcccg    1860
gcaagctgtt caagggcctg atcggcggca ccaacaaccg cgcccccggc gtgcccagcc   1920
gcttcagcgg cagcctgatc ggcgacaagg ccaccctgac catcagcagc ctgcagcccg   1980
aggacttcgc cacctacttc tgcgccctgt ggtacagcaa ccactgggtg ttcggccagg   2040
gcaccaaggt ggagctgaag cgcggcggcg gcggcagcgg cggcggcggc agcggcggcg   2100
gcggcagcag cggcggcggc agcgaggtga gctgctggaa gagcggcggc ggcctggtgc   2160
agcccggcgg cagcctgaag ctgagctgcg ccgtgagcgg cttcagcctg accgactacg   2220
gcgtgaactg ggtgcgccag gccccccggcc gcggcctgga gtggatcggc gtgatctggg   2280
gcgacggcat caccgactac aacagcgccc tgaaggaccg cttcatcatc agcaaggaca   2340
acggcaagaa caccgtgtac ctgcagatga gcaaggtgcg cagcgacgac accgccctgt   2400
actactgcgt gaccggcctg ttcgactact ggggccaggg caccctggtg accgtgagca   2460
gctaccccata cgatgttcca gattacgctg gtggaggcgg aggttctggg ggaggaggta   2520
gtggcggtgg tggttcagga ggcggcggaa gcttggatcc aggtgaggt ggaagcggta    2580
gcaaaggaga agaactttc actggagttg tcccaattct tgttgaatta gatggtgatg    2640
ttaatgggca caattttct gtccgtggag agggtgaagg tgatgctaca aacgaaaac    2700
tcacccttaa atttatttgc actactggaa aactacctgt tccgtggcca acacttgtca   2760
ctactctgac ctatggtgtt caatgctttt cccgttatcc ggatcacatg aaacggcatg   2820
acttttca gagtgccatg cccgaaggtt atgtacagga acgcactata tctttcaaag    2880
atgacgggac ctacaagacg cgtgctgaag tcaagtttga aggtgatacc cttgttaatc   2940
gtatcgagtt aaagggtatt gattttaaag aagatggaaa cattcttgga cacaaactcg   3000
agtacaactt taactcacac aatgtataca tcacggcaga caaacaaaag aatggaatca   3060
aagctaactt caaaattcgc cacaacgttg aagatggttc cgttcaacta gcagaccatt   3120
atcaacaaaa tactccaatt ggcgatggcc ctgtcctttt accagacaac cattacctgt   3180
cgacacaatc tgtcctttcg aaagatccca acgaaaagcg tgaccacatg gtccttcttg   3240
agtttgtaac tgctgctggg attacacatg gcatggatga gctctacaaa ggtgaggtc    3300
ggaccggtgg cggtggcgga ggggctagca tgaagggaga cagcagacat ctgaatgaag   3360
aagagggtgc cagcgggtat gaggagtgca ttatcgttaa tgggaacttc agtgaccagt   3420
cctcagacac gaaggatgct ccctcacccc cagtcttgga ggcaatctgc acagagccag   3480
tctgcacacc agagaccaga ggccgcaggt caagctcccg gctgtctaag agggaggtct   3540
ccagccttct gaattacacg caggacatga caggagatgg agacagagat gatgaagtag   3600
atgatgggaa tggctctgat attctaatgc caaagctcac ccgtgagacc aaggacacca   3660
ggacgcgctc tgaaagcccg gctgtccgaa cccgacatag caatgggacc tccagcttgg   3720
```

```
agaggcaaag agcctccccc agaatcaccc gaggtcggca gggccgccac catgtgcagg    3780
agtaccctgt ggagtttccg gctaccaggt ctcggagacg tcgagcatca tcttcagcaa    3840
gcacgccatg gtcatcccct gccagcgtcg acttcatgga agaagtgaca cctaagagcg    3900
tcagtacccc atcagttgac ttgagccagg atggagatca ggagggtatg gataccacac    3960
aggtggatgc agagagcaga gatggagaca gcacagagta tcaggatgat aaagagtttg    4020
gaataggtga cctcgtgtgg ggaaagatca agggcttctc ctggtggcct gccatggtgg    4080
tgtcctggaa agccacctcc aagcgacagg ccatgcccgg aatgcgctgg gtacagtggt    4140
ttggtgatgg caagttttct gagatctctg ctgacaaact ggtggctctg ggctgttca    4200
gccagcactt taatctggct accttcaata agctggtttc ttataggaag gccatgtacc    4260
acactctgga gaaagccagg gttcgagctg gcaagacctt ctccagcagt cctggagagt    4320
cactggagga ccagctgaag cccatgctgg agtgggccca cggtggcttc aagcctactg    4380
ggatcgaggc cctcaaaccc aacaagaagc aaccagtggt taataagtcg aaggtgcgtc    4440
gttcagacag taggaactta gaacccagga gacgcgagaa caaaagtcga agacgcacaa    4500
ccaatgactc tgctgcttct gagtcccccc cacccaagcg cctcaagaca aatagctatg    4560
gcgggaagga ccgaggggag gatgaggaga gccgagaacg gatggcttct gaagtcacca    4620
acaacaaggg caatctggaa gaccgctgtt gtcctgtgg aaagaagaac cctgtgtcct    4680
tccaccccct ctttgagggt gggctctgtc agagttgccg ggatcgcttc ctagagctct    4740
tctacatgta tgatgaggac ggctatcagt cctactgcac cgtgtgctgt gagggccgtg    4800
aactgctgct gtgcagtaac acaagctgct gcagatgctt ctgtgtggag tgtctggagg    4860
tgctggtggg cgcaggcaca gctgaggatg ccaagctgca ggaaccctgg agctgctata    4920
tgtgcctccc tcagcgctgc catggggtcc tccgacgcag gaaagattgg aacatgcgcc    4980
tgcaagactt cttcactact gatcctgacc tggaagaatt tgagccaccc aagttgtacc    5040
cagcaattcc tgcagccaaa aggaggccca ttagagtcct gtctctgttt gatggaattg    5100
caacggggta cttggtgctc aaggagttgg gtattaaagt ggaaaagtac attgcctccg    5160
aagtctgtgc agagtccatc gctgtgggaa ctgttaagca tgaaggccag atcaaatatg    5220
tcaatgacgt ccggaaaatc accaagaaaa atattgaaga gtggggcccg ttcgacttgg    5280
tgattggtgg aagcccatgc aatgatctct ctagagtcaa tcctgcccgc aaaggtttat    5340
atgagggcac aggaaggctc ttcttcgagt tttaccactt gctgaattat acccgcccca    5400
aggagggcga caaccgtcca ttcttctgga tgttcgagaa tgttgtggcc atgaaagtga    5460
atgacaagaa agacatctca agattcctgg catgtaaccc agtgatgatc gatgccatca    5520
aggtgtctgt tgctcacagg gcccggtact tctgggtaa cctacccgga tgaacaggc    5580
ccgtgatggc ttcaaagaat gataagctcg agctgcagga ctgcctggag ttcagtagga    5640
cagcaaagtt aaagaaagtg cagacaataa ccaccaagtc gaactccatc agacagggca    5700
aaaaccagct tttccctgta gtcatgaatg gcaaggacga cgttttgtgg tgcactgagc    5760
tcgaaaggat cttcggcttc cctgctcact acacggacgt gtccaacatg gccgcggcg    5820
cccgtcagaa gctgctgggc aggtcctgga gtgtaccggt catcagacac ctgtttgccc    5880
ccttgaagga ctactttgcc tgtgaaccaa aaaagaagcg gaaagtctag gcggccgcga    5940
ctctagatca taatcagcca taccacattt gtagaggttt acttgctttt aaaaaacctc    6000
ccacacctcc ccctgaacct gaaacataaa atgaatgcaa ttgttgttgt taacttgttt    6060
```

```
attgcagctt ataatggtta caaataaagc aatagcatca caaatttcac aaataaagca   6120 ttttttcac tgcattctag ttgtggtttg tccaaactca tcaatgtatc ttaaggcgta    6180
aattgtaagc gttaatattt tgttaaaatt cgcgttaaat ttttgttaaa tcagctcatt   6240
ttttaaccaa taggccgaaa tcggcaaaat cccttataaa tcaaaagaat agaccgagat   6300
agggttgagt gttgttccag tttggaacaa gagtccacta ttaaagaacg tggactccaa   6360
cgtcaaaggg cgaaaaaccg tctatcaggg cgatggccca ctacgtgaac catcacccta   6420
atcaagtttt tgggggtcga ggtgccgtaa agcactaaat cggaacccta aagggagccc   6480
ccgatttaga gcttgacggg gaaagccggc gaacgtggcg agaaaggaag ggaagaaagc   6540
gaaaggagcg ggcgctaggg cgctggcaag tgtagcggtc acgctgcgcg taaccaccac   6600
acccgccgcg cttaatgcgc cgctacaggg cgcgtcaggt ggcacttttc ggggaaatgt   6660
gcgcggaacc cctatttgtt tattttttcta aatacattca aatatgtatc cgctcatgag   6720
acaataaccc tgataaatgc ttcaataata ttgaaaaagg aagagtcctg aggcggaaag   6780
aaccagctgt ggaatgtgtg tcagttaggg tgtggaaagt ccccaggctc cccagcaggc   6840
agaagtatgc aaagcatgca tctcaattag tcagcaacca ggtgtggaaa gtccccaggc   6900 tcccagcag gcagaagtat gcaaagcatg catctcaatt agtcagcaac catagtcccg   6960
cccctaactc cgcccatccc gcccctaact ccgcccagtt ccgcccattc tccgccccat   7020
ggctgactaa ttttttttat ttatgcagag gccgaggccg cctcggcctc tgagctattc   7080
cagaagtagt gaggaggctt ttttggaggc ctaggctttt gcaaagatcg atcaagagac   7140
aggatgagga tcgtttcgca tgattgaaca agatggattg cacgcaggtt ctccggccgc   7200
ttgggtggag aggctattcg gctatgactg ggcacaacag acaatcggct gctctgatgc   7260
cgccgtgttc cggctgtcag cgcaggggcg cccggttctt tttgtcaaga ccgacctgtc   7320
cggtgccctg aatgaactgc aagacgaggc agcgcggcta tcgtggctgg ccacgacggg   7380
cgttccttgc gcagctgtgc tcgacgttgt cactgaagcg ggaagggact ggctgctatt   7440
gggcgaagtg ccggggcagg atctcctgtc atctcacctt gctcctgccg agaaagtatc   7500
catcatggct gatgcaatgc ggcggctgca tacgcttgat ccggctacct gcccattcga   7560
ccaccaagcg aaacatcgca tcgagcgagc acgtactcgg atggaagccg gtcttgtcga   7620
tcaggatgat ctggacgaag agcatcaggg gctcgcgcca gccgaactgt tcgccaggct   7680
caaggcgagc atgcccgacg gcgaggatct cgtcgtgacc catggcgatg cctgcttgcc   7740
gaatatcatg gtgaaaatg gccgcttttc tggattcatc gactgtggcc ggctgggtgt   7800
ggcggaccgc tatcaggaca tagcgttggc tacccgtgat attgctgaag agcttggcgg   7860
cgaatgggct gaccgcttcc tcgtgcttta cggtatcgcc gctcccgatt cgcagcgcat   7920
cgccttctat cgccttcttg acgagttctt ctgagcggga ctctggggtt cgaaatgacc   7980
gaccaagcga cgcccaacct gccatcacga gatttcgatt ccaccgccgc cttctatgaa   8040
aggttgggct tcggaatcgt tttccgggac gccggctgga tgatcctcca gcgcgggat   8100 ctcatgctgg agttcttcgc ccaccctagg gggaggctaa ctgaaacacg gaaggagaca   8160
ataccggaag gaacccgcgc tatgacggca ataaaaagac agaataaaac gcacggtgtt   8220
gggtcgtttg ttcataaacg cggggttcgg tcccagggct ggcactctgt cgataccca    8280 ccgagacccc attggggcca atacgcccgc gtttcttcct tttccccacc ccacccccca   8340
agttcgggtg aaggcccagg gctcgcagcc aacgtcgggg cggcaggccc tgccatagcc   8400
tcaggttact catatatact ttagattgat ttaaaacttc attttaatt taaaaggatc    8460
```

```
taggtgaaga tcctttttga taatctcatg accaaaatcc cttaacgtga gttttcgttc    8520
cactgagcgt cagaccccgt agaaaagatc aaaggatctt cttgagatcc ttttttctg     8580 cgcgtaatct gctgcttgca acaaaaaaaa ccaccgctac cagcggtggt ttgtttgccg    8640
gatcaagagc taccaactct ttttccgaag gtaactggct tcagcagagc gcagatacca   8700
aatactgtcc ttctagtgta gccgtagtta ggccaccact tcaagaactc tgtagcaccg   8760
cctacatacc tcgctctgct aatcctgtta ccagtggctg ctgccagtgg cgataagtcg   8820
tgtcttaccg ggttggactc aagacgatag ttaccggata aggcgcagcg gtcgggctga   8880
acggggggtt cgtgcacaca gcccagcttg gagcgaacga cctacaccga actgagatac   8940
ctacagcgtg agctatgaga aagcgccacg cttcccgaag ggagaaaggc ggacaggtat   9000
ccggtaagcg gcagggtcgg aacaggagag cgcacgaggg agcttccagg gggaaacgcc   9060
tggtatcttt atagtcctgt cgggtttcgc cacctctgac ttgagcgtcg attttgtga   9120 tgctcgtcag gggggcggag cctatggaaa aacgccagca acgcggcctt tttacggttc   9180
ctggcctttt gctggccttt tgctcacatg ttctttcctg cgttatcccc tgattctgtg   9240
gataaccgta ttaccgccat gcat                                          9264
```

<210> SEQ ID NO 44
<211> LENGTH: 7
<212> TYPE: PRT
<213> ORGANISM: Artificial Sequence
<220> FEATURE:
<223> OTHER INFORMATION: tag peptide

<400> SEQUENCE: 44

Gly Val Lys Glu Ser Leu Val
1               5

<210> SEQ ID NO 45
<211> LENGTH: 5
<212> TYPE: PRT
<213> ORGANISM: Artificial Sequence
<220> FEATURE:
<223> OTHER INFORMATION: GS linker

<400> SEQUENCE: 45

Gly Ser Gly Ser Gly
1               5

<210> SEQ ID NO 46
<211> LENGTH: 22
<212> TYPE: PRT
<213> ORGANISM: Artificial Sequence
<220> FEATURE:
<223> OTHER INFORMATION: GS linker

<400> SEQUENCE: 46

Gly Ser Gly Ser Gly Gly Ser Gly Ser Gly Ser Gly Gly Ser Gly Ser
1               5                   10                  15

Gly Gly Ser Gly Ser Gly
            20

<210> SEQ ID NO 47
<211> LENGTH: 43
<212> TYPE: PRT
<213> ORGANISM: Artificial Sequence
<220> FEATURE:
<223> OTHER INFORMATION: GS linker

```
<400> SEQUENCE: 47

Gly Ser Gly Ser Gly Gly Ser Gly Ser Gly Gly Ser Gly Ser Gly Gly
1               5                   10                  15

Ser Gly Ser Gly Gly Ser Gly Gly Ser Gly Ser Gly Gly Ser Gly Ser
                20                  25                  30

Gly Gly Ser Gly Ser Gly Gly Ser Gly Ser Gly
            35                  40
```